US012782347B2

(12) United States Patent
Myers et al.

(10) Patent No.: US 12,782,347 B2
(45) Date of Patent: Nov. 3, 2026

(54) BIONANOMECHANICAL DEVICES FOR USES IN EVALUATING LIQUID DYNAMICS

(71) Applicants: Emory University, Atlanta, GA (US); Children's Healthcare of Atlanta, Inc., Atlanta, GA (US); Georgia Tech Research Corporation, Atlanta, GA (US)

(72) Inventors: David Myers, Atlanta, GA (US); Yonggang Ke, Atlanta, GA (US); Victor Pan, Atlanta, GA (US); Shreyas Dahotre, Atlanta, GA (US); Gabriel Kwong, Atlanta, GA (US)

(73) Assignees: Emory University, Atlanta, GA (US); Children's Healthcare of Atlanta, Inc., Atlanta, GA (US); Georgia Tech Research Corporation, Atlanta, GA (US)

( * ) Notice: Subject to any disclaimer, the term of this patent is extended or adjusted under 35 U.S.C. 154(b) by 875 days.

(21) Appl. No.: 17/908,517

(22) PCT Filed: Mar. 12, 2021

(86) PCT No.: PCT/US2021/022189
§ 371 (c)(1),
(2) Date: Aug. 31, 2022

(87) PCT Pub. No.: WO2021/183938
PCT Pub. Date: Sep. 16, 2021

(65) Prior Publication Data

US 2023/0121144 A1 Apr. 20, 2023

Related U.S. Application Data

(60) Provisional application No. 63/073,212, filed on Sep. 1, 2020, provisional application No. 62/989,566, filed on Mar. 13, 2020.

(51) Int. Cl.
*G01N 33/542* (2006.01)
*B82Y 15/00* (2011.01)
(Continued)

(52) U.S. Cl.
CPC ................ *G01N 33/54373* (2013.01); *G01N 21/6428* (2013.01); *G01N 2021/6432* (2013.01)

(58) Field of Classification Search
None
See application file for complete search history.

(56) References Cited

U.S. PATENT DOCUMENTS

| | | | | |
|---|---|---|---|---|
| 2009/0227043 | A1 | 9/2009 | Huang | |
| 2017/0108517 | A1* | 4/2017 | Mao | B82Y 5/00 |

(Continued)

FOREIGN PATENT DOCUMENTS

| | | |
|---|---|---|
| WO | 2012074588 | 6/2012 |
| WO | 2013049444 | 4/2013 |

OTHER PUBLICATIONS

Corodova et al. Combining single-molecule manipulation and single-molecule detection, Current Opinion in Structural Biology 2014, 28:142-148.

(Continued)

*Primary Examiner* — Neil N Turk
(74) *Attorney, Agent, or Firm* — Emory Patent Group

(57) ABSTRACT

It is an object of this disclosure to provide systems, devices, and methods for the direct use of fluorescent reporters that measure multiaxial and dynamic shear flows that occur invitro or in vivo across a surface of interest, where shear flows canbe measured, quantified and/or correlated to physiological changes in cells or tissues in real time. In certain embodiments, this disclosure contemplates imaging or visualizing the shear field applied to a surface, e.g., a surface of cells or inner lining of a blood vessel, the lumen of pumping lymphatics, within the bile duct, vessels with significant leakage, inflamed endothelium, tumor vasculature, or other systems.

12 Claims, 6 Drawing Sheets

Specification includes a Sequence Listing.

(51) Int. Cl.
*G01N 21/64* (2006.01)
*G01N 33/543* (2006.01)

(56) References Cited

U.S. PATENT DOCUMENTS

| | | | | |
|---|---|---|---|---|
| 2018/0010166 | A1 | 1/2018 | Pierce | |
| 2019/0219600 | A1 | 7/2019 | Salaita | |
| 2021/0024985 | A1 | 1/2021 | Salaita | |
| 2021/0071237 | A1* | 3/2021 | Taylor | C12Q 1/68 |

OTHER PUBLICATIONS

Houston et al. Delivery and Expression of Fluid Shear Stress-Inducible Promoters to the Vessel Wall: Applications for Cardiovascular Gene Therapy, Human Gene Therapy, 1999, 10:3031-3044.
Jahanban et al. Static DNA Nanostructures For Cancer Theranostics: Recent Progress In Design And Applications, Nanotechnology, Science and Applications 2019:12 25-46.
Liu et al. DNA-based nanoparticle tension sensors reveal that T-cell receptors transmit defined pN forces to their antigens for enhanced fidelity, PNAS, 2016, vol. 113, No. 20, 5610-5615.
Liu et al. Molecular Tension Probes for Imaging Forces at the Cell Surface, Acc. Chem. Res. 2017, 50, 2915-2924.
Ma et al. DNA probes that store mechanical information reveal transient piconewton forces applied by T cells, PNAS, 2019, vol. 116, No. 34, 16949-16954.
Maan et al. Modeling cell-substrate de-adhesion dynamics under fluid shear, Phys. Biol. 2018, 15, 046006.
Menendez-Gil et al. Fluorescent Molecular Beacons Mimicking RNA Secondary Structures to Study RNA Chaperone Activity, Chapter 3, Tilman Heise (ed.), RNA Chaperones: Methods and Protocols, Methods in Molecular Biology, vol. 2106, 41-58. 2020.
Oshinowo et al. Getting a good view: in vitro imaging of platelets under flow, Platelets, 2020, 31:5, 570-579.
Poelma et al. In vivo blood flow and wall shear stress measurements in the vitelline network, Exp Fluids (2008) 45:703-713.

* cited by examiner

BIONANOMECHANICAL DEVICES FOR USES IN EVALUATING LIQUID DYNAMICS

CROSS-REFERENCE TO RELATED APPLICATIONS

This application is the National Stage of International Application No. PCT/US2021/022189 filed Mar. 12, 2021, which claims the benefit of U.S. Provisional Application No. 62/989,566 filed Mar. 13, 2020 and U.S. Provisional Application No. 63/073,212 filed Sep. 1, 2020. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 20117PCT_ST25.txt. The text file is 100 KB, was created on Mar. 11, 2021, and is being submitted electronically via EFS-Web.

BACKGOUND

Shear stress alters certain biological signaling pathways including those involved with growth, coagulation, inflammation, and extracellular matrix deposition. For example, when shear stress is applied to cultured endothelial cells, they will re-arrange their cytoskeleton to align with the direction of flow in a matter of hours. Such changes have implications for human health, as the shear stresses induced from disturbed flow conditions may lead to life threatening conditions such as atherosclerosis and coronary microvasculature disease. Thus, there is a need to develop improved techniques for evaluating liquid dynamic in biological contexts.

Oshinowo et al. report in vitro imaging of platelets under flow. Platelets, 2020, 31(5): 570-579. Liu et al. report molecular tension probes for imaging forces at the cell surface. Acc Chem Res, 2017, 50(12): 2915-2924. See also WO 2013/049444. Ma et al. report DNA probes that store mechanical information reveal transient piconewton forces applied by T cells. Proc Natl Acad Sci USA, 2019, 116(34): 16949-16954. See also U.S. patent application Ser. No. 16/913,187.

References cited herein are not an admission of prior art.

SUMMARY

It is an object of this disclosure to provide systems, devices, and methods for the direct use of fluorescent reporters that measure multiaxial and dynamic shear flows that occur in vitro or in vivo across a surface of interest, where shear flows can be measured, quantified and/or correlated to physiological changes in cells or tissues in real time. In certain embodiments, this disclosure contemplates imaging or visualizing the shear field applied to a surface, e.g., a surface of cells or inner lining of a blood vessel, the lumen of pumping lymphatics, within the bile duct, vessels with significant leakage, inflamed endothelium, tumor vasculature, or other systems.

In certain embodiments, this disclosure relates to a molecular arm comprising an anchor on one end, a force indicator (optical force transducer), a tether, and a shear flow resistor (mechanical amplifier) on the other end, wherein the shear flow resistor causes the force indicator to expand providing an optical signal if exposed to a liquid that flows past the molecular arm in a stationary position at or above a critical velocity. In certain embodiment, the shear flow resistor causes the force indicator to expand providing an optical signal if the liquid flows past the arm in a stationary position or through the channel at or above a velocity of 0.5, 5, 10, 15, 20, 25, 30, 40, 50, 60, 70, 80, 90, 100, 200, or 300 dynes/$cm^2$. In certain embodiments, the molecular arm or any segment thereof, e.g., shear flow resistor further contains a label, e.g., fluorescent label.

In certain embodiments, this disclosure relates to a molecular arm comprising a specific binding agent at one end, a nucleic acid force indicator comprising multiple hairpin domains, a nucleic acid tether, and a shear flow resistor on the other end wherein the shear flow resistor causes the hairpin domains in the force indicator to expand providing an optical signal if exposed to a liquid that flows past the arm in a stationary position at or above a critical velocity.

In certain embodiments, this disclosure relates to an optical shear flow system comprising: a) a channel comprising a surface; b) a molecular arm comprising an anchor, a force indicator, a tether, and a shear flow resistor; and c) a liquid in the channel; wherein the anchor is attached to the surface; and wherein the shear flow resistor causes the force indicator to expand providing an optical signal if the liquid flows through the channel at or above a critical velocity.

In certain embodiments, it is contemplated that the channel has a cross-sectional area of less than 100, 50, 10, or 5 $cm^2$. In certain embodiments, it is contemplated that the surface is glass, metal, polymer, protein, cell, group of cells, or combinations thereof. In certain embodiments, it is contemplated that the channel is a vascular channel, blood vessel, artery, capillary, inside a tissue or organ.

In certain embodiments, it is contemplated that the anchor is an antibody, agent, specific binding agent, ligand or receptor and the surface comprises an antigen, specific binding agent, agent, receptor or a ligand, respectively. In certain embodiments, it is contemplated that the anchor is an antibody such as an antibody or binding fragment thereof to CD31, VCAM, CD43, or $\alpha4\beta1$ or other specific binding agent, ligand, or receptor to CD31, VCAM, CD43, or $\alpha4\beta1$.

In certain embodiments, it is contemplated that the tether and/or the shear flow resistor comprises nucleic acid sequences or amino acid sequences. In certain embodiments, it is contemplated that the tether and/or the shear flow resistor comprises nucleic acid sequences with a G and C content of greater than 10, 15, 16, 17, 18, 19, 20, 21, 22, 23, 24, 25, 26, 27, 28, 29, 30, 35, 40, or 50% of the total nucleotide bases. In certain embodiments, it is contemplated that the tether and/or the shear flow resistor comprises nucleic acid sequences with a G and C content of between 20-25%, 20-30%, 20-35%, 10-25%, 15-25%, 15-30%, 15-35%, of the total nucleotide bases.

In certain embodiments, it is contemplated that the force indicator and tether comprise nucleic acid sequences, and the force indicator spontaneously forms multiple hairpin domains.

In certain embodiments, it is contemplated that the hairpin domains or nearby segments contain a quencher and fluorophore in sufficiently close proximity to prevent an optical signal and the optical signal is a result of the hairpin domains dehybridizing separating the quencher from the fluorophore.

In certain embodiments, it is contemplated that the optical signal is a result of hairpin domains dehybridizing forming single stranded segments and the optical signal is a result of fluorescent probes in the liquid hybridizing the single stranded segments.

In certain embodiments, it is contemplated that the shear flow resistor is a bead attached through the tether. In certain embodiments, it is contemplated that the shear flow resistor comprises branched nucleic acids attached through the tether.

In certain embodiments, it is contemplated that the branched nucleic acids have 2, 3, 4, 5, 10, 25, 50, 100, or 150 or more primary branch points providing primary nucleic acid branches from a linear or circular nucleic acid. In certain embodiments, it is contemplated that the primary nucleic acid branches have secondary branch points providing second nucleic acid branches. In certain embodiments, it is contemplated that the secondary nucleic acid branches have tertiary branch points providing tertiary nucleic acid branches. In certain embodiments, it is contemplated that the tertiary nucleic acid branches have quaternary branch points providing quaternary nucleic acid branches.

In certain embodiments, this disclosure relates to methods of imaging, detecting, measuring, or quantifying shear flow in a channel comprising providing an optical shear flow system disclosed herein and imaging the channel or detecting, measuring, or quantifying an optical signal in the channel.

In certain embodiments, it is contemplated that imaging includes imaging the optical signal produced when the liquid flows through the channel at or above a critical velocity causing the force indicator to expand. In certain embodiments, it is contemplated that an image is recorded on computer readable medium.

In certain embodiments, this disclosure relates to in vivo methods of diagnosing shear flow of a bodily fluid such as shear flow associated with blood flow in a subject comprising administering into the circulatory system, e.g., intravenously, a molecular arm disclosed herein to a subject, wherein the molecular arm anchors to a surface or wall of a vascular channel, e.g., blood vessel, artery, capillary, or heart, wherein the shear flow resistor causes the force indicator to expand providing an optical signal if the bodily fluid flows past the surface or through the channel at or above a critical velocity, and imaging, detecting, measuring, or quantifying the optical signal, and wherein the optical signal indicates that the subject has bodily fluid flow above a calibrated value associated with the molecular arm, e.g., high blood flow at a certain location, or wherein a lack of an optical signal indicates the subject does not have a bodily fluid flow above a calibrated value associated with the molecular arm.

In certain embodiments, it is contemplated that an image, measurement, or diagnosis is recorded on computer readable medium. In certain embodiments, it is contemplated that an image, measurement, or diagnosis is communicated or transmitted to a medical professional.

In certain embodiments, this disclosure relates to any nucleic acid sequence disclosed herein (e.g., SEQ ID NO: 1-406) optionally conjugated to a label, fluorescent dye, or quencher.

DETAILED DISCUSSION

Figure 1A:
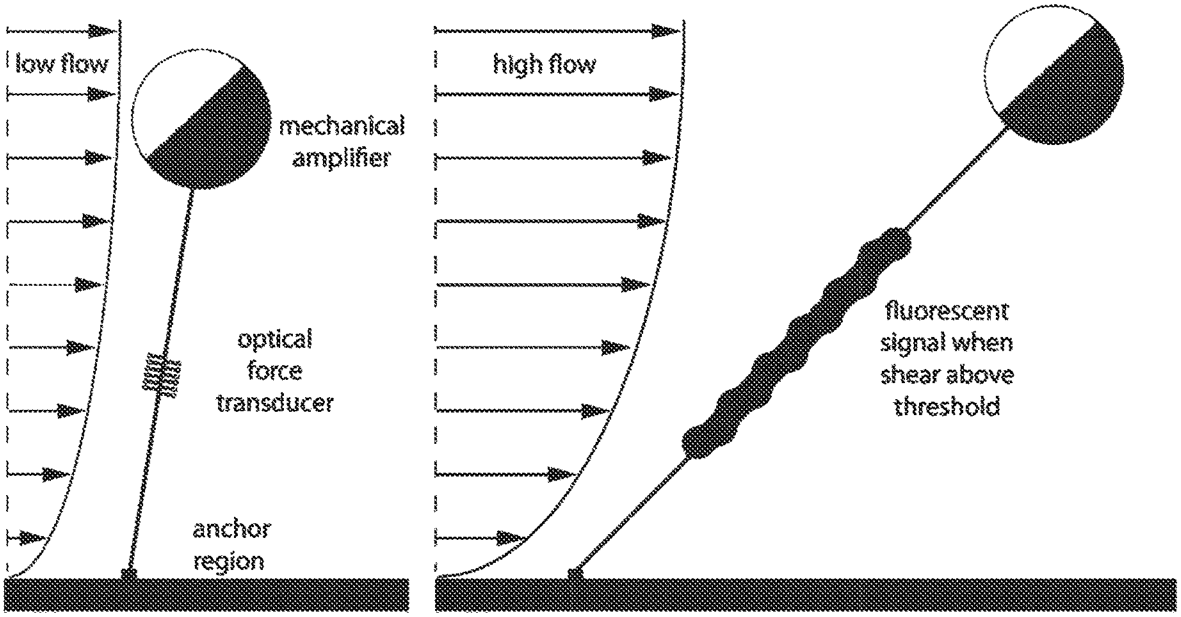
FIG. 1A DNA based optical reporter of shear stress. One creates a reporter that directly measures shear stress useful for shear based in vivo sensors and therapeutics and testing hypotheses related to molecular biophysics. Each bionanomechanical reporter is similar to a kite and contains: 1) an antibody-based anchor targeted to a ligand of interest, 2) a DNA or protein-based optical force transducer that fluoresces when unfolded at a threshold force, and 3) a mechanical amplifier (kite) that increases the total force on the transducer. Data indicates that a bead (kite) generates tensile force as a function of fluidic drag force and bead size. As the tensile force increases, an optical force reporter, which consists of a series of DNA hairpins with fluor-quencher pairs, unfolds and fluoresces. By creating large numbers of multiplexed reporters with varied shear force sensitivities and anchors attaching to ligands of interest, one can visualize complex, multiaxial, in vivo force fields. For example, in vitro physiologically relevant shear stresses were measured from 0.5 dynes/cm$^2$ to 25 dynes/cm$^2$ by changing the bead size.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps.

"Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods, compared to those of the corresponding compositions or methods disclosed herein.

The term "specific binding agent" refers to a molecule, such as a proteinaceous molecule, that binds a target molecule with a greater affinity than other random molecules or proteins. Examples of specific binding agents include antibodies that bind an epitope of an antigen or a receptor which binds a ligand. "Specifically binds" refers to the ability of a specific binding agent (such as an ligand, receptor, enzyme, antibody or binding region/fragment thereof) to recognize and bind a target molecule or polypeptide, such that its affinity (as determined by, e.g., affinity ELISA or other assays) is at least 10 times as great, but optionally 50 times as great, 100, 250 or 500 times as great, or even at least 1000 times as great as the affinity of the same for any other or other random molecule or polypeptide.

In certain contexts, an "antibody" refers to a protein based molecule that is naturally produced by animals in response to the presence of a protein or other molecule or that is not recognized by the animal's immune system to be a "self" molecule, i.e. recognized by the animal to be a foreign molecule and an antigen to the antibody. The immune system of the animal will create an antibody to specifically bind the antigen, and thereby targeting the antigen for elimination or degradation. It is well recognized by skilled artisans that the molecular structure of a natural antibody can be synthesized and altered by laboratory techniques. Recombinant engineering can be used to generate fully synthetic antibodies or fragments thereof providing control over variations of the amino acid sequences of the antibody. Thus, as used herein the term "antibody" is intended to include natural antibodies, monoclonal antibody, or non-naturally produced synthetic antibodies, and binding fragments, such as single chain binding fragments. These antibodies may have chemical modifications. The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same antigen. The term "monoclonal" is not limited to any particular method for making the antibody, nor is the term limited to antibodies produced in a particular species, e.g., mouse, rat, etc.

From a structural standpoint, an antibody is a combination of proteins: two heavy chain proteins and two light chain proteins. The heavy chains are longer than the light chains. The two heavy chains typically have the same amino acid sequence. Similarly, the two light chains have the same amino acid sequence. Each of the heavy and light chains contain a variable segment that contains amino acid sequences which participate in binding to the antigen. The variable segments of the heavy chain do not have the same amino acid sequences as the light chains. The variable segments are often referred to as the antigen binding domains. The antigen and the variable regions of the antibody may physically interact with each other at specific smaller segments of an antigen often referred to as the "epitope." Epitopes usually consist of surface groupings of molecules, for example, amino acids or carbohydrates. The terms "variable region," "antigen binding domain," and "antigen binding region" refer to that portion of the antibody molecule which contains the amino acid residues that interact with an antigen and confer on the antibody its specificity and affinity for the antigen. Small binding regions within the antigen-binding domain that typically interact with the epitope are also commonly alternatively referred to as the "complementarity-determining regions, or CDRs."

As used herein, the term "ligand" refers to an organic molecule, i.e., substantially comprised of carbon, hydrogen, and oxygen, that binds a "receptor." Receptors are organic molecules typically found on the surface of a cell. Through binding a ligand to a receptor, the cell has a signal of the extra cellular environment which may cause changes inside the cell. As a convention, a ligand is usually used to refer to the smaller of the binding partners from a size standpoint, and a receptor is usually used to refer to a molecule that spatially surrounds the ligand or portion thereof. However as used herein, the terms can be used interchangeably as they generally refer to molecules that are specific binding partners. For example, a glycan may be expressed on a cell surface glycoprotein and a lectin may bind the glycan. As the glycan is typically smaller and surrounded by the lectin during binding, it may be considered a ligand even though it is a receptor of the lectin binding signal on the cell surface. In another example, a double stranded oligonucleotide sequence contains two complimentary nucleic acid sequences. Either of the single stranded sequences may be consider the ligand or receptor of the other. In certain embodiments, a ligand is contemplated to be a small molecule. In certain embodiments, a receptor is contemplated to be a compound that has a molecular weight of greater than 2,000 or 5,000. In any of the embodiments disclosed herein the position of a ligand and a receptor may be switched.

As used herein, the term "small molecule" refers to any variety of covalently bound molecules with a molecular weight of less than 900 or 1000. Typically, the majority of atoms include carbon, hydrogen, oxygen, nitrogen, and to a lesser extent sulfur and/or a halogen. Examples include steroids, short peptides, mono or polycyclic aromatic or non-aromatic, heterocyclic compounds.

As used herein, the term "surface" refers to the outside part of an object. Examples of contemplated surfaces are on a particle, bead, wafer, array, well, microscope slide, transparent or opaque glass, polymer, or metal, or in vitro or in vivo cell, or group of cells.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a peptide "label " refers to incorporation of a peptide, wherein the sequence can be identified by a specific binding agent, antibody, or bind to a metal such as nickel/ nitrilotriacetic acid, e.g., a poly-histidine sequence. Specific binding agents and metals can be conjugated to solid surfaces to facilitate isolation and purification methods. A label contemplates the covalent attachment of biotinyl moieties that can be detected by marked avidin (for example, streptavidin containing a fluorescent marker or enzymatic activity that can be detected by optical or colorimetric methods). Various methods of labeling nucleic acids, polypeptides and glycoproteins are known in the art and may be used. Examples of labels include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels may be attached by spacer arms of various lengths to reduce potential steric hindrance.

As used herein, the term "nucleic acid" is meant to include ribonucleic or deoxyribonucleic acid, nucleobase polymers, or mixtures thereof. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. With regard to the nucleobases, it is contemplated that the term encompasses isobases, otherwise known as modified bases, e.g., are isoelectronic or have other substitutes configured to mimic naturally occurring hydrogen bonding base-pairs, e.g., within any of the sequences herein U may be substituted for T, or T may be substituted for U. Examples of nucleotides with modified adenosine or guanosine include, but are not limited to, hypoxanthine, xanthine, 7-methylguanine. Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983, 6,037,120, 6,617,106, and 6,977,161).

The term "nucleobase polymer" refers to nucleic acids and chemically modified forms with nucleobase monomers. In certain embodiments, methods and compositions disclosed herein may be implemented with a nucleobase polymers comprising units of a ribose, 2'deoxyribose, locked nucleic acids (1-(hydroxymethyl)-2,5-dioxabicyclo[2.2.1]heptan-7-ol), 2'-O-methyl groups, a 3'-3'-inverted thymidine, phosphorothioate linkages, or combinations thereof. In certain embodiments, the nucleobase polymer may be less than 100, 50, or 35 nucleotides or nucleobases. Nucleobase polymers may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methylribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl)morpholino) (piperazin-1-yl)phosphinate, or peptide nucleic acids or combinations thereof. In certain embodiments, the nucleobase polymer can be modified to contain a phosphodiester bond, methylphosphonate bond or phosphorothioate bond. The nucleobase polymers can be modified, for example, 2'-amino, 2'-fluoro, 2'-O-methyl, 2'-H of the ribose ring. Constructs can be purified by gel electrophoresis using general methods or can be purified by high pressure liquid chromatography and re-suspended in water. In certain embodiments, nucleobase polymers include one or more (e.g., about 1, 2, 3, 4, 5, 6, 7, 8, 9, 10, or more) LNA "locked nucleic acid" nucleotides such as a 2',4'-C methylene bicyclo nucleotide (see for example U.S. Pat. Nos. 6,639,059, 6,670,461, 7,053,207). In one embodiment, the disclosure features modified nucleobase polymers, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions.

As used herein, the term "conjugated" refers to linking molecular entities through covalent bonds, or by other specific binding interactions, such as due to hydrogen bonding or other van der Walls forces. The force to break a covalent bond is high, e.g., about 1500 pN for a carbon to carbon bond. The force to break a combination of strong protein interactions is typically a magnitude less, e.g., biotin to streptavidin is about 150 pN. Thus, a skilled artisan would understand that conjugation must be strong enough to restrict the breaking of bonds in order to implement the intended results. In certain embodiments, the term conjugated is intended to include linking molecular entities that do not break unless exposed to a force of about greater than about 5, 10, 25, 50, 75, 100, 125, or 150 pN depending on the context.

As used herein, "subject" refers to any animal, preferably a human patient, livestock, or domestic pet.

Unless stated otherwise as apparent from the following discussion, it will be appreciated that terms such as "detecting," "receiving," "quantifying," "mapping," "generating," "registering," "determining," "obtaining," "processing," "computing," "deriving," "estimating," "calculating," "inferring" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

In some embodiments, the disclosed methods may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and/or method of the disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures may be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

Fluidic Shear Sensor

A tool capable of measuring changes in the spatial fluid velocity directly at a vessel wall is useful for scientific research. This disclosure relates to bionanomechanical reporters that are similar to a kite and contains: 1) an antibody-based anchor targeted to a ligand of interest, 2) a optical force transducer (e.g., DNA or protein-based) that fluoresces when unfolded at a threshold force, and 3) a mechanical amplifier (kite) that increases the total force on the transducer (FIG. 1A). A bead (kite) generates tensile force as a function of fluidic drag force and bead size. As the tensile force increases, the optical force reporter, which consists of a series of DNA hairpins with fluorophore-quencher pairs, unfolds and fluoresces.

Figure 1B:
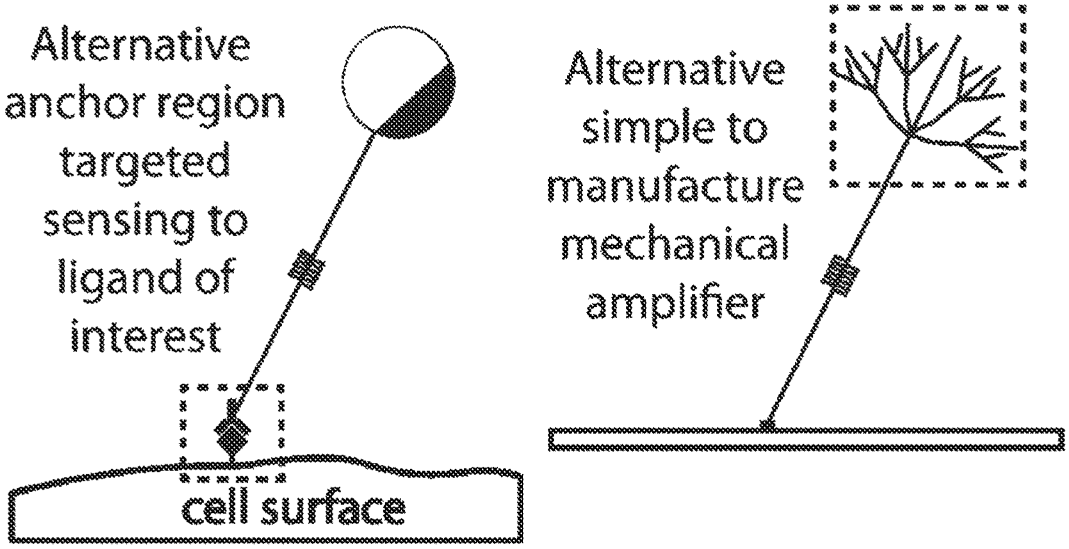
FIG. 1B illustrates an antibody-based anchor to a cell surface and a dendrimer based mechanical amplifier.
Figure 1C:
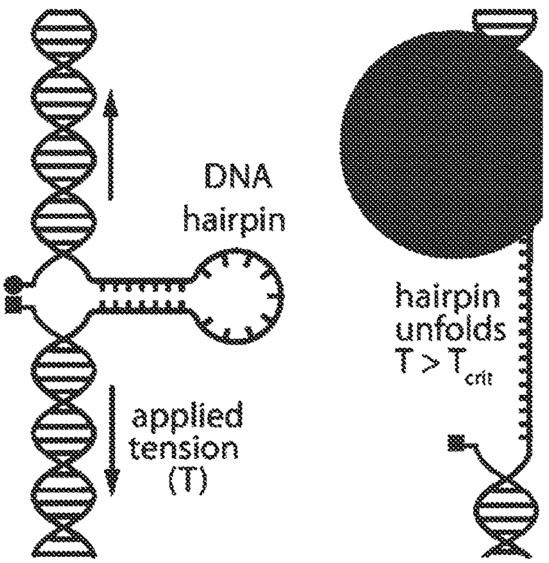
FIG. 1C illustrates the fluorescent signal (black circle) using DNA hairpins designed to unfold at a critical tension leading to fluorescence. As the bead experiences drag, which is proportional to the fluid velocity, the DNA strand tethering the bead to the wall experiences tension. This tension is reported optically by multiple added hairpins that each have fluorophore-quencher pairs which fluoresce when unfolded. In flow conditions, fluorescence occurs whenever the applied fluidic shear force exceeds a critical value which can be modified by changing the nanoreporter design. Changing the number and type of base pairs enables us to create DNA hairpins that unfold at a specified mechanical force. When combined with beads of different sizes and fluorophores of different emission spectra, one can create a multiplexed system that measures the localized shear stress.

DNA nanomechanics can be used to: 1) spatially constrain an object to be within a specified distance of a surface and 2) measure the forces coupled into a DNA strand assembly. DNA nanostructures were created that constrain the movement of a bead near a wall (FIG. 1B). The position of a bead in relation to the wall depends on lift forces generated near the wall surface as well as drag forces. As the bead experiences drag, which is proportional to the fluid velocity, the DNA strand tethering the bead to the wall experiences tension. This tension is reported optically by multiple (e.g., ten) added hairpins that each have fluorophore-quencher pairs, which fluoresce when unfolded (FIG. 1C). In flow conditions, the system will fluoresce whenever the applied fluidic shear force exceeds a critical value. Changing the number and type of base pairs enables us to create DNA hairpins that unfold at a specified mechanical force.

A DNA bead-based structure are created to report the wall shear stress applied by a fluid to an interface. This structure may be: 1) designed to measure a range of shear stresses; 2) used en masse; and 3) have consistent static and dynamic performance. The fluorescence signal generated from a single fluorophore quencher is typically undetectable using confocal microscopy. About 10-12 fluorophores contained within the point spread function (about 250 nm) are sufficient to create a signal. A nanoreporter featuring 10 serially connected hairpins was created.

Figure 1D:
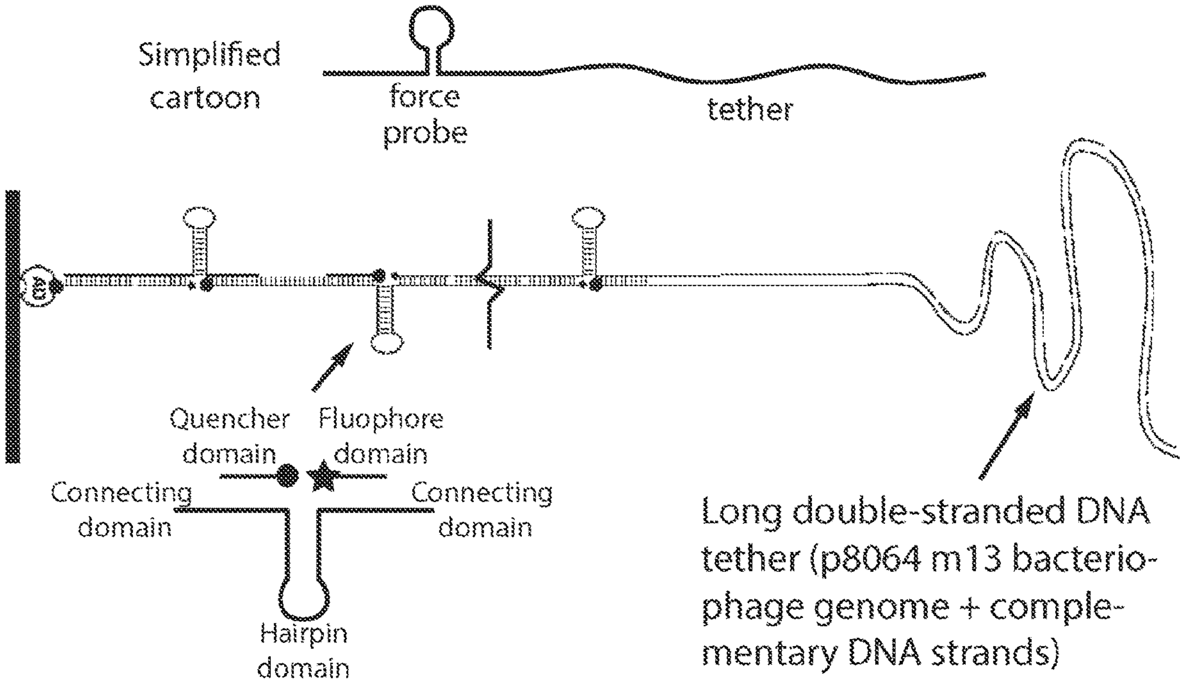
FIG. 1D illustrates force probes with ten hairpins in series with a double stranded tether modified from a m13 bacteriophage genome (circular single-stranded DNA, 8064 bases in length) linearized with restriction enzyme BsaAI.

The sequence of the hairpin relates to the force required for the hairpin to open. GC base pairing utilizes 3 hydrogen bonds compared to the 2 or AT base pairs. Thus, less GC pairs require less force to separate; however, 0% GC hairpins could open spontaneously at room temperature. Preliminary calculations suggested that a hairpin sequence of 22% GC would be a good place to start. A functional unit was designed that could be repeated as desired to increase the number of force-sensing hairpins in series (FIG. 1D). This single functional unit needed five domains, two (one at either end) for connecting to neighboring units, and three in the middle for assembling the hairpin and its fluorophore and quencher components. In order to reduce unit-to-unit variability and promote full signal of the serial hairpin assembly in the smallest flow range possible, the three domains were conserved for hairpin-fluorophore-quencher assembly across all hairpin units. Contrarily, the two sticky end domains flanking the hairpin component are unique for all hairpin units. At one end of the entire hairpin chain, DNA strand is modified with digoxigenin allowing for selective attachment of the strand to a surface bound protein that specifically binds digoxigenin. At the other end of the chain, a strand connects the hairpin assembly to a double stranded DNA tether.

The double stranded tether (dsTether) was generated by modifying m13 bacteriophage genome (circular single-stranded DNA, 8064 bases in length). Exposure to a restriction enzyme BsaAI resulted in linear form. Bacteriophage genome p8064 has many restriction sites for the BsaAI enzyme. Thus, to enhance single location cleavage a single short oligo was hybridized to the m13 that made one restriction site double stranded allowing for controlled cleavage at the desired site. The BsaAI enzyme was inactivated by heating.

```
Linearized sequence
                                                   (SEQ ID NO: 406)
CACGTTATACGTGCTCGTCAAAGCAACCATAGTACGCGCCCTGTAGCGGCGCATTAA

GCGCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTACGGCACCTC

GACCCCAAAAAACTTGATTTGGGTGATGGTTCACGTAGTGGGCCATCGCCCTGATAG

ACGGTTTTTCGCCCTTTGACGTTGGAGTCCACGTTCTTTAATAGTGGACTCTTGTTCC

AAACTGGAACAACACTCAACCCTATCTCGGGCTATTCTTTTGATTTATAAGGGATTTT

GCCGATTTCGGAACCACCATCAAACAGGATTTTCGCCTGCTGGGGCAAACCAGCGT

GGACCGCTTGCTGCAACTCTCTCAGGGCCAGGCGGTGAAGGGCAATCAGCTGTTGC

CCGTCTCACTGGTGAAAAGAAAAACCACCCTGGCGCCCAATACGCAAACCGCCTCT

CCCCGCGCGTTGGCCGATTCATTAATGCAGCTGGCACGACAGGTTTCCCGACTGGAA

AGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAAC

AATTTCACACAGGAAACAGCTATGACCATGATTACGAATTCGAGCTCGGTACCCGG

GGATCCTCAACTGTGAGGAGGCTCACGGACGCGAAGAACAGGCACGCGTGCTGGCA

GAAACCCCCGGTATGACCGTGAAAACGGCCCGCCGCATTCTGGCCGCAGCACCACA

GAGTGCACAGGCGCGCAGTGACACTGCGCTGGATCGTCTGATGCAGGGGGCACCGG

CACCGCTGGCTGCAGGTAACCCGGCATCTGATGCCGTTAACGATTTGCTGAACACAC

CAGTGTAAGGGATGTTTATGACGAGCAAAGAAACCTTTACCCATTACCAGCCGCAG

GGCAACAGTGACCCGGCTCATACCGCAACCGCGCCCGGCGGATTGAGTGCGAAAGC

GCCTGCAATGACCCCGCTGATGCTGGACACCTCCAGCCGTAAGCTGGTTGCGTGGGA

TGGCACCACCGACGGTGCTGCCGTTGGCATTCTTGCGGTTGCTGCTGACCAGACCAG

CACCACGCTGACGTTCTACAAGTCCGGCACGTTCCGTTATGAGGATGTGCTCTGGCC

GGAGGCTGCCAGCGACGAGACGAAAAAACGGACCGCGTTTGCCGGAACGGCAATC

AGCATCGTTTAACTTTACCCTTCATCACTAAAGGCCGCCTGTGCGGCTTTTTTTACGG

GATTTTTTTATGTCGATGTACACAACCGCCCAACTGCTGGCGGCAAATGAGCAGAAA

TTTAAGTTTGATCCGCTGTTTCTGCGTCTCTTTTTCCGTGAGAGCTATCCCTTCACCAC

GGAGAAAGTCTATCTCTCACAAATTCCGGGACTGGTAAACATGGCGCTGTACGTTTC
```

-continued

GCCGATTGTTTCCGGTGAGGTTATCCGTTCCCGTGGCGGCTCCACCTCTGAAAGCTT

GGCACTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAGGCCCG

CACCGATCGCCCTTCCCAACAGTTGCGCAGCCTGAATGGCGAATGGCGCTTTGCCTG

GTTTCCGGCACCAGAAGCGGTGCCGGAAAGCTGGCTGGAGTGCGATCTTCCTGAGG

CCGATACTGTCGTCGTCCCCTCAAACTGGCAGATGCACGGTTACGATGCGCCCATCT

ACACCAACGTGACCTATCCCATTACGGTCAATCCGCCGTTTGTTCCCACGGAGAATC

CGACGGGTTGTTACTCGCTCACATTTAATGTTGATGAAAGCTGGCTACAGGAAGGCC

AGACGCGAATTATTTTTGATGGCGTTCCTATTGGTTAAAAAATGAGCTGATTTAACA

AAAATTTAATGCGAATTTTAACAAAATATTAACGTTTACAATTTAAATATTTGCTTAT

ACAATCTTCCTGTTTTTGGGGCTTTTCTGATTATCAACCGGGGTACATATGATTGACA

TGCTAGTTTTACGATTACCGTTCATCGATTCTCTTGTTTGCTCCAGACTCTCAGGCAA

TGACCTGATAGCCTTTGTAGATCTCTCAAAAATAGCTACCCTCTCCGGCATTAATTTA

TCAGCTAGAACGGTTGAATATCATATTGATGGTGATTTGACTGTCTCCGGCCTTTCTC

ACCCTTTTGAATCTTTACCTACACATTACTCAGGCATTGCATTTAAAATATATGAGGG

TTCTAAAAATTTTTATCCTTGCGTTGAAATAAAGGCTTCTCCCGCAAAAGTATTACA

GGGTCATAATGTTTTTGGTACAACCGATTTAGCTTTATGCTCTGAGGCTTTATTGCTT

AATTTTGCTAATTCTTTGCCTTGCCTGTATGATTTATTGGATGTTAATGCTACTACTAT

TAGTAGAATTGATGCCACCTTTTCAGCTCGCGCCCCAAATGAAAATATAGCTAAACA

GGTTATTGACCATTTGCGAAATGTATCTAATGGTCAAACTAAATCTACTCGTTCGCA

GAATTGGGAATCAACTGTTATATGGAATGAAACTTCCAGACACCGTACTTTAGTTGC

ATATTTAAAACATGTTGAGCTACAGCATTATATTCAGCAATTAAGCTCTAAGCCATC

CGCAAAAATGACCTCTTATCAAAAGGAGCAATTAAAGGTACTCTCTAATCCTGACCT

GTTGGAGTTTGCTTCCGGTCTGGTTCGCTTTGAAGCTCGAATTAAAACGCGATATTTG

AAGTCTTTCGGGCTTCCTCTTAATCTTTTTGATGCAATCCGCTTTGCTTCTGACTATA

ATAGTCAGGGTAAAGACCTGATTTTTGATTTATGGTCATTCTCGTTTTCTGAACTGTT

TAAAGCATTTGAGGGGGATTCAATGAATATTTATGACGATTCCGCAGTATTGGACGC

TATCCAGTCTAAACATTTTACTATTACCCCCTCTGGCAAAACTTCTTTTGCAAAAGCC

TCTCGCTATTTTGGTTTTTATCGTCGTCTGGTAAACGAGGGTTATGATAGTGTTGCTC

TTACTATGCCTCGTAATTCCTTTTGGCGTTATGTATCTGCATTAGTTGAATGTGGTAT

TCCTAAATCTCAACTGATGAATCTTTCTACCTGTAATAATGTTGTTCCGTTAGTTCGT

TTTATTAACGTAGATTTTTCTTCCCAACGTCCTGACTGGTATAATGAGCCAGTTCTTA

AAATCGCATAAGGTAATTCACAATGATTAAAGTTGAAATTAAACCATCTCAAGCCCA

ATTTACTACTCGTTCTGGTGTTTCTCGTCAGGGCAAGCCTTATTCACTGAATGAGCAG

CTTTGTTACGTTGATTTGGGTAATGAATATCCGGTTCTTGTCAAGATTACTCTTGATG

AAGGTCAGCCAGCCTATGCGCCTGGTCTGTACACCGTTCATCTGTCCTCTTTCAAAGT

TGGTCAGTTCGGTTCCCTTATGATTGACCGTCTGCGCCTCGTTCCGGCTAAGTAACAT

GGAGCAGGTCGCGGATTTCGACACAATTTATCAGGCGATGATACAAATCTCCGTTGT

ACTTTGTTTCGCGCTTGGTATAATCGCTGGGGGTCAAAGATGAGTGTTTTAGTGTATT

CTTTTGCCTCTTTCGTTTTAGGTTGGTGCCTTCGTAGTGGCATTACGTATTTTACCCGT

-continued

TTAATGGAAACTTCCTCATGAAAAAGTCTTTAGTCCTCAAAGCCTCTGTAGCCGTTG

CTACCCTCGTTCCGATGCTGTCTTTCGCTGCTGAGGGTGACGATCCCGCAAAAGCGG

CCTTTAACTCCCTGCAAGCCTCAGCGACCGAATATATCGGTTATGCGTGGGCGATGG

TTGTTGTCATTGTCGGCGCAACTATCGGTATCAAGCTGTTTAAGAAATTCACCTCGA

AAGCAAGCTGATAAACCGATACAATTAAAGGCTCCTTTTGGAGCCTTTTTTTTGGAG

ATTTTCAACGTGAAAAAATTATTATTCGCAATTCCTTTAGTTGTTCCTTTCTATTCTCA

CTCCGCTGAAACTGTTGAAAGTTGTTTAGCAAAATCCCATACAGAAAATTCATTTAC

TAACGTCTGGAAAGACGACAAAACTTTAGATCGTTACGCTAACTATGAGGGCTGTCT

GTGGAATGCTACAGGCGTTGTAGTTTGTACTGGTGACGAAACTCAGTGTTACGGTAC

ATGGGTTCCTATTGGGCTTGCTATCCCTGAAAATGAGGGTGGTGGCTCTGAGGGTGG

CGGTTCTGAGGGTGGCGGTTCTGAGGGTGGCGGTACTAAACCTCCTGAGTACGGTGA

TACACCTATTCCGGGCTATACTTATATCAACCCTCTCGACGGCACTTATCCGCCTGGT

ACTGAGCAAAACCCCGCTAATCCTAATCCTTCTCTTGAGGAGTCTCAGCCTCTTAAT

ACTTTCATGTTTCAGAATAATAGGTTCCGAAATAGGCAGGGGGCATTAACTGTTTAT

ACGGGCACTGTTACTCAAGGCACTGACCCCGTTAAAACTTATTACCAGTACACTCCT

GTATCATCAAAAGCCATGTATGACGCTTACTGGAACGGTAAATTCAGAGACTGCGCT

TTCCATTCTGGCTTTAATGAGGATTTATTTGTTTGTGAATATCAAGGCCAATCGTCTG

ACCTGCCTCAACCTCCTGTCAATGCTGGCGGCGGCTCTGGTGGTGGTTCTGGTGGCG

GCTCTGAGGGTGGTGGCTCTGAGGGTGGCGGTTCTGAGGGTGGCGGCTCTGAGGGA

GGCGGTTCCGGTGGTGGCTCTGGTTCCGGTGATTTTGATTATGAAAAGATGGCAAAC

GCTAATAAGGGGGCTATGACCGAAAATGCCGATGAAAACGCGCTACAGTCTGACGC

TAAAGGCAAACTTGATTCTGTCGCTACTGATTACGGTGCTGCTATCGATGGTTTCATT

GGTGACGTTTCCGGCCTTGCTAATGGTAATGGTGCTACTGGTGATTTTGCTGGCTCTA

ATTCCCAAATGGCTCAAGTCGGTGACGGTGATAATTCACCTTTAATGAATAATTTCC

GTCAATATTTACCTTCCCTCCCTCAATCGGTTGAATGTCGCCCTTTTGTCTTTGGCGC

TGGTAAACCATATGAATTTTCTATTGATTGTGACAAAATAAACTTATTCCGTGGTGTC

TTTGCGTTTCTTTTATATGTTGCCACCTTTATGTATGTATTTTCTACGTTTGCTAACAT

ACTGCGTAATAAGGAGTCTTAATCATGCCAGTTCTTTTGGGTATTCCGTTATTATTGC

GTTTCCTCGGTTTCCTTCTGGTAACTTTGTTCGGCTATCTGCTTACTTTTCTTAAAAAG

GGCTTCGGTAAGATAGCTATTGCTATTTCATTGTTTCTTGCTCTTATTATTGGGCTTA

ACTCAATTCTTGTGGGTTATCTCTCTGATATTAGCGCTCAATTACCCTCTGACTTTGT

TCAGGGTGTTCAGTTAATTCTCCCGTCTAATGCGCTTCCCTGTTTTTATGTTATTCTCT

CTGTAAAGGCTGCTATTTTCATTTTTGACGTTAAACAAAAAATCGTTTCTTATTTGGA

TTGGGATAAATAATATGGCTGTTTATTTTGTAACTGGCAAATTAGGCTCTGGAAAGA

CGCTCGTTAGCGTTGGTAAGATTCAGGATAAAATTGTAGCTGGGTGCAAAATAGCA

ACTAATCTTGATTTAAGGCTTCAAAACCTCCCGCAAGTCGGGAGGTTCGCTAAAACG

CCTCGCGTTCTTAGAATACCGGATAAGCCTTCTATATCTGATTTGCTTGCTATTGGGC

GCGGTAATGATTCCTACGATGAAAATAAAAACGGCTTGCTTGTTCTCGATGAGTGCG

GTACTTGGTTTAATACCCGTTCTTGGAATGATAAGGAAAGACAGCCGATTATTGATT

GGTTTCTACATGCTCGTAAATTAGGATGGGATATTATTTTTCTTGTTCAGGACTTATC

TATTGTTGATAAACAGGCGCGTTCTGCATTAGCTGAACATGTTGTTTATTGTCGTCGT

-continued

```
CTGGACAGAATTACTTTACCTTTTGTCGGTACTTTATATTCTCTTATTACTGGCTCGA

AAATGCCTCTGCCTAAATTACATGTTGGCGTTGTTAAATATGGCGATTCTCAATTAA

GCCCTACTGTTGAGCGTTGGCTTTATACTGGTAAGAATTTGTATAACGCATATGATA

CTAAACAGGCTTTTTCTAGTAATTATGATTCCGGTGTTTATTCTTATTTAACGCCTTA

TTTATCACACGGTCGGTATTTCAAACCATTAAATTTAGGTCAGAAGATGAAATTAAC

TAAAATATATTTGAAAAAGTTTTCTCGCGTTCTTTGTCTTGCGATTGGATTTGCATCA

GCATTTACATATAGTTATATAACCCAACCTAAGCCGGAGGTTAAAAAGGTAGTCTCT

CAGACCTATGATTTTGATAAATTCACTATTGACTCTTCTCAGCGTCTTAATCTAAGCT

ATCGCTATGTTTTCAAGGATTCTAAGGGAAAATTAATTAATAGCGACGATTTACAGA

AGCAAGGTTATTCACTCACATATATTGATTTATGTACTGTTTCCATTAAAAAAGGTA

ATTCAAATGAAATTGTTAAATGTAATTAATTTTGTTTTCTTGATGTTTGTTTCATCATC

TTCTTTTGCTCAGGTAATTGAAATGAATAATTCGCCTCTGCGCGATTTTGTAACTTGG

TATTCAAAGCAATCAGGCGAATCCGTTATTGTTTCTCCCGATGTAAAAGGTACTGTT

ACTGTATATTCATCTGACGTTAAACCTGAAAATCTACGCAATTTCTTTATTTCTGTTT

TACGTGCAAATAATTTTGATATGGTAGGTTCTAACCCTTCCATTATTCAGAAGTATA

ATCCAAACAATCAGGATTATATTGATGAATTGCCATCATCTGATAATCAGGAATATG

ATGATAATTCCGCTCCTTCTGGTGGTTTCTTTGTTCCGCAAAATGATAATGTTACTCA

AACTTTTAAAATTAATAACGTTCGGGCAAAGGATTTAATACGAGTTGTCGAATTGTT

TGTAAAGTCTAATACTTCTAAATCCTCAAATGTATTATCTATTGACGGCTCTAATCTA

TTAGTTGTTAGTGCTCCTAAAGATATTTTAGATAACCTTCCTCAATTCCTTTCAACTG

TTGATTTGCCAACTGACCAGATATTGATTGAGGGTTTGATATTTGAGGTTCAGCAAG

GTGATGCTTTAGATTTTTCATTTGCTGCTGGCTCTCAGCGTGGCACTGTTGCAGGCGG

TGTTAATACTGACCGCCTCACCTCTGTTTTATCTTCTGCTGGTGGTTCGTTCGGTATTT

TTAATGGCGATGTTTTAGGGCTATCAGTTCGCGCATTAAAGACTAATAGCCATTCAA

AAATATTGTCTGTGCCACGTATTCTTACGCTTTCAGGTCAGAAGGGTTCTATCTCTGT

TGGCCAGAATGTCCCTTTTATTACTGGTCGTGTGACTGGTGAATCTGCCAATGTAAA

TAATCCATTTCAGACGATTGAGCGTCAAAATGTAGGTATTTCCATGAGCGTTTTTCCT

GTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCTACAACG

GTTAATTTGCGTGATGGACAGACTCTTTTACTCGGTGGCCTCACTGATTATAAAAAC

ACTTCTCAGGATTCTGGCGTACCGTTCCTGTCTAAAATCCCTTTAATCGGCCTCCTGT

TTAGCTCCCGCTCTGATTCTAACGAGGAAAG
```

A batch of 192 short DNA oligos of equal length were added to make the long, linearized tether double stranded except for a short region on the end opposite the hairpin chain. This single stranded region hybridizes with a connecting strand that captures a biotinylated DNA strand, which binds streptavidin-coated mechanical amplifiers. To assemble the sensors, the hairpin sequences, sequences with a fluorophore, sequences with a quencher, sequences with digoxigenin strand, connecting sandwich strands, cut m13, 192 short m13 complimentary oligos, and biotin strand were mixed together with salted TE buffer. This mixture self-assembles during an overnight annealing protocol in a thermocycler. The samples are electrophoresed in a 1% agarose gel and purified by band excision.

Before adding the mechanical transducer component, the ability of the sensor to fluoresce and quench (by adding complementary DNA strands) were verified with total internal reflection fluorescence (TIRF) microscopy. An oligo complimentary to the entire hairpin was added to one of the samples, which effectively forces all hairpins in each sensor to adopt the "open" configuration. Samples purified from the gel with this added opening strand exhibited fluorescence while samples without the opening strand could thus adopt the "closed" configuration and fluorescence signal was quenched. It is also worth noting that the linearized double strand tether with added open or closed hairpin chains exhibits gel mobility indistinguishable from the linearized dsTether with no hairpins added. This is because the hairpin chain adds only a few hundred base pairs to the 8064 bp long tether. Additionally, the excess hairpins can be visualized in the gel. However, as the samples are purified based on the mobility of the tether band, visible fluorescence in the open hairpin sample indicates that the hairpins are attaching to the dsTether. Hairpin attachment to the glass depends on the designed digoxigenin/anti-digoxigenin chemistry as very few points of fluorescence were visible in the open sensor sample incubated on glass without prior anti-digoxigenin treatment. In such a scenario, any present fluorescence was deemed to be nonspecific attachment to the glass.

Hairpin(sensor) Strands

SEQ ID NO: 1
tctactaaaactctatcacaCCGGAGCGCCTCCGTGTATAAATGTTTTCATTTATACgcgtcaatgtacac gtcttggcaggcatca, SEQ ID NO: 2
tgacgccaagttcgaCCGGAGCGCCTCCGTGTATAAATGTTTTCATTTATACgcgtcaatgtacacgtga tgcctgccaaga, SEQ ID NO: 3
tcgaacttggcgtcaCCGGAGCGCCTCCGTGTATAAATGTTTTCATTTATACgcgtcaatgtacacgcag cgttattcgcga, SEQ ID NO: 4
caatttcgaggaccgCCGGAGCGCCTCCGTGTATAAATGTTTTCATTTATACgcgtcaatgtacacgtcg cgaataacgctg, SEQ ID NO: 5
cggtcctcgaaattgCCGGAGCGCCTCCGTGTATAAATGTTTTCATTTATACgcgtcaatgtacacgggc tctcagcttaag, SEQ ID NO: 6
gtcgtcaccagagatCCGGAGCGCCTCCGTGTATAAATGTTTTCATTTATACgcgtcaatgtacacgctta agctgagagcc, SEQ ID NO: 7
atctctggtgacgacCCGGAGCGCCTCCGTGTATAAATGTTTTCATTTATACgcgtcaatgtacacggcc aagtcgtcattg, SEQ ID NO: 8
aagctacctgcgatgCCGGAGCGCCTCCGTGTATAAATGTTTTCATTTATACgcgtcaatgtacacgcaa tgacgacttggc, SEQ ID NO: 9
catcgcaggtagcttCCGGAGCGCCTCCGTGTATAAATGTTTTCATTTATACgcgtcaatgtacacggac gcacgctttgta, SEQ ID NO: 10
tcctccatcccttccCCGGAGCGCCTCCGTGTATAAATGTTTTCATTTATACgcgtcaatgtacacgtaca aagcgtgcgtc, Sensor to tether connector SEQ ID NO: 11
tgtgatagagttttagtagaCTTTCCTCGTTAGAATCAGAG, Tether to biotin connector SEQ ID NO: 12
GGGCGCGTACTATGGTTGCTTttaggagtgtgggaa, biotin connector SEQ ID NO: 13
/5biosg/ttcccacactcctaa, Sensor to digoxigenin SEQ ID NO: 14
ggaagggatggaggatt/3Dig_N/, Fluorophore SEQ ID NO: 15
/5Alex488N/ACGGAGGCGCTCCGG, -continued Quencher SEQ ID NO: 16
cgtgtacattgacgc/3BHQ_1/, Tether complimentary

SEQ ID NO: 17
CGGGAGCTAAACAGGAGGCCGATTAAAGGGATTTTAGACAGG,

SEQ ID NO: 18
AACGGTACGCCAGAATCCTGAGAAGTGTTTTTATAATCAGTG,

SEQ ID NO: 19
AGGCCACCGAGTAAAAGAGTCTGTCCATCACGCAAATTAACC,

SEQ ID NO: 20
GTTGTAGCAATACTTCTTTGATTAGTAATAACATCACTTGCC,

SEQ ID NO: 21
TGAGTAGAAGAACTCAAACTATCGGCCTTGCTGGTAATATCC,

SEQ ID NO: 22
AGAACAATATTACCGCCAGCCATTGCAACAGGAAAAACGCTC,

SEQ ID NO: 23
ATGGAAATACCTACATTTTGACGCTCAATCGTCTGAAATGGA,

SEQ ID NO: 24
TTATTTACATTGGCAGATTCACCAGTCACACGACCAGTAATA,

SEQ ID NO: 25
AAAGGGACATTCTGGCCAACAGAGATAGAACCCTTCTGACCT,

SEQ ID NO: 26
GAAAGCGTAAGAATACGTGGCACAGACAATATTTTTGAATGG,

SEQ ID NO: 27
CTATTAGTCTTTAATGCGCGAACTGATAGCCCTAAAACATCG,

SEQ ID NO: 28
CCATTAAAAATACCGAACGAACCACCAGCAGAAGATAAAACA,

SEQ ID NO: 29
GAGGTGAGGCGGTCAGTATTAACACCGCCTGCAACAGTGCCA,

SEQ ID NO: 30
CGCTGAGAGCCAGCAGCAAATGAAAAATCTAAAGCATCACCT,

SEQ ID NO: 31
TGCTGAACCTCAAATATCAAACCCTCAATCAATATCTGGTCA,

SEQ ID NO: 32
GTTGGCAAATCAACAGTTGAAAGGAATTGAGGAAGGTTATCT,

SEQ ID NO: 33
AAAATATCTTTAGGAGCACTAACAACTAATAGATTAGAGCCG,

SEQ ID NO: 34
TCAATAGATAATACATTTGAGGATTTAGAAGTATTAGACTTT,

SEQ ID NO: 35
ACAAACAATTCGACAACTCGTATTAAATCCTTTGCCCGAACG,

SEQ ID NO: 36
TTATTAATTTTAAAAGTTTGAGTAACATTATCATTTTGCGGA,

SEQ ID NO: 37
ACAAAGAAACCACCAGAAGGAGCGGAATTATCATCATATTCC,

SEQ ID NO: 38
TGATTATCAGATGATGGCAATTCATCAATATAATCCTGATTG,

SEQ ID NO: 39
TTTGGATTATACTTCTGAATAATGGAAGGGTTAGAACCTACC,

SEQ ID NO: 40
ATATCAAAATTATTTGCACGTAAAACAGAAATAAAGAAATTG,

SEQ ID NO: 41
CGTAGATTTTCAGGTTTAACGTCAGATGAATATACAGTAACA,

-continued

SEQ ID NO: 42
GTACCTTTTACATCGGGAGAAACAATAACGGATTCGCCTGAT,

SEQ ID NO: 43
TGCTTTGAATACCAAGTTACAAAATCGCGCAGAGGCGAATTA,

SEQ ID NO: 44
TTCATTTCAATTACCTGAGCAAAAGAAGATGATGAAACAAAC,

SEQ ID NO: 45
ATCAAGAAAACAAAATTAATTACATTTAACAATTTCATTTGA,

SEQ ID NO: 46
ATTACCTTTTTTAATGGAAACAGTACATAAATCAATATATGT,

SEQ ID NO: 47
GAGTGAATAACCTTGCTTCTGTAAATCGTCGCTATTAATTAA,

SEQ ID NO: 48
TTTTCCCTTAGAATCCTTGAAAACATAGCGATAGCTTAGATT,

SEQ ID NO: 49
AAGACGCTGAGAAGAGTCAATAGTGAATTTATCAAAATCATA,

SEQ ID NO: 50
GGTCTGAGAGACTACCTTTTTAACCTCCGGCTTAGGTTGGGT,

SEQ ID NO: 51
TATATAACTATATGTAAATGCTGATGCAAATCCAATCGCAAG,

SEQ ID NO: 52
ACAAAGAACGCGAGAAAACTTTTTCAAATATATTTTAGTTAA,

SEQ ID NO: 53
TTTCATCTTCTGACCTAAATTTAATGGTTTGAAATACCGACC,

SEQ ID NO: 54
GTGTGATAAATAAGGCGTTAAATAAGAATAAACACCGGAATC,

SEQ ID NO: 55
ATAATTACTAGAAAAAGCCTGTTTAGTATCATATGCGTTATA,

SEQ ID NO: 56
CAAATTCTTACCAGTATAAAGCCAACGCTCAACAGTAGGGCT,

SEQ ID NO: 57
TAATTGAGAATCGCCATATTTAACAACGCCAACATGTAATTT,

SEQ ID NO: 58
AGGCAGAGGCATTTTCGAGCCAGTAATAAGAGAATATAAAGT,

SEQ ID NO: 59
ACCGACAAAAGGTAAAGTAATTCTGTCCAGACGACGACAATA,

SEQ ID NO: 60
AACAACATGTTCAGCTAATGCAGAACGCGCCTGTTTATCAAC,

SEQ ID NO: 61
AATAGATAAGTCCTGAACAAGAAAAATAATATCCCATCCTAA,

SEQ ID NO: 62
TTTACGAGCATGTAGAAACCAATCAATAATCGGCTGTCTTTC,

SEQ ID NO: 63
CTTATCATTCCAAGAACGGGTATTAAACCAAGTACCGCACTC,

SEQ ID NO: 64
ATCGAGAACAAGCAAGCCGTTTTTATTTTCATCGTAGGAATC,

SEQ ID NO: 65
ATTACCGCGCCCAATAGCAAGCAAATCAGATATAGAAGGCTT,

SEQ ID NO: 66
ATCCGGTATTCTAAGAACGCGAGGCGTTTTAGCGAACCTCCC,

SEQ ID NO: 67
GACTTGCGGGAGGTTTTGAAGCCTTAAATCAAGATTAGTTGC,

SEQ ID NO: 68
TATTTTGCACCCAGCTACAATTTTATCCTGAATCTTACCAAC,

-continued

SEQ ID NO: 69
GCTAACGAGCGTCTTTCCAGAGCCTAATTTGCCAGTTACAAA,

SEQ ID NO: 70
ATAAACAGCCATATTATTTATCCCAATCCAAATAAGAAACGA,

SEQ ID NO: 71
TTTTTTGTTTAACGTCAAAAATGAAAATAGCAGCCTTTACAG,

SEQ ID NO: 72
AGAGAATAACATAAAAACAGGGAAGCGCATTAGACGGGAGAA,

SEQ ID NO: 73
TTAACTGAACACCCTGAACAAAGTCAGAGGGTAATTGAGCGC,

SEQ ID NO: 74
TAATATCAGAGAGATAACCCACAAGAATTGAGTTAAGCCCAA,

SEQ ID NO: 75
TAATAAGAGCAAGAAACAATGAAATAGCAATAGCTATCTTAC,

SEQ ID NO: 76
CGAAGCCCTTTTTAAGAAAAGTAAGCAGATAGCCGAACAAAG,

SEQ ID NO: 77
TTACCAGAAGGAAACCGAGGAAACGCAATAATAACGGAATAC,

SEQ ID NO: 78
CCAAAAGAACTGGCATGATTAAGACTCCTTATTACGCAGTAT,

SEQ ID NO: 79
GTTAGCAAACGTAGAAAATACATACATAAAGGTGGCAACATA,

SEQ ID NO: 80
TAAAAGAAACGCAAAGACACCACGGAATAAGTTTATTTTGTC,

SEQ ID NO: 81
ACAATCAATAGAAAATTCATATGGTTTACCAGCGCCAAAGAC,

SEQ ID NO: 82
AAAAGGGCGACATTCAACCGATTGAGGGAGGGAAGGTAAATA,

SEQ ID NO: 83
TTGACGGAAATTATTCATTAAAGGTGAATTATCACCGTCACC,

SEQ ID NO: 84
GACTTGAGCCATTTGGGAATTAGAGCCAGCAAAATCACCAGT,

SEQ ID NO: 85
AGCACCATTACCATTAGCAAGGCCGGAAACGTCACCAATGAA,

SEQ ID NO: 86
ACCATCGATAGCAGCACCGTAATCAGTAGCGACAGAATCAAG,

SEQ ID NO: 87
TTTGCCTTTAGCGTCAGACTGTAGCGCGTTTTCATCGGCATT,

SEQ ID NO: 88
TTCGGTCATAGCCCCCTTATTAGCGTTTGCCATCTTTTCATA,

SEQ ID NO: 89
ATCAAAATCACCGGAACCAGAGCCACCACCGGAACCGCCTCC,

SEQ ID NO: 90
CTCAGAGCCGCCACCCTCAGAACCGCCACCCTCAGAGCCACC,

SEQ ID NO: 91
ACCCTCAGAGCCGCCACCAGAACCACCACCAGAGCCGCCGCC,

SEQ ID NO: 92
AGCATTGACAGGAGGTTGAGGCAGGTCAGACGATTGGCCTTG,

SEQ ID NO: 93
ATATTCACAAACAAATAAATCCTCATTAAAGCCAGAATGGAA,

SEQ ID NO: 94
AGCGCAGTCTCTGAATTTACCGTTCCAGTAAGCGTCATACAT,

SEQ ID NO: 95
GGCTTTTGATGATACAGGAGTGTACTGGTAATAAGTTTTAAC,

-continued

SEQ ID NO: 96
GGGGTCAGTGCCTTGAGTAACAGTGCCCGTATAAACAGTTAA,

SEQ ID NO: 97
TGCCCCCTGCCTATTTCGGAACCTATTATTCTGAAACATGAA,

SEQ ID NO: 98
AGTATTAAGAGGCTGAGACTCCTCAAGAGAAGGATTAGGATT,

SEQ ID NO: 99
AGCGGGGTTTTGCTCAGTACCAGGCGGATAAGTGCCGTCGAG,

SEQ ID NO: 100
AGGGTTGATATAAGTATAGCCCGGAATAGGTGTATCACCGTA,

SEQ ID NO: 101
CTCAGGAGGTTTAGTACCGCCACCCTCAGAACCGCCACCCTC,

SEQ ID NO: 102
AGAACCGCCACCCTCAGAGCCACCACCCTCATTTTCAGGGAT,

SEQ ID NO: 103
AGCAAGCCCAATAGGAACCCATGTACCGTAACACTGAGTTTC,

SEQ ID NO: 104
GTCACCAGTACAAACTACAACGCCTGTAGCATTCCACAGACA,

SEQ ID NO: 105
GCCCTCATAGTTAGCGTAACGATCTAAAGTTTTGTCGTCTTT,

SEQ ID NO: 106
CCAGACGTTAGTAAATGAATTTTCTGTATGGGATTTTGCTAA,

SEQ ID NO: 107
ACAACTTTCAACAGTTTCAGCGGAGTGAGAATAGAAAGGAAC,

SEQ ID NO: 108
AACTAAAGGAATTGCGAATAATAATTTTTTCACGTTGAAAAT,

SEQ ID NO: 109
CTCCAAAAAAAAGGCTCCAAAAGGAGCCTTTAATTGTATCGG,

SEQ ID NO: 110
TTTATCAGCTTGCTTTCGAGGTGAATTTCTTAAACAGCTTGA,

SEQ ID NO: 111
TACCGATAGTTGCGCCGACAATGACAACAACCATCGCCCACG,

SEQ ID NO: 112
CATAACCGATATATTCGGTCGCTGAGGCTTGCAGGGAGTTAA,

SEQ ID NO: 113
AGGCCGCTTTTGCGGGATCGTCACCCTCAGCAGCGAAAGACA,

SEQ ID NO: 114
GCATCGGAACGAGGGTAGCAACGGCTACAGAGGCTTTGAGGA,

SEQ ID NO: 115
CTAAAGACTTTTTCATGAGGAAGTTTCCATTAAACGGGTAAA,

SEQ ID NO: 116
ATACGTAATGCCACTACGAAGGCACCAACCTAAAACGAAAGA,

SEQ ID NO: 117
GGCAAAAGAATACACTAAAACACTCATCTTTGACCCCCAGCG,

SEQ ID NO: 118
ATTATACCAAGCGCGAAACAAAGTACAACGGAGATTTGTATC,

SEQ ID NO: 119
ATCGCCTGATAAATTGTGTCGAAATCCGCGACCTGCTCCATG,

SEQ ID NO: 120
TTACTTAGCCGGAACGAGGCGCAGACGGTCAATCATAAGGGA,

SEQ ID NO: 121
ACCGAACTGACCAACTTTGAAAGAGGACAGATGAACGGTGTA,

SEQ ID NO: 122
CAGACCAGGCGCATAGGCTGGCTGACCTTCATCAAGAGTAAT,

-continued

SEQ ID NO: 123
CTTGACAAGAACCGGATATTCATTACCCAAATCAACGTAACA,

SEQ ID NO: 124
AAGCTGCTCATTCAGTGAATAAGGCTTGCCCTGACGAGAAAC,

SEQ ID NO: 125
ACCAGAACGAGTAGTAAATTGGGCTTGAGATGGTTTAATTTC,

SEQ ID NO: 126
AACTTTAATCATTGTGAATTACCTTATGCGATTTTAAGAACT,

SEQ ID NO: 127
GGCTCATTATACCAGTCAGGACGTTGGGAAGAAAAATCTACG,

SEQ ID NO: 128
TTAATAAAACGAACTAACGGAACAACATTATTACAGGTAGAA,

SEQ ID NO: 129
AGATTCATCAGTTGAGATTTAGGAATACCACATTCAACTAAT,

SEQ ID NO: 130
GCAGATACATAACGCCAAAAGGAATTACGAGGCATAGTAAGA,

SEQ ID NO: 131
GCAACACTATCATAACCCTCGTTTACCAGACGACGATAAAAA,

SEQ ID NO: 132
CCAAAATAGCGAGAGGCTTTTGCAAAAGAAGTTTTGCCAGAG,

SEQ ID NO: 133
GGGGTAATAGTAAAATGTTTAGACTGGATAGCGTCCAATACT,

SEQ ID NO: 134
GCGGAATCGTCATAAATATTCATTGAATCCCCCTCAAATGCT,

SEQ ID NO: 135
TTAAACAGTTCAGAAAACGAGAATGACCATAAATCAAAAATC,

SEQ ID NO: 136
AGGTCTTTACCCTGACTATTATAGTCAGAAGCAAAGCGGATT,

SEQ ID NO: 137
GCATCAAAAAGATTAAGAGGAAGCCCGAAAGACTTCAAATAT,

SEQ ID NO: 138
CGCGTTTTAATTCGAGCTTCAAAGCGAACCAGACCGGAAGCA,

SEQ ID NO: 139
AACTCCAACAGGTCAGGATTAGAGAGTACCTTTAATTGCTCC,

SEQ ID NO: 140
TTTTGATAAGAGGTCATTTTTGCGGATGGCTTAGAGCTTAAT,

SEQ ID NO: 141
TGCTGAATATAATGCTGTAGCTCAACATGTTTTAAATATGCA,

SEQ ID NO: 142
ACTAAAGTACGGTGTCTGGAAGTTTCATTCCATATAACAGTT,

SEQ ID NO: 143
GATTCCCAATTCTGCGAACGAGTAGATTTAGTTTGACCATTA,

SEQ ID NO: 144
GATACATTTCGCAAATGGTCAATAACCTGTTTAGCTATATTT,

SEQ ID NO: 145
TCATTTGGGGCGCGAGCTGAAAAGGTGGCATCAATTCTACTA,

SEQ ID NO: 146
ATAGTAGTAGCATTAACATCCAATAAATCATACAGGCAAGGC,

SEQ ID NO: 147
AAAGAATTAGCAAAATTAAGCAATAAAGCCTCAGAGCATAAA,

SEQ ID NO: 148
GCTAAATCGGTTGTACCAAAAACATTATGACCCTGTAATACT,

SEQ ID NO: 149
TTTGCGGGAGAAGCCTTTATTTCAACGCAAGGATAAAAATTT,

-continued

SEQ ID NO: 150
TTAGAACCCTCATATATTTTAAATGCAATGCCTGAGTAATGT,

SEQ ID NO: 151
GTAGGTAAAGATTCAAAAGGGTGAGAAAGGCCGGAGACAGTC,

SEQ ID NO: 152
AAATCACCATCAATATGATATTCAACCGTTCTAGCTGATAAA,

SEQ ID NO: 153
TTAATGCCGGAGAGGGTAGCTATTTTTGAGAGATCTACAAAG,

SEQ ID NO: 154
GCTATCAGGTCATTGCCTGAGAGTCTGGAGCAAACAAGAGAA,

SEQ ID NO: 155
TCGATGAACGGTAATCGTAAAACTAGCATGTCAATCATATGT,

SEQ ID NO: 156
ACCCCGGTTGATAATCAGAAAAGCCCCAAAAACAGGAAGATT,

SEQ ID NO: 157
GTATAAGCAAATATTTAAATTGTAAACGTTAATATTTTGTTA,

SEQ ID NO: 158
AAATTCGCATTAAATTTTTGTTAAATCAGCTCATTTTTTAAC,

SEQ ID NO: 159
CAATAGGAACGCCATCAAAAATAATTCGCGTCTGGCCTTCCT,

SEQ ID NO: 160
GTAGCCAGCTTTCATCAACATTAAATGTGAGCGAGTAACAAC,

SEQ ID NO: 161
CCGTCGGATTCTCCGTGGGAACAAACGGCGGATTGACCGTAA,

SEQ ID NO: 162
TGGGATAGGTCACGTTGGTGTAGATGGGCGCATCGTAACCGT,

SEQ ID NO: 163
GCATCTGCCAGTTTGAGGGGACGACGACAGTATCGGCCTCAG,

SEQ ID NO: 164
GAAGATCGCACTCCAGCCAGCTTTCCGGCACCGCTTCTGGTG,

SEQ ID NO: 165
CCGGAAACCAGGCAAAGCGCCATTCGCCATTCAGGCTGCGCA,

SEQ ID NO: 166
ACTGTTGGGAAGGGCGATCGGTGCGGGCCTCTTCGCTATTAC,

SEQ ID NO: 167
GCCAGCTGGCGAAAGGGGGATGTGCTGCAAGGCGATTAAGTT,

SEQ ID NO: 168
GGGTAACGCCAGGGTTTTCCCAGTCACGACGTTGTAAAACGA,

SEQ ID NO: 169
CGGCCAGTGCCAAGCTTTCAGAGGTGGAGCCGCCACGGGAAC,

SEQ ID NO: 170
GGATAACCTCACCGGAAACAATCGGCGAAACGTACAGCGCCA,

SEQ ID NO: 171
TGTTTACCAGTCCCGGAATTTGTGAGAGATAGACTTTCTCCG,

SEQ ID NO: 172
TGGTGAAGGGATAGCTCTCACGGAAAAAGAGACGCAGAAACA,

SEQ ID NO: 173
GCGGATCAAACTTAAATTTCTGCTCATTTGCCGCCAGCAGTT,

SEQ ID NO: 174
GGGCGGTTGTGTACATCGACATAAAAAAATCCCGTAAAAAAA,

SEQ ID NO: 175
GCCGCACAGGCGGCCTTTAGTGATGAAGGGTAAAGTTAAACG,

SEQ ID NO: 176
ATGCTGATTGCCGTTCCGGCAAACGCGGTCCGTTTTTTCGTC,

-continued

SEQ ID NO: 177
TCGTCGCTGGCAGCCTCCGGCCAGAGCACATCCTCATAACGG,

SEQ ID NO: 178
AACGTGCCGGACTTGTAGAACGTCAGCGTGGTGCTGGTCTGG,

SEQ ID NO: 179
TCAGCAGCAACCGCAAGAATGCCAACGGCAGCACCGTCGGTG,

SEQ ID NO: 180
GTGCCATCCCACGCAACCAGCTTACGGCTGGAGGTGTCCAGC,

SEQ ID NO: 181
ATCAGCGGGGTCATTGCAGGCGCTTTCGCACTCAATCCGCCG,

SEQ ID NO: 182
GGCGCGGTTGCGGTATGAGCCGGGTCACTGTTGCCCTGCGGC,

SEQ ID NO: 183
TGGTAATGGGTAAAGGTTTCTTTGCTCGTCATAAACATCCCT,

SEQ ID NO: 184
TACACTGGTGTGTTCAGCAAATCGTTAACGGCATCAGATGCC,

SEQ ID NO: 185
GGGTTACCTGCAGCCAGCGGTGCCGGTGCCCCCTGCATCAGA,

SEQ ID NO: 186
CGATCCAGCGCAGTGTCACTGCGCGCCTGTGCACTCTGTGGT,

SEQ ID NO: 187
GCTGCGGCCAGAATGCGGCGGGCCGTTTTCACGGTCATACCG,

SEQ ID NO: 188
GGGGTTTCTGCCAGCACGCGTGCCTGTTCTTCGCGTCCGTGA,

SEQ ID NO: 189
GCCTCCTCACAGTTGAGGATCCCCGGGTACCGAGCTCGAATT,

SEQ ID NO: 190
CGTAATCATGGTCATAGCTGTTTCCTGTGTGAAATTGTTATC,

SEQ ID NO: 191
CGCTCACAATTCCACACAACATACGAGCCGGAAGCATAAAGT,

SEQ ID NO: 192
GTAAAGCCTGGGGTGCCTAATGAGTGAGCTAACTCACATTAA,

SEQ ID NO: 193
TTGCGTTGCGCTCACTGCCCGCTTTCCAGTCGGGAAACCTGT,

SEQ ID NO: 194
CGTGCCAGCTGCATTAATGAATCGGCCAACGCGCGGGGAGAG,

SEQ ID NO: 195
GCGGTTTGCGTATTGGGCGCCAGGGTGGTTTTTCTTTTCACC,

SEQ ID NO: 196
AGTGAGACGGGCAACAGCTGATTGCCCTTCACCGCCTGGCCC,

SEQ ID NO: 197
TGAGAGAGTTGCAGCAAGCGGTCCACGCTGGTTTGCCCCAGC,

SEQ ID NO: 198
AGGCGAAAATCCTGTTTGATGGTGGTTCCGAAATCGGCAAAA,

SEQ ID NO: 199
TCCCTTATAAATCAAAAGAATAGCCCGAGATAGGGTTGAGTG,

SEQ ID NO: 200
TTGTTCCAGTTTGGAACAAGAGTCCACTATTAAAGAACGTGG,

SEQ ID NO: 201
ACTCCAACGTCAAAGGGCGAAAAACCGTCTATCAGGGCGATG,

SEQ ID NO: 202
GCCCACTACGTGAACCATCACCCAAATCAAGTTTTTTGGGGT,

SEQ ID NO: 203
CGAGGTGCCGTAAAGCACTAAATCGGAACCCTAAAGGGAGCC,

-continued

SEQ ID NO: 204
CCCGATTTAGAGCTTGACGGGGAAAGCCGGCGAACGTGGCGA,

SEQ ID NO: 205
GAAAGGAAGGGAAGAAAGCGAAAGGAGCGGGCGCTAGGGCGC,

SEQ ID NO: 206
TGGCAAGTGTAGCGGTCACGCTGCGCGTAACCACCACACCCG,

SEQ ID NO: 207
CCGCGCTTAATGCGCCGCTACA,

Dendrimer prebackbone

SEQ ID NO: 208
aatcctccatcccttccttaatcctccatcccttccttaatcctccatcccttccttTAGTGGAGATAATGGATTGG, Backbone SEQ ID NO: 209
ggaagggatggaggattgatctactatagcactgcttgatctactatagcactgcttgatctactatagcactgc, Layer 1

SEQ ID NO: 210
tacgtgcttttacaggtgtttacgtgcttttacaggtgtttacgtgcttttacaggtgttGCAGTGCTATAGTAGATC, Layer 2

SEQ ID NO: 211
CACCTGTAAAAGCACGTAttgagcctacttagttgtacttgagcctacttagttgtacttgagcctacttagttgtac, Layer 3

SEQ ID NO: 212
tctatgctactgactaggtttctatgctactgactaggtttctatgctactgactaggttGTACAACTAAGTAGGCTC, Layer 4f SEQ ID NO: 213
CCTAGTCAGTAGCATAGAttCCAATCCATTATCTCCACTACCAATCCATTATCTCCACT
ACCAATCCATTATCTCCACTA, Tether dendrimer grabber SEQ ID NO: 214
CGGGAGCTAAACAGGAGGCCGATTAAAGGGATTTTAGACAGGttCCAATCCATTATC
TCCACTA, SEQ ID NO: 215
AACGGTACGCCAGAATCCTGAGAAGTGTTTTTATAATCAGTGttCCAATCCATTATCT
CCACTA, SEQ ID NO: 216
AGGCCACCGAGTAAAAGAGTCTGTCCATCACGCAAATTAACCttCCAATCCATTATCT
CCACTA, SEQ ID NO: 217
GTTGTAGCAATACTTCTTTGATTAGTAATAACATCACTTGCCttCCAATCCATTATCTC
CACTA, SEQ ID NO: 218
TGAGTAGAAGAACTCAAACTATCGGCCTTGCTGGTAATATCCttCCAATCCATTATCT
CCACTA, SEQ ID NO: 219
AGAACAATATTACCGCCAGCCATTGCAACAGGAAAAACGCTCttCCAATCCATTATCT
CCACTA, SEQ ID NO: 220
ATGGAAATACCTACATTTTGACGCTCAATCGTCTGAAATGGAttCCAATCCATTATCT
CCACTA, SEQ ID NO: 221
TTATTTACATTGGCAGATTCACCAGTCACACGACCAGTAATAttCCAATCCATTATCTC
CACTA, -continued SEQ ID NO: 222
AAAGGGACATTCTGGCCAACAGAGATAGAACCCTTCTGACCTttCCAATCCATTATCT
CCACTA, SEQ ID NO: 223
GAAAGCGTAAGAATACGTGGCACAGACAATATTTTTGAATGGttCCAATCCATTATCT
CCACTA, SEQ ID NO: 224
CTATTAGTCTTTAATGCGCGAACTGATAGCCCTAAAACATCGttCCAATCCATTATCTC
CACTA, SEQ ID NO: 225
CCATTAAAAATACCGAACGAACCACCAGCAGAAGATAAAACAttCCAATCCATTATC
TCCACTA, SEQ ID NO: 226
GAGGTGAGGCGGTCAGTATTAACACCGCCTGCAACAGTGCCAttCCAATCCATTATCT
CCACTA, SEQ ID NO: 227
CGCTGAGAGCCAGCAGCAAATGAAAAATCTAAAGCATCACCTttCCAATCCATTATCT
CCACTA, SEQ ID NO: 228
TGCTGAACCTCAAATATCAAACCCTCAATCAATATCTGGTCAttCCAATCCATTATCTC
CACTA, SEQ ID NO: 229
GTTGGCAAATCAACAGTTGAAAGGAATTGAGGAAGGTTATCTttCCAATCCATTATCT
CCACTA, SEQ ID NO: 230
AAAATATCTTTAGGAGCACTAACAACTAATAGATTAGAGCCGttCCAATCCATTATCT
CCACTA, SEQ ID NO: 231
TCAATAGATAATACATTTGAGGATTTAGAAGTATTAGACTTTttCCAATCCATTATCTC
CACTA, SEQ ID NO: 232
ACAAACAATTCGACAACTCGTATTAAATCCTTTGCCCGAACGttCCAATCCATTATCT
CCACTA, SEQ ID NO: 233
TTATTAATTTTAAAAGTTTGAGTAACATTATCATTTTGCGGAttCCAATCCATTATCTC
CACTA, SEQ ID NO: 234
ACAAAGAAACCACCAGAAGGAGCGGAATTATCATCATATTCCttCCAATCCATTATCT
CCACTA, SEQ ID NO: 235
TGATTATCAGATGATGGCAATTCATCAATATAATCCTGATTGttCCAATCCATTATCTC
CACTA, SEQ ID NO: 236
TTTGGATTATACTTCTGAATAATGGAAGGGTTAGAACCTACCttCCAATCCATTATCTC
CACTA, SEQ ID NO: 237
ATATCAAAATTATTTGCACGTAAAACAGAAATAAAGAAATTGttCCAATCCATTATCT
CCACTA, -continued SEQ ID NO: 238
CGTAGATTTTCAGGTTTAACGTCAGATGAATATACAGTAACAttCCAATCCATTATCT
CCACTA, SEQ ID NO: 239
GTACCTTTTACATCGGGAGAAACAATAACGGATTCGCCTGATttCCAATCCATTATCT
CCACTA, SEQ ID NO: 240
TGCTTTGAATACCAAGTTACAAAATCGCGCAGAGGCGAATTAttCCAATCCATTATCT
CCACTA, SEQ ID NO: 241
TTCATTTCAATTACCTGAGCAAAAGAAGATGATGAAACAAACttCCAATCCATTATCT
CCACTA, SEQ ID NO: 242
ATCAAGAAAACAAAATTAATTACATTTAACAATTTCATTTGAttCCAATCCATTATCTC
CACTA, SEQ ID NO: 243
ATTACCTTTTTTAATGGAAACAGTACATAAATCAATATATGTttCCAATCCATTATCTC
CACTA, SEQ ID NO: 244
GAGTGAATAACCTTGCTTCTGTAAATCGTCGCTATTAATTAAttCCAATCCATTATCTC
CACTA, SEQ ID NO: 245
TTTTCCCTTAGAATCCTTGAAAACATAGCGATAGCTTAGATTttCCAATCCATTATCTC
CACTA, SEQ ID NO: 246
AAGACGCTGAGAAGAGTCAATAGTGAATTTATCAAAATCATAttCCAATCCATTATCT
CCACTA, SEQ ID NO: 247
GGTCTGAGAGACTACCTTTTTAACCTCCGGCTTAGGTTGGGTttCCAATCCATTATCTC
CACTA, SEQ ID NO: 248
TATATAACTATATGTAAATGCTGATGCAAATCCAATCGCAAGttCCAATCCATTATCT
CCACTA, SEQ ID NO: 249
ACAAAGAACGCGAGAAAACTTTTTCAAATATATTTTAGTTAAttCCAATCCATTATCT
CCACTA, SEQ ID NO: 250
TTTCATCTTCTGACCTAAATTTAATGGTTTGAAATACCGACCttCCAATCCATTATCTC
CACTA, SEQ ID NO: 251
GTGTGATAAATAAGGCGTTAAATAAGAATAAACACCGGAATCttCCAATCCATTATCT
CCACTA, SEQ ID NO: 252
ATAATTACTAGAAAAAGCCTGTTTAGTATCATATGCGTTATAttCCAATCCATTATCTC
CACTA, SEQ ID NO: 253
CAAATTCTTACCAGTATAAAGCCAACGCTCAACAGTAGGGCTttCCAATCCATTATCT
CCACTA, -continued SEQ ID NO: 254
TAATTGAGAATCGCCATATTTAACAACGCCAACATGTAATTTttCCAATCCATTATCTC
CACTA, SEQ ID NO: 255
AGGCAGAGGCATTTTCGAGCCAGTAATAAGAGAATATAAAGTttCCAATCCATTATCT
CCACTA, SEQ ID NO: 256
ACCGACAAAAGGTAAAGTAATTCTGTCCAGACGACGACAATAttCCAATCCATTATCT
CCACTA, SEQ ID NO: 257
AACAACATGTTCAGCTAATGCAGAACGCGCCTGTTTATCAACttCCAATCCATTATCT
CCACTA, SEQ ID NO: 258
AATAGATAAGTCCTGAACAAGAAAAATAATATCCCATCCTAAttCCAATCCATTATCT
CCACTA, SEQ ID NO: 259
TTTACGAGCATGTAGAAACCAATCAATAATCGGCTGTCTTTCttCCAATCCATTATCTC
CACTA, SEQ ID NO: 260
CTTATCATTCCAAGAACGGGTATTAAACCAAGTACCGCACTCttCCAATCCATTATCT
CCACTA, SEQ ID NO: 261
ATCGAGAACAAGCAAGCCGTTTTTATTTTCATCGTAGGAATCttCCAATCCATTATCTC
CACTA, SEQ ID NO: 262
ATTACCGCGCCCAATAGCAAGCAAATCAGATATAGAAGGCTTttCCAATCCATTATCT
CCACTA, SEQ ID NO: 263
ATCCGGTATTCTAAGAACGCGAGGCGTTTTAGCGAACCTCCCttCCAATCCATTATCT
CCACTA, SEQ ID NO: 264
GACTTGCGGGAGGTTTTGAAGCCTTAAATCAAGATTAGTTGCttCCAATCCATTATCT
CCACTA, SEQ ID NO: 265
TATTTTGCACCCAGCTACAATTTTATCCTGAATCTTACCAACttCCAATCCATTATCTC
CACTA, SEQ ID NO: 266
GCTAACGAGCGTCTTTCCAGAGCCTAATTTGCCAGTTACAAAttCCAATCCATTATCTC
CACTA, SEQ ID NO: 267
ATAAACAGCCATATTATTTATCCCAATCCAAATAAGAAACGAttCCAATCCATTATCT
CCACTA, SEQ ID NO: 268
TTTTTTGTTTAACGTCAAAAATGAAAATAGCAGCCTTTACAGttCCAATCCATTATCTC
CACTA, SEQ ID NO: 269
AGAGAATAACATAAAAACAGGGAAGCGCATTAGACGGGAGAAttCCAATCCATTATC
TCCACTA, -continued SEQ ID NO: 270
TTAACTGAACACCCTGAACAAAGTCAGAGGGTAATTGAGCGCttCCAATCCATTATCT
CCACTA, SEQ ID NO: 271
TAATATCAGAGAGATAACCCACAAGAATTGAGTTAAGCCCAAttCCAATCCATTATCT
CCACTA, SEQ ID NO: 272
TAATAAGAGCAAGAAACAATGAAATAGCAATAGCTATCTTACttCCAATCCATTATCT
CCACTA, SEQ ID NO: 273
CGAAGCCCTTTTTAAGAAAAGTAAGCAGATAGCCGAACAAAGttCCAATCCATTATCT
CCACTA, SEQ ID NO: 274
TTACCAGAAGGAAACCGAGGAAACGCAATAATAACGGAATACttCCAATCCATTATC
TCCACTA, SEQ ID NO: 275
CCAAAAGAACTGGCATGATTAAGACTCCTTATTACGCAGTATttCCAATCCATTATCT
CCACTA, SEQ ID NO: 276
GTTAGCAAACGTAGAAAATACATACATAAAGGTGGCAACATAttCCAATCCATTATCT
CCACTA, SEQ ID NO: 277
TAAAAGAAACGCAAAGACACCACGGAATAAGTTTATTTTGTCttCCAATCCATTATCT
CCACTA, SEQ ID NO: 278
ACAATCAATAGAAAATTCATATGGTTTACCAGCGCCAAAGACttCCAATCCATTATCT
CCACTA, SEQ ID NO: 279
AAAAGGGCGACATTCAACCGATTGAGGGAGGGAAGGTAAATAttCCAATCCATTATC
TCCACTA, SEQ ID NO: 280
TTGACGGAAATTATTCATTAAAGGTGAATTATCACCGTCACCttCCAATCCATTATCTC
CACTA, SEQ ID NO: 281
GACTTGAGCCATTTGGGAATTAGAGCCAGCAAAATCACCAGTttCCAATCCATTATCT
CCACTA, SEQ ID NO: 282
AGCACCATTACCATTAGCAAGGCCGGAAACGTCACCAATGAAttCCAATCCATTATCT
CCACTA, SEQ ID NO: 283
ACCATCGATAGCAGCACCGTAATCAGTAGCGACAGAATCAAGttCCAATCCATTATCT
CCACTA, SEQ ID NO: 284
TTTGCCTTTAGCGTCAGACTGTAGCGCGTTTTCATCGGCATTttCCAATCCATTATCTC
CACTA, SEQ ID NO: 285
TTCGGTCATAGCCCCCTTATTAGCGTTTGCCATCTTTTCATAttCCAATCCATTATCTCC
ACTA, -continued SEQ ID NO: 286
ATCAAAATCACCGGAACCAGAGCCACCACCGGAACCGCCTCCttCCAATCCATTATCT
CCACTA, SEQ ID NO: 287
CTCAGAGCCGCCACCCTCAGAACCGCCACCCTCAGAGCCACCttCCAATCCATTATCT
CCACTA, SEQ ID NO: 288
ACCCTCAGAGCCGCCACCAGAACCACCACCAGAGCCGCCGCCttCCAATCCATTATCT
CCACTA, SEQ ID NO: 289
AGCATTGACAGGAGGTTGAGGCAGGTCAGACGATTGGCCTTGttCCAATCCATTATCT
CCACTA, SEQ ID NO: 290
ATATTCACAAACAAATAAATCCTCATTAAAGCCAGAATGGAAttCCAATCCATTATCT
CCACTA, SEQ ID NO: 291
AGCGCAGTCTCTGAATTTACCGTTCCAGTAAGCGTCATACATttCCAATCCATTATCTC
CACTA, SEQ ID NO: 292
GGCTTTTGATGATACAGGAGTGTACTGGTAATAAGTTTTAACttCCAATCCATTATCTC
CACTA, SEQ ID NO: 293
GGGGTCAGTGCCTTGAGTAACAGTGCCCGTATAAACAGTTAAttCCAATCCATTATCT
CCACTA, SEQ ID NO: 294
TGCCCCCTGCCTATTTCGGAACCTATTATTCTGAAACATGAAttCCAATCCATTATCTC
CACTA, SEQ ID NO: 295
AGTATTAAGAGGCTGAGACTCCTCAAGAGAAGGATTAGGATTttCCAATCCATTATCT
CCACTA, SEQ ID NO: 296
AGCGGGGTTTTGCTCAGTACCAGGCGGATAAGTGCCGTCGAGttCCAATCCATTATCT
CCACTA, SEQ ID NO: 297
AGGGTTGATATAAGTATAGCCCGGAATAGGTGTATCACCGTAttCCAATCCATTATCT
CCACTA, SEQ ID NO: 298
CTCAGGAGGTTTAGTACCGCCACCCTCAGAACCGCCACCCTCttCCAATCCATTATCT
CCACTA, SEQ ID NO: 299
AGAACCGCCACCCTCAGAGCCACCACCCTCATTTTCAGGGATttCCAATCCATTATCT
CCACTA, SEQ ID NO: 300
AGCAAGCCCAATAGGAACCCATGTACCGTAACACTGAGTTTCttCCAATCCATTATCT
CCACTA, SEQ ID NO: 301
GTCACCAGTACAAACTACAACGCCTGTAGCATTCCACAGACAttCCAATCCATTATCT
CCACTA, -continued SEQ ID NO: 302
GCCCTCATAGTTAGCGTAACGATCTAAAGTTTTGTCGTCTTTttCCAATCCATTATCTC
CACTA, SEQ ID NO: 303
CCAGACGTTAGTAAATGAATTTTCTGTATGGGATTTTGCTAAttCCAATCCATTATCTC
CACTA, SEQ ID NO: 304
ACAACTTTCAACAGTTTCAGCGGAGTGAGAATAGAAAGGAACttCCAATCCATTATCT
CCACTA, SEQ ID NO: 305
AACTAAAGGAATTGCGAATAATAATTTTTTCACGTTGAAAATttCCAATCCATTATCT
CCACTA, SEQ ID NO: 306
CTCCAAAAAAAAGGCTCCAAAAGGAGCCTTTAATTGTATCGGttCCAATCCATTATCT
CCACTA, SEQ ID NO: 307
TTTATCAGCTTGCTTTCGAGGTGAATTTCTTAAACAGCTTGAttCCAATCCATTATCTC
CACTA, SEQ ID NO: 308
TACCGATAGTTGCGCCGACAATGACAACAACCATCGCCCACGttCCAATCCATTATCT
CCACTA, SEQ ID NO: 309
CATAACCGATATATTCGGTCGCTGAGGCTTGCAGGGAGTTAAttCCAATCCATTATCT
CCACTA, SEQ ID NO: 310
AGGCCGCTTTTGCGGGATCGTCACCCTCAGCAGCGAAAGACAttCCAATCCATTATCT
CCACTA, SEQ ID NO: 311
GCATCGGAACGAGGGTAGCAACGGCTACAGAGGCTTTGAGGAttCCAATCCATTATC
TCCACTA, SEQ ID NO: 312
CTAAAGACTTTTTCATGAGGAAGTTTCCATTAAACGGGTAAAttCCAATCCATTATCT
CCACTA, SEQ ID NO: 313
ATACGTAATGCCACTACGAAGGCACCAACCTAAAACGAAAGAttCCAATCCATTATC
TCCACTA, SEQ ID NO: 314
GGCAAAAGAATACACTAAAACACTCATCTTTGACCCCCAGCGttCCAATCCATTATCT
CCACTA, SEQ ID NO: 315
ATTATACCAAGCGCGAAACAAAGTACAACGGAGATTTGTATCttCCAATCCATTATCT
CCACTA, SEQ ID NO: 316
ATCGCCTGATAAATTGTGTCGAAATCCGCGACCTGCTCCATGttCCAATCCATTATCTC
CACTA, SEQ ID NO: 317
TTACTTAGCCGGAACGAGGCGCAGACGGTCAATCATAAGGGAttCCAATCCATTATCT
CCACTA, -continued SEQ ID NO: 318
ACCGAACTGACCAACTTTGAAAGAGGACAGATGAACGGTGTAttCCAATCCATTATCT
CCACTA, SEQ ID NO: 319
CAGACCAGGCGCATAGGCTGGCTGACCTTCATCAAGAGTAATttCCAATCCATTATCT
CCACTA, SEQ ID NO: 320
CTTGACAAGAACCGGATATTCATTACCCAAATCAACGTAACAttCCAATCCATTATCT
CCACTA, SEQ ID NO: 321
AAGCTGCTCATTCAGTGAATAAGGCTTGCCCTGACGAGAAACttCCAATCCATTATCT
CCACTA, SEQ ID NO: 322
ACCAGAACGAGTAGTAAATTGGGCTTGAGATGGTTTAATTTCttCCAATCCATTATCT
CCACTA, SEQ ID NO: 323
AACTTTAATCATTGTGAATTACCTTATGCGATTTTAAGAACTttCCAATCCATTATCTC
CACTA, SEQ ID NO: 324
GGCTCATTATACCAGTCAGGACGTTGGGAAGAAAAATCTACGttCCAATCCATTATCT
CCACTA, SEQ ID NO: 325
TTAATAAAACGAACTAACGGAACAACATTATTACAGGTAGAAttCCAATCCATTATCT
CCACTA, SEQ ID NO: 326
AGATTCATCAGTTGAGATTTAGGAATACCACATTCAACTAATttCCAATCCATTATCTC
CACTA, SEQ ID NO: 327
GCAGATACATAACGCCAAAAGGAATTACGAGGCATAGTAAGAttCCAATCCATTATC
TCCACTA, SEQ ID NO: 328
GCAACACTATCATAACCCTCGTTTACCAGACGACGATAAAAAttCCAATCCATTATCT
CCACTA, SEQ ID NO: 329
CCAAAATAGCGAGAGGCTTTTGCAAAAGAAGTTTTGCCAGAGttCCAATCCATTATCT
CCACTA, SEQ ID NO: 330
GGGGTAATAGTAAAATGTTTAGACTGGATAGCGTCCAATACTttCCAATCCATTATCT
CCACTA, SEQ ID NO: 331
GCGGAATCGTCATAAATATTCATTGAATCCCCCTCAAATGCTttCCAATCCATTATCTC
CACTA, SEQ ID NO: 332
TTAAACAGTTCAGAAAACGAGAATGACCATAAATCAAAAATCttCCAATCCATTATCT
CCACTA, SEQ ID NO: 333
AGGTCTTTACCCTGACTATTATAGTCAGAAGCAAAGCGGATTttCCAATCCATTATCT
CCACTA, -continued SEQ ID NO: 334
GCATCAAAAAGATTAAGAGGAAGCCCGAAAGACTTCAAATATttCCAATCCATTATCT
CCACTA, SEQ ID NO: 335
CGCGTTTTAATTCGAGCTTCAAAGCGAACCAGACCGGAAGCAttCCAATCCATTATCT
CCACTA, SEQ ID NO: 336
AACTCCAACAGGTCAGGATTAGAGAGTACCTTTAATTGCTCCttCCAATCCATTATCT
CCACTA, SEQ ID NO: 337
TTTTGATAAGAGGTCATTTTTGCGGATGGCTTAGAGCTTAATttCCAATCCATTATCTC
CACTA, SEQ ID NO: 338
TGCTGAATATAATGCTGTAGCTCAACATGTTTTAAATATGCAttCCAATCCATTATCTC
CACTA, SEQ ID NO: 339
ACTAAAGTACGGTGTCTGGAAGTTTCATTCCATATAACAGTTttCCAATCCATTATCTC
CACTA, SEQ ID NO: 340
GATTCCCAATTCTGCGAACGAGTAGATTTAGTTTGACCATTAttCCAATCCATTATCTC
CACTA, SEQ ID NO: 341
GATACATTTCGCAAATGGTCAATAACCTGTTTAGCTATATTTttCCAATCCATTATCTC
CACTA, SEQ ID NO: 342
TCATTTGGGGCGCGAGCTGAAAAGGTGGCATCAATTCTACTAttCCAATCCATTATCT
CCACTA, SEQ ID NO: 343
ATAGTAGTAGCATTAACATCCAATAAATCATACAGGCAAGGCttCCAATCCATTATCT
CCACTA, SEQ ID NO: 344
AAAGAATTAGCAAAATTAAGCAATAAAGCCTCAGAGCATAAAttCCAATCCATTATC
TCCACTA, SEQ ID NO: 345
GCTAAATCGGTTGTACCAAAAACATTATGACCCTGTAATACTttCCAATCCATTATCTC
CACTA, SEQ ID NO: 346
TTTGCGGGAGAAGCCTTTATTTCAACGCAAGGATAAAAATTTttCCAATCCATTATCT
CCACTA, SEQ ID NO: 347
TTAGAACCCTCATATATTTTAAATGCAATGCCTGAGTAATGTttCCAATCCATTATCTC
CACTA, SEQ ID NO: 348
GTAGGTAAAGATTCAAAAGGGTGAGAAAGGCCGGAGACAGTCttCCAATCCATTATC
TCCACTA, SEQ ID NO: 349
AAATCACCATCAATATGATATTCAACCGTTCTAGCTGATAAAttCCAATCCATTATCTC
CACTA, -continued SEQ ID NO: 350
TTAATGCCGGAGAGGGTAGCTATTTTTGAGAGATCTACAAAGttCCAATCCATTATCT
CCACTA, SEQ ID NO: 351
GCTATCAGGTCATTGCCTGAGAGTCTGGAGCAAACAAGAGAAttCCAATCCATTATCT
CCACTA, SEQ ID NO: 352
TCGATGAACGGTAATCGTAAAACTAGCATGTCAATCATATGTttCCAATCCATTATCT
CCACTA, SEQ ID NO: 353
ACCCCGGTTGATAATCAGAAAAGCCCCAAAAACAGGAAGATTtCCAATCCATTATCT
CCACTA, SEQ ID NO: 354
GTATAAGCAAATATTTAAATTGTAAACGTTAATATTTTGTTAttCCAATCCATTATCTC
CACTA, SEQ ID NO: 355
AAATTCGCATTAAATTTTTGTTAAATCAGCTCATTTTTTAACttCCAATCCATTATCTC
CACTA, SEQ ID NO: 356
CAATAGGAACGCCATCAAAAATAATTCGCGTCTGGCCTTCCTttCCAATCCATTATCT
CCACTA, SEQ ID NO: 357
GTAGCCAGCTTTCATCAACATTAAATGTGAGCGAGTAACAACttCCAATCCATTATCT
CCACTA, SEQ ID NO: 358
CCGTCGGATTCTCCGTGGGAACAAACGGCGGATTGACCGTAAttCCAATCCATTATCT
CCACTA, SEQ ID NO: 359
TGGGATAGGTCACGTTGGTGTAGATGGGCGCATCGTAACCGTttCCAATCCATTATCT
CCACTA, SEQ ID NO: 360
GCATCTGCCAGTTTGAGGGGACGACGACAGTATCGGCCTCAGttCCAATCCATTATCT
CCACTA, SEQ ID NO: 361
GAAGATCGCACTCCAGCCAGCTTTCCGGCACCGCTTCTGGTGttCCAATCCATTATCT
CCACTA, SEQ ID NO: 362
CCGGAAACCAGGCAAAGCGCCATTCGCCATTCAGGCTGCGCAttCCAATCCATTATCT
CCACTA, SEQ ID NO: 363
ACTGTTGGGAAGGGCGATCGGTGCGGGCCTCTTCGCTATTACttCCAATCCATTATCT
CCACTA, SEQ ID NO: 364
GCCAGCTGGCGAAAGGGGGATGTGCTGCAAGGCGATTAAGTTtCCAATCCATTATCT
CCACTA, SEQ ID NO: 365
GGGTAACGCCAGGGTTTTCCCAGTCACGACGTTGTAAAACGAttCCAATCCATTATCT
CCACTA, -continued SEQ ID NO: 366
CGGCCAGTGCCAAGCTTTCAGAGGTGGAGCCGCCACGGGAACttCCAATCCATTATCT
CCACTA, SEQ ID NO: 367
GGATAACCTCACCGGAAACAATCGGCGAAACGTACAGCGCCAttCCAATCCATTATC
TCCACTA, SEQ ID NO: 368
TGTTTACCAGTCCCGGAATTTGTGAGAGATAGACTTTCTCCGttCCAATCCATTATCTC
CACTA, SEQ ID NO: 369
TGGTGAAGGGATAGCTCTCACGGAAAAAGAGACGCAGAAACAttCCAATCCATTATC
TCCACTA, SEQ ID NO: 370
GCGGATCAAACTTAAATTTCTGCTCATTTGCCGCCAGCAGTTttCCAATCCATTATCTC
CACTA, SEQ ID NO: 371
GGGCGGTTGTGTACATCGACATAAAAAAATCCCGTAAAAAAAttCCAATCCATTATCT
CCACTA, SEQ ID NO: 372
GCCGCACAGGCGGCCTTTAGTGATGAAGGGTAAAGTTAAACGttCCAATCCATTATCT
CCACTA, SEQ ID NO: 373
ATGCTGATTGCCGTTCCGGCAAACGCGGTCCGTTTTTTCGTCttCCAATCCATTATCTC
CACTA, SEQ ID NO: 374
TCGTCGCTGGCAGCCTCCGGCCAGAGCACATCCTCATAACGGttCCAATCCATTATCT
CCACTA, SEQ ID NO: 375
AACGTGCCGGACTTGTAGAACGTCAGCGTGGTGCTGGTCTGGttCCAATCCATTATCT
CCACTA, SEQ ID NO: 376
TCAGCAGCAACCGCAAGAATGCCAACGGCAGCACCGTCGGTGttCCAATCCATTATCT
CCACTA, SEQ ID NO: 377
GTGCCATCCCACGCAACCAGCTTACGGCTGGAGGTGTCCAGCttCCAATCCATTATCT
CCACTA, SEQ ID NO: 378
ATCAGCGGGGTCATTGCAGGCGCTTTCGCACTCAATCCGCCGttCCAATCCATTATCT
CCACTA, SEQ ID NO: 379
GGCGCGGTTGCGGTATGAGCCGGGTCACTGTTGCCCTGCGGCttCCAATCCATTATCT
CCACTA, SEQ ID NO: 380
TGGTAATGGGTAAAGGTTTCTTTGCTCGTCATAAACATCCCTttCCAATCCATTATCTC
CACTA, SEQ ID NO: 381
TACACTGGTGTGTTCAGCAAATCGTTAACGGCATCAGATGCCttCCAATCCATTATCT
CCACTA, -continued SEQ ID NO: 382
GGGTTACCTGCAGCCAGCGGTGCCGGTGCCCCCTGCATCAGAttCCAATCCATTATCT
CCACTA, SEQ ID NO: 383
CGATCCAGCGCAGTGTCACTGCGCGCCTGTGCACTCTGTGGTttCCAATCCATTATCTC
CACTA, SEQ ID NO: 384
GCTGCGGCCAGAATGCGGCGGGCCGTTTTCACGGTCATACCGttCCAATCCATTATCT
CCACTA, SEQ ID NO: 385
GGGGTTTCTGCCAGCACGCGTGCCTGTTCTTCGCGTCCGTGAttCCAATCCATTATCTC
CACTA, SEQ ID NO: 386
GCCTCCTCACAGTTGAGGATCCCCGGGTACCGAGCTCGAATTttCCAATCCATTATCT
CCACTA, SEQ ID NO: 387
CGTAATCATGGTCATAGCTGTTTCCTGTGTGAAATTGTTATCttCCAATCCATTATCTC
CACTA, SEQ ID NO: 388
CGCTCACAATTCCACACAACATACGAGCCGGAAGCATAAAGTttCCAATCCATTATCT
CCACTA, SEQ ID NO: 389
GTAAAGCCTGGGGTGCCTAATGAGTGAGCTAACTCACATTAAttCCAATCCATTATCT
CCACTA, SEQ ID NO: 390
TTGCGTTGCGCTCACTGCCCGCTTTCCAGTCGGGAAACCTGTttCCAATCCATTATCTC
CACTA, SEQ ID NO: 391
CGTGCCAGCTGCATTAATGAATCGGCCAACGCGCGGGGAGAGttCCAATCCATTATCT
CCACTA, SEQ ID NO: 392
GCGGTTTGCGTATTGGGCGCCAGGGTGGTTTTTCTTTTCACCttCCAATCCATTATCTC
CACTA, SEQ ID NO: 393
AGTGAGACGGGCAACAGCTGATTGCCCTTCACCGCCTGGCCCttCCAATCCATTATCT
CCACTA, SEQ ID NO: 394
TGAGAGAGTTGCAGCAAGCGGTCCACGCTGGTTTGCCCCAGCttCCAATCCATTATCT
CCACTA, SEQ ID NO: 395
AGGCGAAAATCCTGTTTGATGGTGGTTCCGAAATCGGCAAAAttCCAATCCATTATCT
CCACTA, SEQ ID NO: 396
TCCCTTATAAATCAAAAGAATAGCCCGAGATAGGGTTGAGTGttCCAATCCATTATCT
CCACTA, SEQ ID NO: 397
TTGTTCCAGTTTGGAACAAGAGTCCACTATTAAAGAACGTGGttCCAATCCATTATCT
CCACTA, -continued SEQ ID NO: 398
ACTCCAACGTCAAAGGGCGAAAAACCGTCTATCAGGGCGATGttCCAATCCATTATCT
CCACTA, SEQ ID NO: 399
GCCCACTACGTGAACCATCACCCAAATCAAGTTTTTTGGGGTttCCAATCCATTATCTC
CACTA, SEQ ID NO: 400
CGAGGTGCCGTAAAGCACTAAATCGGAACCCTAAAGGGAGCCttCCAATCCATTATC
TCCACTA, SEQ ID NO: 401
CCCGATTTAGAGCTTGACGGGGAAAGCCGGCGAACGTGGCGAttCCAATCCATTATCT
CCACTA, SEQ ID NO: 402
GAAAGGAAGGGAAGAAAGCGAAAGGAGCGGGCGCTAGGGCGCttCCAATCCATTAT
CTCCACTA, SEQ ID NO: 403
TGGCAAGTGTAGCGGTCACGCTGCGCGTAACCACCACACCCGttCCAATCCATTATCT
CCACTA, SEQ ID NO: 404
CCGCGCTTAATGCGCCGCTACAttCCAATCCATTATCTCCACTA, SEQ ID NO: 405
GGGCGCGTACTATGGTTGCTTtgacgagcac, Testing of Nanoreporter Following adequate demonstration that the hairpins and tethers were assembling and anchoring to the glass as designed, to assemble the full nanoreporter with the mechanical amplifier was attempted. Addition of the mechanical amplifier would allow for generation of tension in the dsTether and hairpin chain to assess if the hairpins could be opened by addition of shear flow. To test this, a simple microfluidic device was used, consisting of 2mm×25mm×100 μm PDMS channels attached to a #1.5 cover glass. The microfluidics were incubated with 50 μg/mL anti-digoxigenin for 3 minutes, then washed and blocked with a 1% BSA PBS buffer with Tween-20. The purified hairpin-tethers were incubated for one hour with streptavidin coated silica microbeads washed 3× with 1% BSA PBS buffer+Tween-20. Silica proved to be an optimal bead material due to its low autofluorescence as compared to magnetic or polystyrene beads. Following a 30-minute incubation of the prepared hairpin-tether-bead nanoreporters, the microfluidics were ready for flow and imaging. A syringe pump with PBS was hooked up and connected to the microfluidic with friction fit tubing. By applying gradually increasing shear, the hairpins began opening at 15 dynes/$cm^2$ and gradually increased in fluorescence intensity until about 25 dynes/$cm^2$ was applied for a bead size of 1 micron in diameter. Further increase in applied shear did not result in increased fluorescence, indicating that all 10 hairpins were opened in equilibrium. Following removal of shear, fluorescence signal likewise promptly disappeared. This process was repeated many tens of times, or until the fluorophores bleached.

Furthermore, when viewed with brightfield or RICM imaging, the beads can be seen moving around via Brownian motion in a zero shear environment. Upon application of shear flow, the beads move in direction of the applied shear then stop after having displaced around 2.7 microns, which is the length of the tether. Since the beads are not stationary when no shear is applied, measuring the exact displacement is difficult. This controlled displacement indicates that the beads are tethered to the surface and is helpful for identifying active nanoreporters as beads nonspecifically bound to the glass do not move when shear is applied.

Another important point pertaining to the ability of these nanoreporters to directly measure shear is the exact vertical location of the bead. Given that the flow velocity profile near the wall may be linear, a bead anywhere within this linear region would technically experience the same shear. However, within this region, a bead further away from the wall will experience greater flow velocities and thus generate more drag. As such, function of the nanoreporter is inexorably tied to flow velocity, and thus the vertical position of the bead within the flow profile. For the nanoreporter to be called a shear sensor, and not a flow sensor, its bead must be in approximately the same y position in all samples and testing conditions. During our preliminary experiments, this is exactly what was observe. Tethered beads move freely in static conditions, and often are barely visible in RICM imaging as they float around over a micron away from the glass. But in flow conditions, even just a few dynes/$cm^2$, the beads will come down to the glass. This tells us that the nanoreporter beads are sensing flow velocity conditions consistently with the mechanical amplifier in the same y location, which is right up against the glass.

Improved Nanoreporter Yield

Initial experiments revealed consistent and repeatable nanoreporter function, but with few sensors per unit area compared to how many beads were being added to the chamber. Experiments were performed to determine if the yield of active sensors on glass surface could be dependent on the duration of the hairpin-tether with microbead incubation. Instead of 1 hour, an overnight incubation on a rotator increased active sensors per unit area over 50-fold.

Additionally, blocking both the glass surface and the beads with a PBS+Tween-20+1% BSA solution showed improvements. Otherwise, the entire glass surface would be covered with nonspecifically bound beads. It was discovered that large nonspecifically bound clumps of beads could be removed by a brief sonication of the beads after washing and before incubation with the dsTethers. Other areas of optimization that are contemplated are anti-digoxigenin concentration on glass, bead-tether-hairpin incubation on glass, and different blocking buffers.

Multi-Valent Mono-Active Tether Attachment

As the protocols used to create the nanoreporters would logically result in beads with more than one dsTether/hairpin chain attached to it (10×excess molar incubation of dsTether onto bead), it is likely the beads might be multivalent yet mono-active sensors. This means in a given flow direction, only one of the multiple tethers to a bead would experience tension and therefore produce fluorescent signal. This was confirmed this by subjecting the same region of interest with different directions of flow. Some of the fluorescing hairpin chains remained in the same location regardless of which direction of flow—thus suggesting the specific nanoreporter was truly monovalent. Other beads displayed disappearance of one hairpin chain but the appearance of another one upstream of the new flow direction relative to the first hairpin chain signal. Furthermore, reverting the flow direction results in a return of the initial hairpin chain location.

Multi-Valent Multi-Active Tether Attachment

While holding bead concentration and incubation times constant, the number of tethered beads on the glass surface is proportional to the concentration of purified hairpin-tethers incubated with the beads. As the tether concentration is increased to about 200 pM, the active 1-micron diameter beads per 100 square microns peaks at about 8. Further increase of tether concentration instead produces a proportional increasing prevalence of a second population of beads that are connected to more than one active hairpin-tether. The phenotype of this multi-active nanoreporter is two or more fluorescent spots near each other which are relatively perpendicular to the direction of flow, and visibly associated with a single bead. An increased flow rate is necessary to elicit full hairpin opening in the multi-tethered nanoreporter suggesting that the drag force is being shared in parallel across the two hairpin chains. At 200 pM dsTether, the occurrence of this multi-active nanoreporter is less than 1%, but at 500 pM dsTether, beads with 3 or even 4 active hairpin chains are commonplace.

Figure 5:
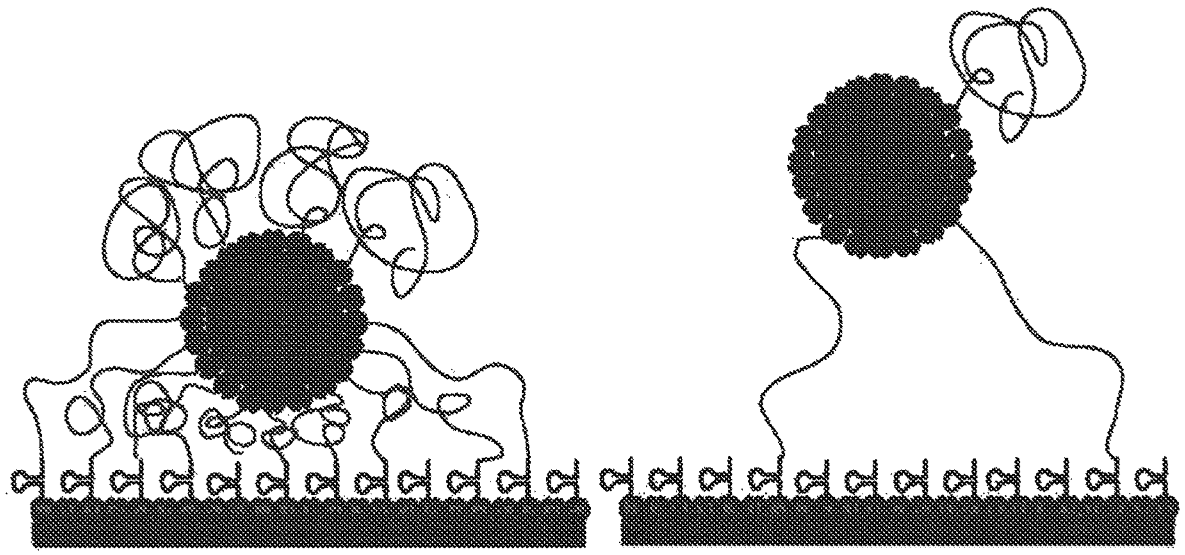
FIG. 5 illustrates that a high concentrations of double stranded tether DNA results in a supervalent bead with heavily restricted movement. Lower valency allows for beads with increased mobility which float above the glass and are not easily visible with reflection interference contrast microscopy (RICM). With applied shear, supervalent beads have restricted movement of only about 1 micron displacement: compare that to 2.5 microns of movement for of low valency beads.

The concept of multivalency was taken to the extreme by using a very high tether concentration of 1.4 nanomolar. In order to produce a tether concentration this high, the hairpin chain and tether assembly processes were separated. The surface was saturated with 15 nM of purified hairpin chains, while the beads were incubated with varying concentrations of double stranded linearized m13. The high concentration of dsTether resulted in beads with highly restricted movement. Even in static conditions, the beads appeared to be tied down to the glass, demonstrating less than half of the usual displacement under flow (See FIG. 5).

Expanded Nanoreporter Functionality

The molecular shear sensitive nanoreporter described above consists of a microbead, DNA tether, and fluorescence force transducer. To fully explore the design space of this approach, nanoreporters with different features were synthesize. This disclosure contemplates modifications such as: 1) the DNA hairpin sequence, which determines the threshold force for the opening of the hairpin; 2) the number of hairpins in the fluorescence force transducer; 3) the size and material of the microbead, and 4) the length of the DNA tether. Each one of these design parameters affects the behaviors of the nanoreporter. The DNA tether can be prepared by using m13 DNA, or longer DNA tethers can be produced by using lambda DNA, or by hierarchically assembling multiple m13 DNA strands. Shorter tethers can be prepared by cutting the current m13 scaffolds into approximate desired lengths with restriction enzymes.

GC 22% Hairpin F1/2 Modeling

Figure 2:
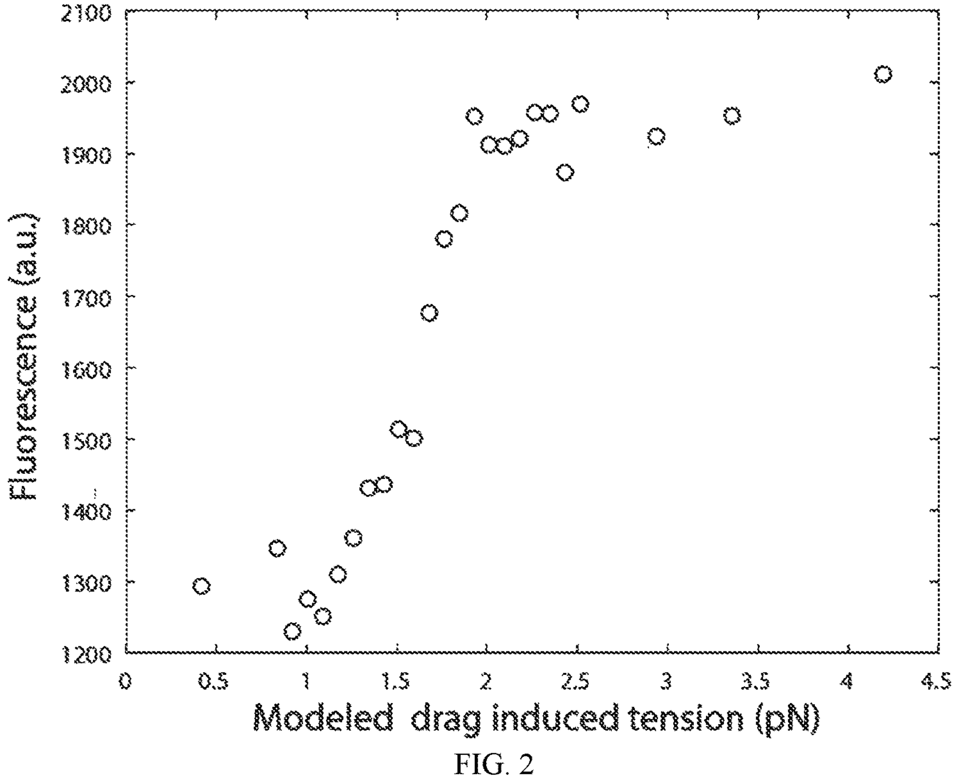
FIG. 2 shows calculations indicating a sigmoid curve of fluorescence intensity in response to increasing applied shear.

The hairpin chain opens over a narrow range of applied shear stress. After a base flow rate is reached, the fluorescent signal increases with flow rate until a maximum where all hairpins in the sensor assembly are open. Quantification of this fluorescence yields a sigmoid curve of the hairpin assembly's active range (FIG. 2). This means that at a given flow rate within the range of this sigmoid curve, an equilibrium number of ten hairpins in the chain are open.

Scaffolded Nanoreporter

Figure 1E:
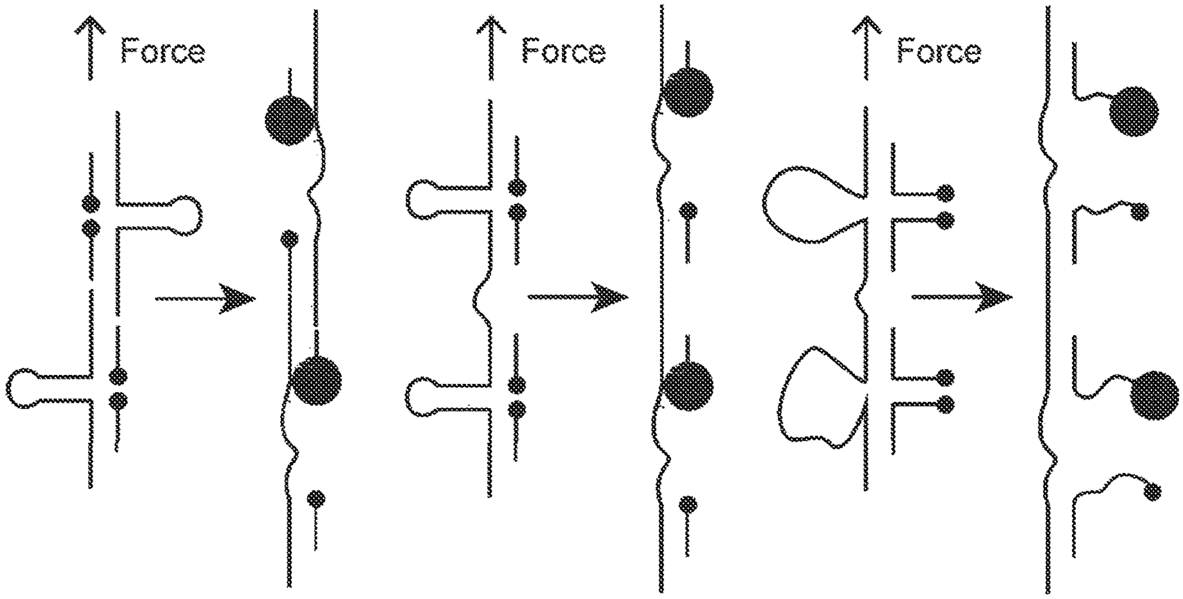
FIG. 1E illustrates alternative DNA force transducer designs e.g. contains a continuous long DNA strands as a backbone.

Scaffolded versions are contemplated where force sensitive components are included on the linearized tether strand. This way, tension is bore on the continuous tether, and not across unligated sticky ends. Preliminary exploration suggests non-specific interactions between the scaffold loops. Adding short staples into the loop are contemplated to reduce secondary structure in such a way that does not add tension to the hybridization between fluorophore and quencher strands (FIG. 1E).

DNA-Based Branched Kite Components

It is contemplated that a shear nanoreporter could also be created using DNA-based organic components (i.e. no bead). Shear nanoreporters are contemplated using an organic structure to generate drag forces. Drag is induced on linear structures, and the total applied force is proportional to the square root of the length of the polymer. Polymers of sufficient length can be used to measure the applied shear stress if a reporter is incorporated into the structure. A completely biomolecule-based structure is contemplated to be biodegradable improving in vivo compatibility. Assembly of nanoreporters driven by DNA hybridization streamlines the process and is contemplated to improves the yield and stability of the nanoreporter. Different geometries (e.g. dendrimers) enables incorporations of different shapes. The nanoreporters can be adapted to constricted anatomical locations.

Figure 3A:
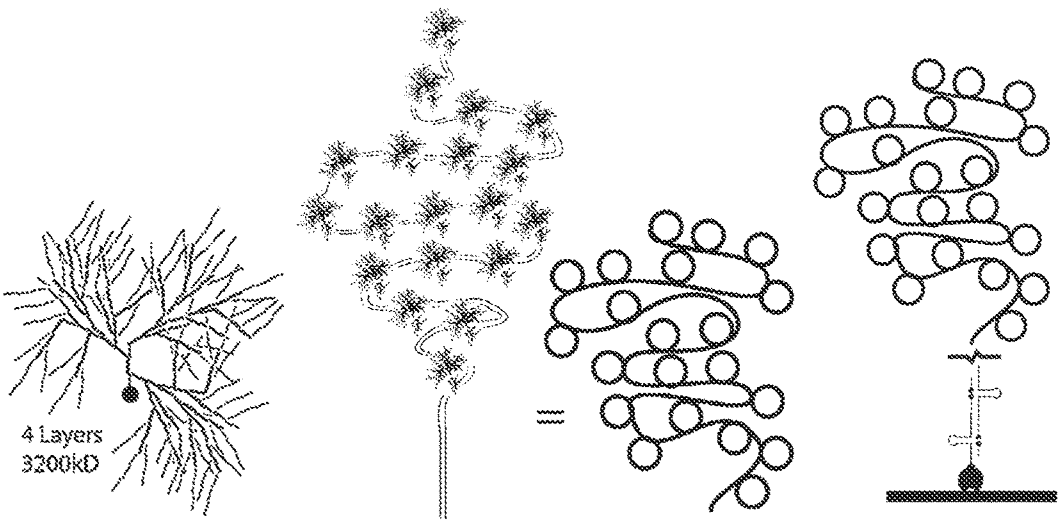
FIG. 3A illustrates a DNA amplifier containing a megadalton dendrimer composed of five unique DNA strands. Each subsequent layer of the dendrimer has three times as many components as the last which can be modified to be fluorescent with Alexa 647. A single dendrimer did not generate enough force to open the hairpins. Multiple dendrimers were used to create a DNA drogue. Dendrimers (192) were added onto the tether by incorporating a dendrimer capturing extension on every short oligo used to make the linearized p8064 m13 double stranded.
Figure 3B:
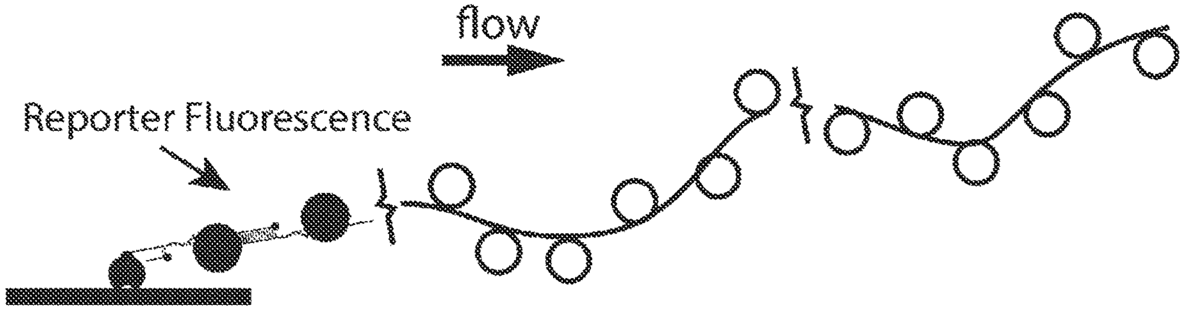
FIG. 3B illustrates a DNA drogue shear nanoreporter construct described in FIG. 3A that produces a signal at shear rates of around 100 dynes/cm$^2$.

DNA dendrimer-type construct are contemplated where each layer consists of three times more DNA strands than the previous layer. By first employing a single fluorescent dendrimer in place of the bead (FIG. 3A). An interesting side effect of attaching the fluorescent dendrimer to the dsTether was that they became easily distinguishable from dendrimers nonspecifically attached the glass. The active dendrimers appeared in the exposure as a fuzzy cloud of fluorescence, as they experience Brownian motion but are ultimately constrained by the dsTether. Contrarily, nonspecifically attached dendrimers appear as sharp points of fluorescence as they are stationary.

In static conditions, the fluorescent dendrimer can be seen co-localized on top of constitutively open hairpins. After application of shear, the dendrimer fluorescence displaces from the hairpin chain fluorescence in the direction of flow. With increasing applied shear, the displacement of the dendrimer from the hairpin chain increases. The dsTether could be stretched and displacement of the dendrimer from the hairpins did not exceed 2.8 microns, which is the designed length of the dsTether. The experiment was repeated with closed hairpins and increase the size of the dendrimer.

The open hairpin experiment was repeated with three different dendrimers: 2L (300 kD), 3L (1 MD), and 4L (3.2 MD). At a spread of different applied shears, the measured amount of tether extension was almost the exact same for all three dendrimer sizes. The only noticeable difference was at very high shear rates for the microfluidic, where the larger dendrimers produced greater extension than the smallest one. The 4L dendrimer with 3.2 MD mass failed to produce any hairpin signal even with shear increased to almost 300 dynes/cm$^2$ approaching the limit of the friction fitted microfluidic system This suggested to us that the dendrimers were barely contributing to the dsTethers.

While the dendrimer enabled extension of the tether was confirmed in flow, a single dendrimer had limited force to open the hairpins. Multiple dendrimers (192) were added onto the tether by incorporating a dendrimer capturing extension on short oligos used to make the linearized p8064 m13 double stranded (FIG. 3A). These capturing extensions hybridize the backbone strand of each dendrimer, or the strand that every other strand branches off of. This way a controlled number of dendrimers were program to hybridize to the long tether. DNA drogues comprised of 3L, 4L, and 5L dendrimers were compared respectively. During flow testing, the 5L dendrimer managed to produce fluorescent signal. The 5L dendrimer DNA drogue has a total designed mass of 2.2 billion Daltons. Although this is an incredibly large DNA structure, it still runs into the agarose gel with limited aggregation in the wells. This DNA drogue shear nanoreporter could produce signal at high shear rates of 100 dynes/cm$^2$. TEM imaging after agarose gel purification revealed a long and snakelike electron-dense megastructure.

Figure 3C:
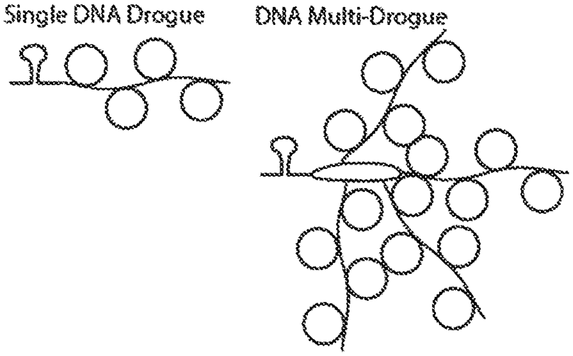
FIG. 3C illustrates multivalently attachment of several DNA drogues onto a single hairpin chain.
Figure 4:
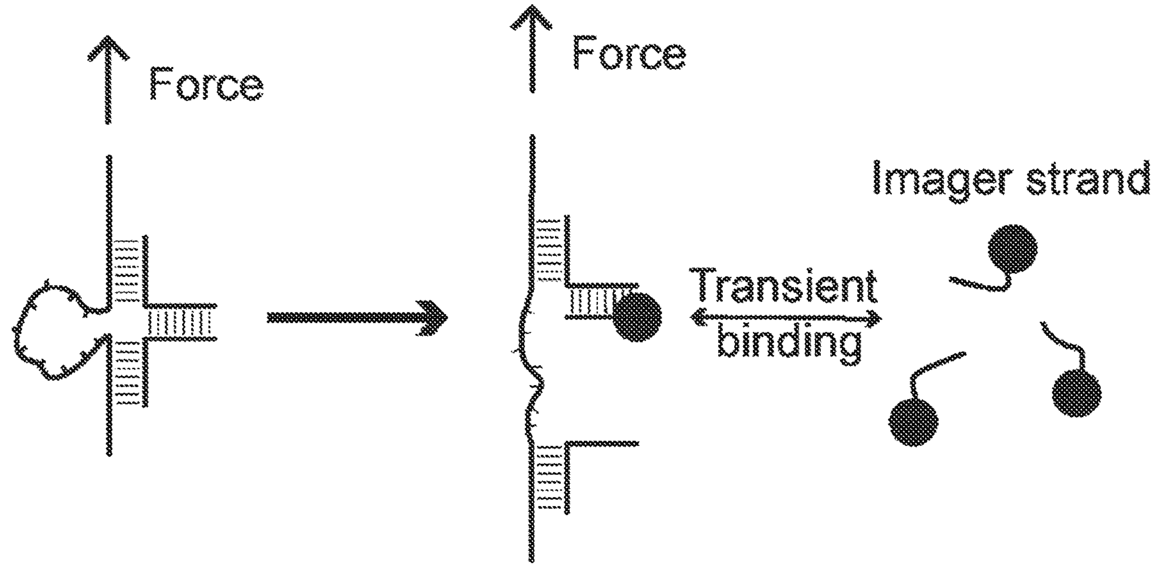
FIG. 4 illustrates using fluorescent probes that hybridize with de-hybridized segments as a result of force extension on hairpins which can be used alone or in combination with fluorescent dyes and quenchers.

Larger DNA drogues are contemplated by (1) adding more layers per dendrimer or (2) using multiple long DNA drogues with a single hairpin chain. It is contemplated that a 1:3 layer n-1 to layer n ratio to 1:2 or 1:1 can be created. It is also contemplated that one can use multiple long scaffold DNA to create an even larger structure, specifically using an intermediate size circular p3015 m13 DNA to simultaneously grab many fully formed DNA drogues (FIG. 3C).

Targeting of Shear Nanoreporter to Cells

Shear may affect numerous cell types in various anatomical locations. A key aspect of measuring the shear stress on these cells will be attaching a nanoreporter directly to the cell surface. This can be accomplished by conjugating molecules or proteins to the nanoreporter that will facilitate cell binding. Targeting specific antigens on the cell surface confers the additional advantage of targeting specific cell types and even cellular states. For example, vascular cell adhesion molecule-1 (VCAM-1) is expressed on activated endothelial cells and is a key marker of pro-atherosclerotic conditions. Hence, a shear nanoreporter targeting VCAM-1 will identify when pro-atherosclerotic conditions are present and report on the localized shear in that area. Importantly, given the versatility of DNA, numerous biomolecular conjugation techniques are available to bind targeting molecules to DNA.

Experiments were performed to determine whether nanoreporters could target specific cell markers. Initial experiments were directed to platelets. A DNA oligo with sequence was conjugated to anti-CD41 antibody using a commercially available kit (SoluLink® Protein-Oligo Conjugation Kit). Substitution of digoxigenin with this antibody-DNA conjugate switches the targeted binding site from anti-digoxigenin to platelet-specific integrin αIIbβ3, which is abundantly expressed on the platelet surface. Proper activity of the antibody after conjugation with DNA was first verified. Platelets were isolated using standard protocols and plated in a simple microfluidic structure created from PDMS channels (40 mm×2 mm×100 μm) and a No. 1.5 coverslip. The platelets were coated with the FPLC purified anti-CD41-DNA then washed with tween-20-free buffer. The platelets were incubated with constitutively open 10-hairpin-chains with either free or blocked anti-CD41-DNA hybridization sites. The hairpin chains with blocked hybridization sites showed very low binding, while the hairpin chains with free binding sites demonstrated excellent binding and fluorescence. Images were taken with TIRF so only the edges of the platelets are clearly visible — thicker areas of the platelets cannot be visualized with TIRF.

Figure 6:
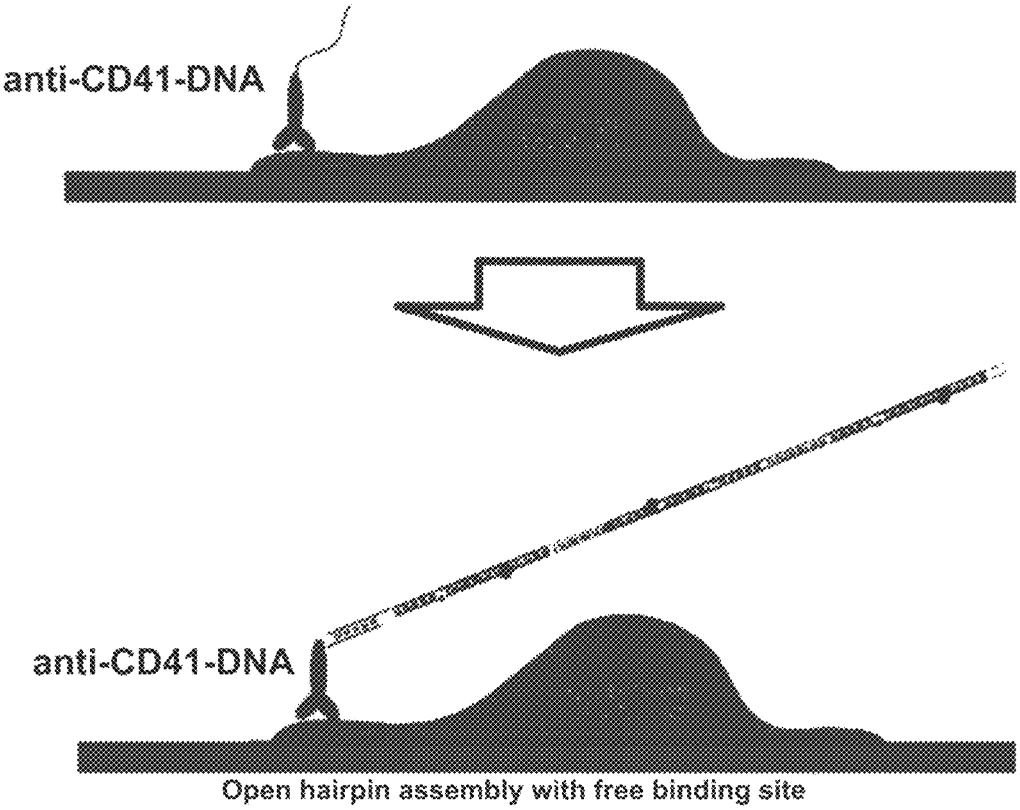
FIG. 6 illustrates the conjugation of DNA based fluorescent reporters using anti-CD41 antibodies for specific platelet targeting and shear flow mediated activation of nanoreporters on platelet surfaces.

Following these results, we attempted to assemble and use shear to activate the complete nanoreporter on platelets (FIG. 6). Purified hairpin-tether assemblies were incubated on beads as done previously, but without the anti-CD41-DNA. Following a washing step of the platelets using 1% BSA PBS buffer, the platelets were then incubated with a high concentration of anti-CD41-DNA and washed again. Finally, the hairpin-tether-bead assembly was incubated on the prepared platelets shortly before imaging.

One concern was that the applied forces will alter the binding affinity of the antibodies and that they will be unable to attach to the surface of the cells under flow. However, data from experiments suggest that this is not a concern for CD41 on platelets as the nanoreporter fluoresces at 25 dynes/cm$^2$. With an active sensor yield of at best 5%, significant non-specific binding from the streptavidin coated beads was noted, which is not unexpected given previous experience that beads stick to any biological materials present on the glass. It is contemplated that one can reduce adhesion by passivating the bead surface by saturating unbound streptavidin with biotinylated PEG at least 1 kD in size. Another option is to coat a bead in mutated streptavidin that does not contain a RYD sequence. The RYD sequence expressed by wild type streptavidin and mimics RGD (Arg-Gly-Asp). RGD is the universal recognition domain present in fibronectin and other adhesion-related molecules.

Nanoreporter in Endothelialized Microfluidics

A series of sensors can be designed to target various antigens starting with endothelial cell markers CD31/PE-CAM, VCAM, and CD43. Both microfluidic and larger "microfluidics" can be coated in a 3D conformal layer of endothelial cells that recapitulates the essential features of a biological system. This system can be modified by conjugating various antibodies to the previously characterized endothelial targets (CD31, VCAM, CD43, α4β1). It is contemplated that testing can be performed using blood products, e.g., whole blood.

The invention claimed is:

1. An optical shear flow system comprising:

a) a channel comprising a surface and a liquid in the channel;

b) a molecular arm comprising:

an anchor means, wherein the anchor is attached to the surface;

a force indicator, wherein the force indicator is a double stranded nucleic acid comprising multiple hairpin domains comprising multiple fluorescent dyes and multiple quenchers and attached to the anchor means, wherein the hairpin domains or nearby segments contain a quencher and fluorophore in sufficiently close proximity to prevent an optical signal and the optical signal results in the hairpin domains dehybridizing and separating the quencher from the fluorophore, wherein the multiple dyes and multiple quenchers are arranged such that no optical signal is emitted when liquid is static in the channel;

a tether attached to the force indicator, wherein the tether is a linear or circular double stranded nucleic acid sequence;

and shear flow resistors attached to the tether, wherein the shear flow resistors are branched nucleic acids attached through the tether;

wherein the branched nucleic acids have 10 or more primary branch points providing primary nucleic acid branches from the linear or circular nucleic acid;

wherein the primary nucleic acid branches are dendrimers, providing secondary, tertiary, and quaternary layers, wherein secondary, tertiary, and quaternary layers of the dendrimers have three times more nucleic acid strands than a previous layer of the respective secondary, tertiary, and quaternary layers; and c) a liquid in the channel;

wherein the anchor is attached to the surface; and wherein the shear flow resistors cause the force indicator to expand providing an optical signal if the liquid flows through and parallel to the channel at or above a critical velocity as a result of the hairpin domains dehybridizing and separating the quencher from the fluorophore.

2. The system of claim 1, wherein the channel has a cross-sectional area of less than 50, cm2.

3. The system of claim 1, wherein the surface is glass, metal, polymer, protein, cell, group of cells, or combinations thereof.

4. The system of claim 1, wherein the anchor is an antibody, specific binding agent, ligand or receptor and the surface comprises an antigen, specific binding agent, receptor or a ligand, respectively.

5. The system of claim 1, wherein the optical signal is a result of hairpin domains dehybridizing forming single stranded segments and the optical signal is a result of fluorescent probes in the liquid hybridizing the single stranded segments.

6. The system of claim 1, wherein the branched nucleic acids have 25 or more primary branch points providing primary nucleic acid branches from a linear or circular nucleic acid.

7. The system of claim 1, wherein the anchor is an antibody to CD31, VCAM, CD43, or $\alpha 4\beta 1$ or other specific binding agent to CD31, VCAM, CD43, or $\alpha 4\beta 1$.

8. The system of claim 2, wherein the channel has a cross-sectional area of less than 10 cm2.

9. The system of claim 2, wherein the channel has a cross-sectional area of less than 5 cm2.

10. The system of claim 6, wherein the branched nucleic acids have 50 or more primary branch points providing primary nucleic acid branches from a linear or circular nucleic acid.

11. The system of claim 6, wherein the branched nucleic acids have 100 or more primary branch points providing primary nucleic acid branches from a linear or circular nucleic acid.

12. The system of claim 1, wherein the multiple hairpin domains are 10 or more.

* * * * *

SEQUENCE LISTING

```
<160> NUMBER OF SEQ ID NOS: 406

<210> SEQ ID NO 1
<211> LENGTH: 87
```

<212> TYPE: DNA
<213> ORGANISM: Artificial
<220> FEATURE:
<223> OTHER INFORMATION: Synthetic construct

<400> SEQUENCE: 1
tctactaaaa ctctatcaca ccggagcgcc tccgtgtata aatgttttca tttatacgcg 60
tcaatgtaca cgtcttggca ggcatca 87

<210> SEQ ID NO 2
<211> LENGTH: 82
<212> TYPE: DNA
<213> ORGANISM: Artificial
<220> FEATURE:
<223> OTHER INFORMATION: Synthetic construct

<400> SEQUENCE: 2
tgacgccaag ttcgaccgga gcgcctccgt gtataaatgt tttcatttat acgcgtcaat 60
gtacacgtga tgcctgccaa ga 82

<210> SEQ ID NO 3
<211> LENGTH: 82
<212> TYPE: DNA
<213> ORGANISM: Artificial
<220> FEATURE:
<223> OTHER INFORMATION: Synthetic construct

<400> SEQUENCE: 3
tcgaacttgg cgtcaccgga gcgcctccgt gtataaatgt tttcatttat acgcgtcaat 60
gtacacgcag cgttattcgc ga 82

<210> SEQ ID NO 4
<211> LENGTH: 82
<212> TYPE: DNA
<213> ORGANISM: Artificial
<220> FEATURE:
<223> OTHER INFORMATION: Synthetic construct

<400> SEQUENCE: 4
caatttcgag gaccgccgga gcgcctccgt gtataaatgt tttcatttat acgcgtcaat 60
gtacacgtcg cgaataacgc tg 82

<210> SEQ ID NO 5
<211> LENGTH: 82
<212> TYPE: DNA
<213> ORGANISM: Artificial
<220> FEATURE:
<223> OTHER INFORMATION: Synthetic construct

<400> SEQUENCE: 5
cggtcctcga aattgccgga gcgcctccgt gtataaatgt tttcatttat acgcgtcaat 60
gtacacgggc tctcagctta ag 82

<210> SEQ ID NO 6
<211> LENGTH: 82
<212> TYPE: DNA
<213> ORGANISM: Artificial
<220> FEATURE:
<223> OTHER INFORMATION: Synthetic construct

<400> SEQUENCE: 6
gtcgtcacca gagatccgga gcgcctccgt gtataaatgt tttcatttat acgcgtcaat 60
gtacacgctt aagctgagag cc 82

<210> SEQ ID NO 7
<211> LENGTH: 82
<212> TYPE: DNA
<213> ORGANISM: Artificial
<220> FEATURE:
<223> OTHER INFORMATION: Synthetic construct

<400> SEQUENCE: 7
atctctggtg acgacccgga gcgcctccgt gtataaatgt tttcatttat acgcgtcaat 60
gtacacggcc aagtcgtcat tg 82

<210> SEQ ID NO 8
<211> LENGTH: 82
<212> TYPE: DNA
<213> ORGANISM: Artificial
<220> FEATURE:
<223> OTHER INFORMATION: Synthetic construct

<400> SEQUENCE: 8
aagctacctg cgatgccgga gcgcctccgt gtataaatgt tttcatttat acgcgtcaat 60
gtacacgcaa tgacgacttg gc 82

<210> SEQ ID NO 9
<211> LENGTH: 82
<212> TYPE: DNA
<213> ORGANISM: Artificial
<220> FEATURE:
<223> OTHER INFORMATION: Synthetic construct

<400> SEQUENCE: 9
catcgcaggt agcttccgga gcgcctccgt gtataaatgt tttcatttat acgcgtcaat 60
gtacacggac gcacgctttg ta 82

<210> SEQ ID NO 10
<211> LENGTH: 82
<212> TYPE: DNA
<213> ORGANISM: Artificial
<220> FEATURE:
<223> OTHER INFORMATION: Synthetic construct

<400> SEQUENCE: 10
tcctccatcc cttccccgga gcgcctccgt gtataaatgt tttcatttat acgcgtcaat 60
gtacacgtac aaagcgtgcg tc 82

<210> SEQ ID NO 11
<211> LENGTH: 41
<212> TYPE: DNA
<213> ORGANISM: Artificial
<220> FEATURE:
<223> OTHER INFORMATION: Synthetic construct

<400> SEQUENCE: 11
tgtgatagag ttttagtaga ctttcctcgt tagaatcaga g 41

<210> SEQ ID NO 12
<211> LENGTH: 36
<212> TYPE: DNA

<213> ORGANISM: Artificial
<220> FEATURE:
<223> OTHER INFORMATION: Synthetic construct

<400> SEQUENCE: 12
gggcgcgtac tatggttgct tttaggagtg tgggaa 36

<210> SEQ ID NO 13
<211> LENGTH: 15
<212> TYPE: DNA
<213> ORGANISM: Artificial
<220> FEATURE:
<223> OTHER INFORMATION: Synthetic construct

<400> SEQUENCE: 13
ttcccacact cctaa 15

<210> SEQ ID NO 14
<211> LENGTH: 17
<212> TYPE: DNA
<213> ORGANISM: Artificial
<220> FEATURE:
<223> OTHER INFORMATION: Synthetic construct

<400> SEQUENCE: 14
ggaagggatg gaggatt 17

<210> SEQ ID NO 15
<211> LENGTH: 15
<212> TYPE: DNA
<213> ORGANISM: Artificial
<220> FEATURE:
<223> OTHER INFORMATION: Synthetic construct

<400> SEQUENCE: 15
acggaggcgc tccgg 15

<210> SEQ ID NO 16
<211> LENGTH: 15
<212> TYPE: DNA
<213> ORGANISM: Artificial
<220> FEATURE:
<223> OTHER INFORMATION: Synthetic construct

<400> SEQUENCE: 16
cgtgtacatt gacgc 15

<210> SEQ ID NO 17
<211> LENGTH: 42
<212> TYPE: DNA
<213> ORGANISM: Artificial
<220> FEATURE:
<223> OTHER INFORMATION: Synthetic construct

<400> SEQUENCE: 17
cgggagctaa acaggaggcc gattaaaggg attttagaca gg 42

<210> SEQ ID NO 18
<211> LENGTH: 42
<212> TYPE: DNA
<213> ORGANISM: Artificial
<220> FEATURE:
<223> OTHER INFORMATION: Synthetic construct

<400> SEQUENCE: 18
aacggtacgc cagaatcctg agaagtgttt ttataatcag tg 42

<210> SEQ ID NO 19
<211> LENGTH: 42
<212> TYPE: DNA
<213> ORGANISM: Artificial
<220> FEATURE:
<223> OTHER INFORMATION: Synthetic construct

<400> SEQUENCE: 19
aggccaccga gtaaaagagt ctgtccatca cgcaaattaa cc 42

<210> SEQ ID NO 20
<211> LENGTH: 42
<212> TYPE: DNA
<213> ORGANISM: Artificial
<220> FEATURE:
<223> OTHER INFORMATION: Synthetic construct

<400> SEQUENCE: 20
gttgtagcaa tacttctttg attagtaata acatcacttg cc 42

<210> SEQ ID NO 21
<211> LENGTH: 42
<212> TYPE: DNA
<213> ORGANISM: Artificial
<220> FEATURE:
<223> OTHER INFORMATION: Synthetic construct

<400> SEQUENCE: 21
tgagtagaag aactcaaact atcggccttg ctggtaatat cc 42

<210> SEQ ID NO 22
<211> LENGTH: 42
<212> TYPE: DNA
<213> ORGANISM: Artificial
<220> FEATURE:
<223> OTHER INFORMATION: Synthetic construct

<400> SEQUENCE: 22
agaacaatat taccgccagc cattgcaaca ggaaaaacgc tc 42

<210> SEQ ID NO 23
<211> LENGTH: 42
<212> TYPE: DNA
<213> ORGANISM: Artificial
<220> FEATURE:
<223> OTHER INFORMATION: Synthetic construct

<400> SEQUENCE: 23
atggaaatac ctacattttg acgctcaatc gtctgaaatg ga 42

<210> SEQ ID NO 24
<211> LENGTH: 42
<212> TYPE: DNA
<213> ORGANISM: Artificial
<220> FEATURE:
<223> OTHER INFORMATION: Synthetic construct

<400> SEQUENCE: 24
ttatttacat tggcagattc accagtcaca cgaccagtaa ta 42

<210> SEQ ID NO 25
<211> LENGTH: 42
<212> TYPE: DNA
<213> ORGANISM: Artificial
<220> FEATURE:

<223> OTHER INFORMATION: Synthetic construct

<400> SEQUENCE: 25
aaagggacat tctggccaac agagatagaa cccttctgac ct 42

<210> SEQ ID NO 26
<211> LENGTH: 42
<212> TYPE: DNA
<213> ORGANISM: Artificial
<220> FEATURE:
<223> OTHER INFORMATION: Synthetic construct

<400> SEQUENCE: 26
gaaagcgtaa gaatacgtgg cacagacaat atttttgaat gg 42

<210> SEQ ID NO 27
<211> LENGTH: 42
<212> TYPE: DNA
<213> ORGANISM: Artificial
<220> FEATURE:
<223> OTHER INFORMATION: Synthetic construct

<400> SEQUENCE: 27
ctattagtct ttaatgcgcg aactgatagc cctaaaacat cg 42

<210> SEQ ID NO 28
<211> LENGTH: 42
<212> TYPE: DNA
<213> ORGANISM: Artificial
<220> FEATURE:
<223> OTHER INFORMATION: Synthetic construct

<400> SEQUENCE: 28
ccattaaaaa taccgaacga accaccagca gaagataaaa ca 42

<210> SEQ ID NO 29
<211> LENGTH: 42
<212> TYPE: DNA
<213> ORGANISM: Artificial
<220> FEATURE:
<223> OTHER INFORMATION: Synthetic construct

<400> SEQUENCE: 29
gaggtgaggc ggtcagtatt aacaccgcct gcaacagtgc ca 42

<210> SEQ ID NO 30
<211> LENGTH: 42
<212> TYPE: DNA
<213> ORGANISM: Artificial
<220> FEATURE:
<223> OTHER INFORMATION: Synthetic construct

<400> SEQUENCE: 30
cgctgagagc cagcagcaaa tgaaaaatct aaagcatcac ct 42

<210> SEQ ID NO 31
<211> LENGTH: 42
<212> TYPE: DNA
<213> ORGANISM: Artificial
<220> FEATURE:
<223> OTHER INFORMATION: Synthetic construct

<400> SEQUENCE: 31
tgctgaacct caaatatcaa accctcaatc aatatctggt ca 42

<210> SEQ ID NO 32
<211> LENGTH: 42
<212> TYPE: DNA
<213> ORGANISM: Artificial
<220> FEATURE:
<223> OTHER INFORMATION: Synthetic construct

<400> SEQUENCE: 32
gttggcaaat caacagttga aaggaattga ggaaggttat ct 42

<210> SEQ ID NO 33
<211> LENGTH: 42
<212> TYPE: DNA
<213> ORGANISM: Artificial
<220> FEATURE:
<223> OTHER INFORMATION: Synthetic construct

<400> SEQUENCE: 33
aaaatatctt taggagcact aacaactaat agattagagc cg 42

<210> SEQ ID NO 34
<211> LENGTH: 42
<212> TYPE: DNA
<213> ORGANISM: Artificial
<220> FEATURE:
<223> OTHER INFORMATION: Synthetic construct

<400> SEQUENCE: 34
tcaatagata atacatttga ggatttagaa gtattagact tt 42

<210> SEQ ID NO 35
<211> LENGTH: 42
<212> TYPE: DNA
<213> ORGANISM: Artificial
<220> FEATURE:
<223> OTHER INFORMATION: Synthetic construct

<400> SEQUENCE: 35
acaaacaatt cgacaactcg tattaaatcc tttgcccgaa cg 42

<210> SEQ ID NO 36
<211> LENGTH: 42
<212> TYPE: DNA
<213> ORGANISM: Artificial
<220> FEATURE:
<223> OTHER INFORMATION: Synthetic construct

<400> SEQUENCE: 36
ttattaattt taaaagtttg agtaacatta tcattttgcg ga 42

<210> SEQ ID NO 37
<211> LENGTH: 42
<212> TYPE: DNA
<213> ORGANISM: Artificial
<220> FEATURE:
<223> OTHER INFORMATION: Synthetic construct

<400> SEQUENCE: 37
acaaagaaac caccagaagg agcggaatta tcatcatatt cc 42

<210> SEQ ID NO 38
<211> LENGTH: 42
<212> TYPE: DNA
<213> ORGANISM: Artificial
<220> FEATURE:
<223> OTHER INFORMATION: Synthetic construct

<400> SEQUENCE: 38
tgattatcag atgatggcaa ttcatcaata taatcctgat tg 42

<210> SEQ ID NO 39
<211> LENGTH: 42
<212> TYPE: DNA
<213> ORGANISM: Artificial
<220> FEATURE:
<223> OTHER INFORMATION: Synthetic construct

<400> SEQUENCE: 39
tttggattat acttctgaat aatggaaggg ttagaaccta cc 42

<210> SEQ ID NO 40
<211> LENGTH: 42
<212> TYPE: DNA
<213> ORGANISM: Artificial
<220> FEATURE:
<223> OTHER INFORMATION: Synthetic construct

<400> SEQUENCE: 40
atatcaaaat tatttgcacg taaaacagaa ataaagaaat tg 42

<210> SEQ ID NO 41
<211> LENGTH: 42
<212> TYPE: DNA
<213> ORGANISM: Artificial
<220> FEATURE:
<223> OTHER INFORMATION: Synthetic construct

<400> SEQUENCE: 41
cgtagatttt caggtttaac gtcagatgaa tatacagtaa ca 42

<210> SEQ ID NO 42
<211> LENGTH: 42
<212> TYPE: DNA
<213> ORGANISM: Artificial
<220> FEATURE:
<223> OTHER INFORMATION: Synthetic construct

<400> SEQUENCE: 42
gtacctttta catcgggaga aacaataacg gattcgcctg at 42

<210> SEQ ID NO 43
<211> LENGTH: 42
<212> TYPE: DNA
<213> ORGANISM: Artificial
<220> FEATURE:
<223> OTHER INFORMATION: Synthetic construct

<400> SEQUENCE: 43
tgctttgaat accaagttac aaaatcgcgc agaggcgaat ta 42

<210> SEQ ID NO 44
<211> LENGTH: 42
<212> TYPE: DNA
<213> ORGANISM: Artificial
<220> FEATURE:
<223> OTHER INFORMATION: Synthetic construct

<400> SEQUENCE: 44
ttcatttcaa ttacctgagc aaaagaagat gatgaaacaa ac 42

<210> SEQ ID NO 45
<211> LENGTH: 42

<212> TYPE: DNA
<213> ORGANISM: Artificial
<220> FEATURE:
<223> OTHER INFORMATION: Synthetic construct

<400> SEQUENCE: 45
atcaagaaaa caaaattaat tacatttaac aatttcattt ga 42

<210> SEQ ID NO 46
<211> LENGTH: 42
<212> TYPE: DNA
<213> ORGANISM: Artificial
<220> FEATURE:
<223> OTHER INFORMATION: Synthetic construct

<400> SEQUENCE: 46
attacctttt ttaatggaaa cagtacataa atcaatatat gt 42

<210> SEQ ID NO 47
<211> LENGTH: 42
<212> TYPE: DNA
<213> ORGANISM: Artificial
<220> FEATURE:
<223> OTHER INFORMATION: Synthetic construct

<400> SEQUENCE: 47
gagtgaataa ccttgcttct gtaaatcgtc gctattaatt aa 42

<210> SEQ ID NO 48
<211> LENGTH: 42
<212> TYPE: DNA
<213> ORGANISM: Artificial
<220> FEATURE:
<223> OTHER INFORMATION: Synthetic construct

<400> SEQUENCE: 48
ttttccctta gaatccttga aaacatagcg atagcttaga tt 42

<210> SEQ ID NO 49
<211> LENGTH: 42
<212> TYPE: DNA
<213> ORGANISM: Artificial
<220> FEATURE:
<223> OTHER INFORMATION: Synthetic construct

<400> SEQUENCE: 49
aagacgctga gaagagtcaa tagtgaattt atcaaaatca ta 42

<210> SEQ ID NO 50
<211> LENGTH: 42
<212> TYPE: DNA
<213> ORGANISM: Artificial
<220> FEATURE:
<223> OTHER INFORMATION: Synthetic construct

<400> SEQUENCE: 50
ggtctgagag actacctttt taacctccgg cttaggttgg gt 42

<210> SEQ ID NO 51
<211> LENGTH: 42
<212> TYPE: DNA
<213> ORGANISM: Artificial
<220> FEATURE:
<223> OTHER INFORMATION: Synthetic construct

<400> SEQUENCE: 51
tatataacta tatgtaaatg ctgatgcaaa tccaatcgca ag 42

<210> SEQ ID NO 52
<211> LENGTH: 42
<212> TYPE: DNA
<213> ORGANISM: Artificial
<220> FEATURE:
<223> OTHER INFORMATION: Synthetic construct

<400> SEQUENCE: 52
acaaagaacg cgagaaaact ttttcaaata tattttagtt aa 42

<210> SEQ ID NO 53
<211> LENGTH: 42
<212> TYPE: DNA
<213> ORGANISM: Artificial
<220> FEATURE:
<223> OTHER INFORMATION: Synthetic construct

<400> SEQUENCE: 53
tttcatcttc tgacctaaat ttaatggttt gaaataccga cc 42

<210> SEQ ID NO 54
<211> LENGTH: 42
<212> TYPE: DNA
<213> ORGANISM: Artificial
<220> FEATURE:
<223> OTHER INFORMATION: Synthetic construct

<400> SEQUENCE: 54
gtgtgataaa taaggcgtta aataagaata aacaccggaa tc 42

<210> SEQ ID NO 55
<211> LENGTH: 42
<212> TYPE: DNA
<213> ORGANISM: Artificial
<220> FEATURE:
<223> OTHER INFORMATION: Synthetic construct

<400> SEQUENCE: 55
ataattacta gaaaaagcct gtttagtatc atatgcgtta ta 42

<210> SEQ ID NO 56
<211> LENGTH: 42
<212> TYPE: DNA
<213> ORGANISM: Artificial
<220> FEATURE:
<223> OTHER INFORMATION: Synthetic construct

<400> SEQUENCE: 56
caaattctta ccagtataaa gccaacgctc aacagtaggg ct 42

<210> SEQ ID NO 57
<211> LENGTH: 42
<212> TYPE: DNA
<213> ORGANISM: Artificial
<220> FEATURE:
<223> OTHER INFORMATION: Synthetic construct

<400> SEQUENCE: 57
taattgagaa tcgccatatt taacaacgcc aacatgtaat tt 42

<210> SEQ ID NO 58

<211> LENGTH: 42
<212> TYPE: DNA
<213> ORGANISM: Artificial
<220> FEATURE:
<223> OTHER INFORMATION: Synthetic construct

<400> SEQUENCE: 58
aggcagaggc attttcgagc cagtaataag agaatataaa gt 42

<210> SEQ ID NO 59
<211> LENGTH: 42
<212> TYPE: DNA
<213> ORGANISM: Artificial
<220> FEATURE:
<223> OTHER INFORMATION: Synthetic construct

<400> SEQUENCE: 59
accgacaaaa ggtaaagtaa ttctgtccag acgacgacaa ta 42

<210> SEQ ID NO 60
<211> LENGTH: 42
<212> TYPE: DNA
<213> ORGANISM: Artificial
<220> FEATURE:
<223> OTHER INFORMATION: Synthetic construct

<400> SEQUENCE: 60
aacaacatgt tcagctaatg cagaacgcgc ctgtttatca ac 42

<210> SEQ ID NO 61
<211> LENGTH: 42
<212> TYPE: DNA
<213> ORGANISM: Artificial
<220> FEATURE:
<223> OTHER INFORMATION: Synthetic construct

<400> SEQUENCE: 61
aatagataag tcctgaacaa gaaaaataat atcccatcct aa 42

<210> SEQ ID NO 62
<211> LENGTH: 42
<212> TYPE: DNA
<213> ORGANISM: Artificial
<220> FEATURE:
<223> OTHER INFORMATION: Synthetic construct

<400> SEQUENCE: 62
tttacgagca tgtagaaacc aatcaataat cggctgtctt tc 42

<210> SEQ ID NO 63
<211> LENGTH: 42
<212> TYPE: DNA
<213> ORGANISM: Artificial
<220> FEATURE:
<223> OTHER INFORMATION: Synthetic construct

<400> SEQUENCE: 63
cttatcattc caagaacggg tattaaacca agtaccgcac tc 42

<210> SEQ ID NO 64
<211> LENGTH: 42
<212> TYPE: DNA
<213> ORGANISM: Artificial
<220> FEATURE:
<223> OTHER INFORMATION: Synthetic construct

<400> SEQUENCE: 64
atcgagaaca agcaagccgt ttttattttc atcgtaggaa tc 42

<210> SEQ ID NO 65
<211> LENGTH: 42
<212> TYPE: DNA
<213> ORGANISM: Artificial
<220> FEATURE:
<223> OTHER INFORMATION: Synthetic construct

<400> SEQUENCE: 65
attaccgcgc ccaatagcaa gcaaatcaga tatagaaggc tt 42

<210> SEQ ID NO 66
<211> LENGTH: 42
<212> TYPE: DNA
<213> ORGANISM: Artificial
<220> FEATURE:
<223> OTHER INFORMATION: Synthetic construct

<400> SEQUENCE: 66
atccggtatt ctaagaacgc gaggcgtttt agcgaacctc cc 42

<210> SEQ ID NO 67
<211> LENGTH: 42
<212> TYPE: DNA
<213> ORGANISM: Artificial
<220> FEATURE:
<223> OTHER INFORMATION: Synthetic construct

<400> SEQUENCE: 67
gacttgcggg aggttttgaa gccttaaatc aagattagtt gc 42

<210> SEQ ID NO 68
<211> LENGTH: 42
<212> TYPE: DNA
<213> ORGANISM: Artificial
<220> FEATURE:
<223> OTHER INFORMATION: Synthetic construct

<400> SEQUENCE: 68
tattttgcac ccagctacaa ttttatcctg aatcttacca ac 42

<210> SEQ ID NO 69
<211> LENGTH: 42
<212> TYPE: DNA
<213> ORGANISM: Artificial
<220> FEATURE:
<223> OTHER INFORMATION: Synthetic construct

<400> SEQUENCE: 69
gctaacgagc gtctttccag agcctaattt gccagttaca aa 42

<210> SEQ ID NO 70
<211> LENGTH: 42
<212> TYPE: DNA
<213> ORGANISM: Artificial
<220> FEATURE:
<223> OTHER INFORMATION: Synthetic construct

<400> SEQUENCE: 70
ataaacagcc atattattta tcccaatcca aataagaaac ga 42

<210> SEQ ID NO 71

<211> LENGTH: 42
<212> TYPE: DNA
<213> ORGANISM: Artificial
<220> FEATURE:
<223> OTHER INFORMATION: Synthetic construct

<400> SEQUENCE: 71 tttttgttt aacgtcaaaa atgaaaatag cagcctttac ag 42

<210> SEQ ID NO 72
<211> LENGTH: 42
<212> TYPE: DNA
<213> ORGANISM: Artificial
<220> FEATURE:
<223> OTHER INFORMATION: Synthetic construct

<400> SEQUENCE: 72
agagaataac ataaaaacag ggaagcgcat tagacgggag aa 42

<210> SEQ ID NO 73
<211> LENGTH: 42
<212> TYPE: DNA
<213> ORGANISM: Artificial
<220> FEATURE:
<223> OTHER INFORMATION: Synthetic construct

<400> SEQUENCE: 73
ttaactgaac accctgaaca aagtcagagg gtaattgagc gc 42

<210> SEQ ID NO 74
<211> LENGTH: 42
<212> TYPE: DNA
<213> ORGANISM: Artificial
<220> FEATURE:
<223> OTHER INFORMATION: Synthetic construct

<400> SEQUENCE: 74
taatatcaga gagataaccc acaagaattg agttaagccc aa 42

<210> SEQ ID NO 75
<211> LENGTH: 42
<212> TYPE: DNA
<213> ORGANISM: Artificial
<220> FEATURE:
<223> OTHER INFORMATION: Synthetic construct

<400> SEQUENCE: 75
taataagagc aagaaacaat gaaatagcaa tagctatctt ac 42

<210> SEQ ID NO 76
<211> LENGTH: 42
<212> TYPE: DNA
<213> ORGANISM: Artificial
<220> FEATURE:
<223> OTHER INFORMATION: Synthetic construct

<400> SEQUENCE: 76
cgaagccctt tttaagaaaa gtaagcagat agccgaacaa ag 42

<210> SEQ ID NO 77
<211> LENGTH: 42
<212> TYPE: DNA
<213> ORGANISM: Artificial
<220> FEATURE:
<223> OTHER INFORMATION: Synthetic construct

<400> SEQUENCE: 77
ttaccagaag gaaaccgagg aaacgcaata ataacggaat ac 42

<210> SEQ ID NO 78
<211> LENGTH: 42
<212> TYPE: DNA
<213> ORGANISM: Artificial
<220> FEATURE:
<223> OTHER INFORMATION: Synthetic construct

<400> SEQUENCE: 78
ccaaaagaac tggcatgatt aagactcctt attacgcagt at 42

<210> SEQ ID NO 79
<211> LENGTH: 42
<212> TYPE: DNA
<213> ORGANISM: Artificial
<220> FEATURE:
<223> OTHER INFORMATION: Synthetic construct

<400> SEQUENCE: 79
gttagcaaac gtagaaaata catacataaa ggtggcaaca ta 42

<210> SEQ ID NO 80
<211> LENGTH: 42
<212> TYPE: DNA
<213> ORGANISM: Artificial
<220> FEATURE:
<223> OTHER INFORMATION: Synthetic construct

<400> SEQUENCE: 80
taaaagaaac gcaaagacac cacggaataa gtttattttg tc 42

<210> SEQ ID NO 81
<211> LENGTH: 42
<212> TYPE: DNA
<213> ORGANISM: Artificial
<220> FEATURE:
<223> OTHER INFORMATION: Synthetic construct

<400> SEQUENCE: 81
acaatcaata gaaaattcat atggtttacc agcgccaaag ac 42

<210> SEQ ID NO 82
<211> LENGTH: 42
<212> TYPE: DNA
<213> ORGANISM: Artificial
<220> FEATURE:
<223> OTHER INFORMATION: Synthetic construct

<400> SEQUENCE: 82
aaaagggcga cattcaaccg attgagggag ggaaggtaaa ta 42

<210> SEQ ID NO 83
<211> LENGTH: 42
<212> TYPE: DNA
<213> ORGANISM: Artificial
<220> FEATURE:
<223> OTHER INFORMATION: Synthetic construct

<400> SEQUENCE: 83
ttgacggaaa ttattcatta aaggtgaatt atcaccgtca cc 42

<210> SEQ ID NO 84

<211> LENGTH: 42
<212> TYPE: DNA
<213> ORGANISM: Artificial
<220> FEATURE:
<223> OTHER INFORMATION: Synthetic construct

<400> SEQUENCE: 84
gacttgagcc atttgggaat tagagccagc aaaatcacca gt 42

<210> SEQ ID NO 85
<211> LENGTH: 42
<212> TYPE: DNA
<213> ORGANISM: Artificial
<220> FEATURE:
<223> OTHER INFORMATION: Synthetic construct

<400> SEQUENCE: 85
agcaccatta ccattagcaa ggccggaaac gtcaccaatg aa 42

<210> SEQ ID NO 86
<211> LENGTH: 42
<212> TYPE: DNA
<213> ORGANISM: Artificial
<220> FEATURE:
<223> OTHER INFORMATION: Synthetic construct

<400> SEQUENCE: 86
accatcgata gcagcaccgt aatcagtagc gacagaatca ag 42

<210> SEQ ID NO 87
<211> LENGTH: 42
<212> TYPE: DNA
<213> ORGANISM: Artificial
<220> FEATURE:
<223> OTHER INFORMATION: Synthetic construct

<400> SEQUENCE: 87
tttgccttta gcgtcagact gtagcgcgtt ttcatcggca tt 42

<210> SEQ ID NO 88
<211> LENGTH: 42
<212> TYPE: DNA
<213> ORGANISM: Artificial
<220> FEATURE:
<223> OTHER INFORMATION: Synthetic construct

<400> SEQUENCE: 88
ttcggtcata gcccccttat tagcgtttgc catcttttca ta 42

<210> SEQ ID NO 89
<211> LENGTH: 42
<212> TYPE: DNA
<213> ORGANISM: Artificial
<220> FEATURE:
<223> OTHER INFORMATION: Synthetic construct

<400> SEQUENCE: 89
atcaaaatca ccggaaccag agccaccacc ggaaccgcct cc 42

<210> SEQ ID NO 90
<211> LENGTH: 42
<212> TYPE: DNA
<213> ORGANISM: Artificial
<220> FEATURE:
<223> OTHER INFORMATION: Synthetic construct

<400> SEQUENCE: 90
ctcagagccg ccaccctcag aaccgccacc ctcagagcca cc 42

<210> SEQ ID NO 91
<211> LENGTH: 42
<212> TYPE: DNA
<213> ORGANISM: Artificial
<220> FEATURE:
<223> OTHER INFORMATION: Synthetic construct

<400> SEQUENCE: 91
accctcagag ccgccaccag aaccaccacc agagccgccg cc 42

<210> SEQ ID NO 92
<211> LENGTH: 42
<212> TYPE: DNA
<213> ORGANISM: Artificial
<220> FEATURE:
<223> OTHER INFORMATION: Synthetic construct

<400> SEQUENCE: 92
agcattgaca ggaggttgag gcaggtcaga cgattggcct tg 42

<210> SEQ ID NO 93
<211> LENGTH: 42
<212> TYPE: DNA
<213> ORGANISM: Artificial
<220> FEATURE:
<223> OTHER INFORMATION: Synthetic construct

<400> SEQUENCE: 93
atattcacaa acaaataaat cctcattaaa gccagaatgg aa 42

<210> SEQ ID NO 94
<211> LENGTH: 42
<212> TYPE: DNA
<213> ORGANISM: Artificial
<220> FEATURE:
<223> OTHER INFORMATION: Synthetic construct

<400> SEQUENCE: 94
agcgcagtct ctgaatttac cgttccagta agcgtcatac at 42

<210> SEQ ID NO 95
<211> LENGTH: 42
<212> TYPE: DNA
<213> ORGANISM: Artificial
<220> FEATURE:
<223> OTHER INFORMATION: Synthetic construct

<400> SEQUENCE: 95
ggcttttgat gatacaggag tgtactggta ataagtttta ac 42

<210> SEQ ID NO 96
<211> LENGTH: 42
<212> TYPE: DNA
<213> ORGANISM: Artificial
<220> FEATURE:
<223> OTHER INFORMATION: Synthetic construct

<400> SEQUENCE: 96
ggggtcagtg ccttgagtaa cagtgcccgt ataaacagtt aa 42

<210> SEQ ID NO 97

<211> LENGTH: 42
<212> TYPE: DNA
<213> ORGANISM: Artificial
<220> FEATURE:
<223> OTHER INFORMATION: Synthetic construct

<400> SEQUENCE: 97
tgccccctgc ctatttcgga acctattatt ctgaaacatg aa 42

<210> SEQ ID NO 98
<211> LENGTH: 42
<212> TYPE: DNA
<213> ORGANISM: Artificial
<220> FEATURE:
<223> OTHER INFORMATION: Synthetic construct

<400> SEQUENCE: 98
agtattaaga ggctgagact cctcaagaga aggattagga tt 42

<210> SEQ ID NO 99
<211> LENGTH: 42
<212> TYPE: DNA
<213> ORGANISM: Artificial
<220> FEATURE:
<223> OTHER INFORMATION: Synthetic construct

<400> SEQUENCE: 99
agcggggttt tgctcagtac caggcggata agtgccgtcg ag 42

<210> SEQ ID NO 100
<211> LENGTH: 42
<212> TYPE: DNA
<213> ORGANISM: Artificial
<220> FEATURE:
<223> OTHER INFORMATION: Synthetic construct

<400> SEQUENCE: 100
agggttgata taagtatagc ccggaatagg tgtatcaccg ta 42

<210> SEQ ID NO 101
<211> LENGTH: 42
<212> TYPE: DNA
<213> ORGANISM: Artificial
<220> FEATURE:
<223> OTHER INFORMATION: Synthetic construct

<400> SEQUENCE: 101
ctcaggaggt ttagtaccgc caccctcaga accgccaccc tc 42

<210> SEQ ID NO 102
<211> LENGTH: 42
<212> TYPE: DNA
<213> ORGANISM: Artificial
<220> FEATURE:
<223> OTHER INFORMATION: Synthetic construct

<400> SEQUENCE: 102
agaaccgcca ccctcagagc caccaccctc attttcaggg at 42

<210> SEQ ID NO 103
<211> LENGTH: 42
<212> TYPE: DNA
<213> ORGANISM: Artificial
<220> FEATURE:
<223> OTHER INFORMATION: Synthetic construct

<400> SEQUENCE: 103
agcaagccca ataggaaccc atgtaccgta acactgagtt tc 42

<210> SEQ ID NO 104
<211> LENGTH: 42
<212> TYPE: DNA
<213> ORGANISM: Artificial
<220> FEATURE:
<223> OTHER INFORMATION: Synthetic construct

<400> SEQUENCE: 104
gtcaccagta caaactacaa cgcctgtagc attccacaga ca 42

<210> SEQ ID NO 105
<211> LENGTH: 42
<212> TYPE: DNA
<213> ORGANISM: Artificial
<220> FEATURE:
<223> OTHER INFORMATION: Synthetic construct

<400> SEQUENCE: 105
gccctcatag ttagcgtaac gatctaaagt tttgtcgtct tt 42

<210> SEQ ID NO 106
<211> LENGTH: 42
<212> TYPE: DNA
<213> ORGANISM: Artificial
<220> FEATURE:
<223> OTHER INFORMATION: Synthetic construct

<400> SEQUENCE: 106
ccagacgtta gtaaatgaat tttctgtatg ggattttgct aa 42

<210> SEQ ID NO 107
<211> LENGTH: 42
<212> TYPE: DNA
<213> ORGANISM: Artificial
<220> FEATURE:
<223> OTHER INFORMATION: Synthetic construct

<400> SEQUENCE: 107
acaactttca acagtttcag cggagtgaga atagaaagga ac 42

<210> SEQ ID NO 108
<211> LENGTH: 42
<212> TYPE: DNA
<213> ORGANISM: Artificial
<220> FEATURE:
<223> OTHER INFORMATION: Synthetic construct

<400> SEQUENCE: 108
aactaaagga attgcgaata ataatttttt cacgttgaaa at 42

<210> SEQ ID NO 109
<211> LENGTH: 42
<212> TYPE: DNA
<213> ORGANISM: Artificial
<220> FEATURE:
<223> OTHER INFORMATION: Synthetic construct

<400> SEQUENCE: 109
ctccaaaaaa aaggctccaa aaggagcctt taattgtatc gg 42

<210> SEQ ID NO 110

<211> LENGTH: 42
<212> TYPE: DNA
<213> ORGANISM: Artificial
<220> FEATURE:
<223> OTHER INFORMATION: Synthetic construct

<400> SEQUENCE: 110
tttatcagct tgctttcgag gtgaatttct taaacagctt ga 42

<210> SEQ ID NO 111
<211> LENGTH: 42
<212> TYPE: DNA
<213> ORGANISM: Artificial
<220> FEATURE:
<223> OTHER INFORMATION: Synthetic construct

<400> SEQUENCE: 111
taccgatagt tgcgccgaca atgacaacaa ccatcgccca cg 42

<210> SEQ ID NO 112
<211> LENGTH: 42
<212> TYPE: DNA
<213> ORGANISM: Artificial
<220> FEATURE:
<223> OTHER INFORMATION: Synthetic construct

<400> SEQUENCE: 112
cataaccgat atattcggtc gctgaggctt gcagggagtt aa 42

<210> SEQ ID NO 113
<211> LENGTH: 42
<212> TYPE: DNA
<213> ORGANISM: Artificial
<220> FEATURE:
<223> OTHER INFORMATION: Synthetic construct

<400> SEQUENCE: 113
aggccgcttt tgcgggatcg tcaccctcag cagcgaaaga ca 42

<210> SEQ ID NO 114
<211> LENGTH: 42
<212> TYPE: DNA
<213> ORGANISM: Artificial
<220> FEATURE:
<223> OTHER INFORMATION: Synthetic construct

<400> SEQUENCE: 114
gcatcggaac gagggtagca acggctacag aggctttgag ga 42

<210> SEQ ID NO 115
<211> LENGTH: 42
<212> TYPE: DNA
<213> ORGANISM: Artificial
<220> FEATURE:
<223> OTHER INFORMATION: Synthetic construct

<400> SEQUENCE: 115
ctaaagactt tttcatgagg aagtttccat taaacgggta aa 42

<210> SEQ ID NO 116
<211> LENGTH: 42
<212> TYPE: DNA
<213> ORGANISM: Artificial
<220> FEATURE:
<223> OTHER INFORMATION: Synthetic construct

<400> SEQUENCE: 116
atacgtaatg ccactacgaa ggcaccaacc taaaacgaaa ga 42

<210> SEQ ID NO 117
<211> LENGTH: 42
<212> TYPE: DNA
<213> ORGANISM: Artificial
<220> FEATURE:
<223> OTHER INFORMATION: Synthetic construct

<400> SEQUENCE: 117
ggcaaaagaa tacactaaaa cactcatctt tgacccccag cg 42

<210> SEQ ID NO 118
<211> LENGTH: 42
<212> TYPE: DNA
<213> ORGANISM: Artificial
<220> FEATURE:
<223> OTHER INFORMATION: Synthetic construct

<400> SEQUENCE: 118
attataccaa gcgcgaaaca aagtacaacg gagatttgta tc 42

<210> SEQ ID NO 119
<211> LENGTH: 42
<212> TYPE: DNA
<213> ORGANISM: Artificial
<220> FEATURE:
<223> OTHER INFORMATION: Synthetic construct

<400> SEQUENCE: 119
atcgcctgat aaattgtgtc gaaatccgcg acctgctcca tg 42

<210> SEQ ID NO 120
<211> LENGTH: 42
<212> TYPE: DNA
<213> ORGANISM: Artificial
<220> FEATURE:
<223> OTHER INFORMATION: Synthetic construct

<400> SEQUENCE: 120
ttacttagcc ggaacgaggc gcagacggtc aatcataagg ga 42

<210> SEQ ID NO 121
<211> LENGTH: 42
<212> TYPE: DNA
<213> ORGANISM: Artificial
<220> FEATURE:
<223> OTHER INFORMATION: Synthetic construct

<400> SEQUENCE: 121
accgaactga ccaactttga aagaggacag atgaacggtg ta 42

<210> SEQ ID NO 122
<211> LENGTH: 42
<212> TYPE: DNA
<213> ORGANISM: Artificial
<220> FEATURE:
<223> OTHER INFORMATION: Synthetic construct

<400> SEQUENCE: 122
cagaccaggc gcataggctg gctgaccttc atcaagagta at 42

<210> SEQ ID NO 123

<211> LENGTH: 42
<212> TYPE: DNA
<213> ORGANISM: Artificial
<220> FEATURE:
<223> OTHER INFORMATION: Synthetic construct

<400> SEQUENCE: 123
cttgacaaga accggatatt cattacccaa atcaacgtaa ca 42

<210> SEQ ID NO 124
<211> LENGTH: 42
<212> TYPE: DNA
<213> ORGANISM: Artificial
<220> FEATURE:
<223> OTHER INFORMATION: Synthetic construct

<400> SEQUENCE: 124
aagctgctca ttcagtgaat aaggcttgcc ctgacgagaa ac 42

<210> SEQ ID NO 125
<211> LENGTH: 42
<212> TYPE: DNA
<213> ORGANISM: Artificial
<220> FEATURE:
<223> OTHER INFORMATION: Synthetic construct

<400> SEQUENCE: 125
accagaacga gtagtaaatt gggcttgaga tggtttaatt tc 42

<210> SEQ ID NO 126
<211> LENGTH: 42
<212> TYPE: DNA
<213> ORGANISM: Artificial
<220> FEATURE:
<223> OTHER INFORMATION: Synthetic construct

<400> SEQUENCE: 126
aactttaatc attgtgaatt accttatgcg attttaagaa ct 42

<210> SEQ ID NO 127
<211> LENGTH: 42
<212> TYPE: DNA
<213> ORGANISM: Artificial
<220> FEATURE:
<223> OTHER INFORMATION: Synthetic construct

<400> SEQUENCE: 127
ggctcattat accagtcagg acgttgggaa gaaaaatcta cg 42

<210> SEQ ID NO 128
<211> LENGTH: 42
<212> TYPE: DNA
<213> ORGANISM: Artificial
<220> FEATURE:
<223> OTHER INFORMATION: Synthetic construct

<400> SEQUENCE: 128
ttaataaaac gaactaacgg aacaacatta ttacaggtag aa 42

<210> SEQ ID NO 129
<211> LENGTH: 42
<212> TYPE: DNA
<213> ORGANISM: Artificial
<220> FEATURE:
<223> OTHER INFORMATION: Synthetic construct

<400> SEQUENCE: 129
agattcatca gttgagattt aggaatacca cattcaacta at 42

<210> SEQ ID NO 130
<211> LENGTH: 42
<212> TYPE: DNA
<213> ORGANISM: Artificial
<220> FEATURE:
<223> OTHER INFORMATION: Synthetic construct

<400> SEQUENCE: 130
gcagatacat aacgccaaaa ggaattacga ggcatagtaa ga 42

<210> SEQ ID NO 131
<211> LENGTH: 42
<212> TYPE: DNA
<213> ORGANISM: Artificial
<220> FEATURE:
<223> OTHER INFORMATION: Synthetic construct

<400> SEQUENCE: 131
gcaacactat cataaccctc gtttaccaga cgacgataaa aa 42

<210> SEQ ID NO 132
<211> LENGTH: 42
<212> TYPE: DNA
<213> ORGANISM: Artificial
<220> FEATURE:
<223> OTHER INFORMATION: Synthetic construct

<400> SEQUENCE: 132
ccaaaatagc gagaggcttt tgcaaaagaa gttttgccag ag 42

<210> SEQ ID NO 133
<211> LENGTH: 42
<212> TYPE: DNA
<213> ORGANISM: Artificial
<220> FEATURE:
<223> OTHER INFORMATION: Synthetic construct

<400> SEQUENCE: 133
ggggtaatag taaaatgttt agactggata gcgtccaata ct 42

<210> SEQ ID NO 134
<211> LENGTH: 42
<212> TYPE: DNA
<213> ORGANISM: Artificial
<220> FEATURE:
<223> OTHER INFORMATION: Synthetic construct

<400> SEQUENCE: 134
gcggaatcgt cataaatatt cattgaatcc ccctcaaatg ct 42

<210> SEQ ID NO 135
<211> LENGTH: 42
<212> TYPE: DNA
<213> ORGANISM: Artificial
<220> FEATURE:
<223> OTHER INFORMATION: Synthetic construct

<400> SEQUENCE: 135
ttaaacagtt cagaaaacga gaatgaccat aaatcaaaaa tc 42

<210> SEQ ID NO 136

<211> LENGTH: 42
<212> TYPE: DNA
<213> ORGANISM: Artificial
<220> FEATURE:
<223> OTHER INFORMATION: Synthetic construct

<400> SEQUENCE: 136
aggtctttac cctgactatt atagtcagaa gcaaagcgga tt 42

<210> SEQ ID NO 137
<211> LENGTH: 42
<212> TYPE: DNA
<213> ORGANISM: Artificial
<220> FEATURE:
<223> OTHER INFORMATION: Synthetic construct

<400> SEQUENCE: 137
gcatcaaaaa gattaagagg aagcccgaaa gacttcaaat at 42

<210> SEQ ID NO 138
<211> LENGTH: 42
<212> TYPE: DNA
<213> ORGANISM: Artificial
<220> FEATURE:
<223> OTHER INFORMATION: Synthetic construct

<400> SEQUENCE: 138
cgcgttttaa ttcgagcttc aaagcgaacc agaccggaag ca 42

<210> SEQ ID NO 139
<211> LENGTH: 42
<212> TYPE: DNA
<213> ORGANISM: Artificial
<220> FEATURE:
<223> OTHER INFORMATION: Synthetic construct

<400> SEQUENCE: 139
aactccaaca ggtcaggatt agagagtacc tttaattgct cc 42

<210> SEQ ID NO 140
<211> LENGTH: 42
<212> TYPE: DNA
<213> ORGANISM: Artificial
<220> FEATURE:
<223> OTHER INFORMATION: Synthetic construct

<400> SEQUENCE: 140
ttttgataag aggtcatttt tgcggatggc ttagagctta at 42

<210> SEQ ID NO 141
<211> LENGTH: 42
<212> TYPE: DNA
<213> ORGANISM: Artificial
<220> FEATURE:
<223> OTHER INFORMATION: Synthetic construct

<400> SEQUENCE: 141
tgctgaatat aatgctgtag ctcaacatgt tttaaatatg ca 42

<210> SEQ ID NO 142
<211> LENGTH: 42
<212> TYPE: DNA
<213> ORGANISM: Artificial
<220> FEATURE:
<223> OTHER INFORMATION: Synthetic construct

<400> SEQUENCE: 142
actaaagtac ggtgtctgga agtttcattc catataacag tt 42

<210> SEQ ID NO 143
<211> LENGTH: 42
<212> TYPE: DNA
<213> ORGANISM: Artificial
<220> FEATURE:
<223> OTHER INFORMATION: Synthetic construct

<400> SEQUENCE: 143
gattcccaat tctgcgaacg agtagattta gtttgaccat ta 42

<210> SEQ ID NO 144
<211> LENGTH: 42
<212> TYPE: DNA
<213> ORGANISM: Artificial
<220> FEATURE:
<223> OTHER INFORMATION: Synthetic construct

<400> SEQUENCE: 144
gatacatttc gcaaatggtc aataacctgt ttagctatat tt 42

<210> SEQ ID NO 145
<211> LENGTH: 42
<212> TYPE: DNA
<213> ORGANISM: Artificial
<220> FEATURE:
<223> OTHER INFORMATION: Synthetic construct

<400> SEQUENCE: 145
tcatttgggg cgcgagctga aaaggtggca tcaattctac ta 42

<210> SEQ ID NO 146
<211> LENGTH: 42
<212> TYPE: DNA
<213> ORGANISM: Artificial
<220> FEATURE:
<223> OTHER INFORMATION: Synthetic construct

<400> SEQUENCE: 146
atagtagtag cattaacatc caataaatca tacaggcaag gc 42

<210> SEQ ID NO 147
<211> LENGTH: 42
<212> TYPE: DNA
<213> ORGANISM: Artificial
<220> FEATURE:
<223> OTHER INFORMATION: Synthetic construct

<400> SEQUENCE: 147
aaagaattag caaaattaag caataaagcc tcagagcata aa 42

<210> SEQ ID NO 148
<211> LENGTH: 42
<212> TYPE: DNA
<213> ORGANISM: Artificial
<220> FEATURE:
<223> OTHER INFORMATION: Synthetic construct

<400> SEQUENCE: 148
gctaaatcgg ttgtaccaaa aacattatga ccctgtaata ct 42

<210> SEQ ID NO 149

<211> LENGTH: 42
<212> TYPE: DNA
<213> ORGANISM: Artificial
<220> FEATURE:
<223> OTHER INFORMATION: Synthetic construct

<400> SEQUENCE: 149
tttgcgggag aagcctttat ttcaacgcaa ggataaaaat tt 42

<210> SEQ ID NO 150
<211> LENGTH: 42
<212> TYPE: DNA
<213> ORGANISM: Artificial
<220> FEATURE:
<223> OTHER INFORMATION: Synthetic construct

<400> SEQUENCE: 150
ttagaaccct catatatttt aaatgcaatg cctgagtaat gt 42

<210> SEQ ID NO 151
<211> LENGTH: 42
<212> TYPE: DNA
<213> ORGANISM: Artificial
<220> FEATURE:
<223> OTHER INFORMATION: Synthetic construct

<400> SEQUENCE: 151
gtaggtaaag attcaaaagg gtgagaaagg ccggagacag tc 42

<210> SEQ ID NO 152
<211> LENGTH: 42
<212> TYPE: DNA
<213> ORGANISM: Artificial
<220> FEATURE:
<223> OTHER INFORMATION: Synthetic construct

<400> SEQUENCE: 152
aaatcaccat caatatgata ttcaaccgtt ctagctgata aa 42

<210> SEQ ID NO 153
<211> LENGTH: 42
<212> TYPE: DNA
<213> ORGANISM: Artificial
<220> FEATURE:
<223> OTHER INFORMATION: Synthetic construct

<400> SEQUENCE: 153
ttaatgccgg agagggtagc tatttttgag agatctacaa ag 42

<210> SEQ ID NO 154
<211> LENGTH: 42
<212> TYPE: DNA
<213> ORGANISM: Artificial
<220> FEATURE:
<223> OTHER INFORMATION: Synthetic construct

<400> SEQUENCE: 154
gctatcaggt cattgcctga gagtctggag caaacaagag aa 42

<210> SEQ ID NO 155
<211> LENGTH: 42
<212> TYPE: DNA
<213> ORGANISM: Artificial
<220> FEATURE:
<223> OTHER INFORMATION: Synthetic construct

<400> SEQUENCE: 155
tcgatgaacg gtaatcgtaa aactagcatg tcaatcatat gt 42

<210> SEQ ID NO 156
<211> LENGTH: 42
<212> TYPE: DNA
<213> ORGANISM: Artificial
<220> FEATURE:
<223> OTHER INFORMATION: Synthetic construct

<400> SEQUENCE: 156
accccggttg ataatcagaa aagccccaaa aacaggaaga tt 42

<210> SEQ ID NO 157
<211> LENGTH: 42
<212> TYPE: DNA
<213> ORGANISM: Artificial
<220> FEATURE:
<223> OTHER INFORMATION: Synthetic construct

<400> SEQUENCE: 157
gtataagcaa atatttaaat tgtaaacgtt aatattttgt ta 42

<210> SEQ ID NO 158
<211> LENGTH: 42
<212> TYPE: DNA
<213> ORGANISM: Artificial
<220> FEATURE:
<223> OTHER INFORMATION: Synthetic construct

<400> SEQUENCE: 158
aaattcgcat taaatttttg ttaaatcagc tcatttttta ac 42

<210> SEQ ID NO 159
<211> LENGTH: 42
<212> TYPE: DNA
<213> ORGANISM: Artificial
<220> FEATURE:
<223> OTHER INFORMATION: Synthetic construct

<400> SEQUENCE: 159
caataggaac gccatcaaaa ataattcgcg tctggccttc ct 42

<210> SEQ ID NO 160
<211> LENGTH: 42
<212> TYPE: DNA
<213> ORGANISM: Artificial
<220> FEATURE:
<223> OTHER INFORMATION: Synthetic construct

<400> SEQUENCE: 160
gtagccagct ttcatcaaca ttaaatgtga gcgagtaaca ac 42

<210> SEQ ID NO 161
<211> LENGTH: 42
<212> TYPE: DNA
<213> ORGANISM: Artificial
<220> FEATURE:
<223> OTHER INFORMATION: Synthetic construct

<400> SEQUENCE: 161
ccgtcggatt ctccgtggga acaaacggcg gattgaccgt aa 42

<210> SEQ ID NO 162

<211> LENGTH: 42
<212> TYPE: DNA
<213> ORGANISM: Artificial
<220> FEATURE:
<223> OTHER INFORMATION: Synthetic construct

<400> SEQUENCE: 162
tgggataggt cacgttggtg tagatgggcg catcgtaacc gt 42

<210> SEQ ID NO 163
<211> LENGTH: 42
<212> TYPE: DNA
<213> ORGANISM: Artificial
<220> FEATURE:
<223> OTHER INFORMATION: Synthetic construct

<400> SEQUENCE: 163
gcatctgcca gtttgagggg acgacgacag tatcggcctc ag 42

<210> SEQ ID NO 164
<211> LENGTH: 42
<212> TYPE: DNA
<213> ORGANISM: Artificial
<220> FEATURE:
<223> OTHER INFORMATION: Synthetic construct

<400> SEQUENCE: 164
gaagatcgca ctccagccag ctttccggca ccgcttctgg tg 42

<210> SEQ ID NO 165
<211> LENGTH: 42
<212> TYPE: DNA
<213> ORGANISM: Artificial
<220> FEATURE:
<223> OTHER INFORMATION: Synthetic construct

<400> SEQUENCE: 165
ccggaaacca ggcaaagcgc cattcgccat tcaggctgcg ca 42

<210> SEQ ID NO 166
<211> LENGTH: 42
<212> TYPE: DNA
<213> ORGANISM: Artificial
<220> FEATURE:
<223> OTHER INFORMATION: Synthetic construct

<400> SEQUENCE: 166
actgttggga agggcgatcg gtgcgggcct cttcgctatt ac 42

<210> SEQ ID NO 167
<211> LENGTH: 42
<212> TYPE: DNA
<213> ORGANISM: Artificial
<220> FEATURE:
<223> OTHER INFORMATION: Synthetic construct

<400> SEQUENCE: 167
gccagctggc gaaaggggga tgtgctgcaa ggcgattaag tt 42

<210> SEQ ID NO 168
<211> LENGTH: 42
<212> TYPE: DNA
<213> ORGANISM: Artificial
<220> FEATURE:
<223> OTHER INFORMATION: Synthetic construct

<400> SEQUENCE: 168
gggtaacgcc agggttttcc cagtcacgac gttgtaaaac ga 42

<210> SEQ ID NO 169
<211> LENGTH: 42
<212> TYPE: DNA
<213> ORGANISM: Artificial
<220> FEATURE:
<223> OTHER INFORMATION: Synthetic construct

<400> SEQUENCE: 169
cggccagtgc caagctttca gaggtggagc cgccacggga ac 42

<210> SEQ ID NO 170
<211> LENGTH: 42
<212> TYPE: DNA
<213> ORGANISM: Artificial
<220> FEATURE:
<223> OTHER INFORMATION: Synthetic construct

<400> SEQUENCE: 170
ggataacctc accggaaaca atcggcgaaa cgtacagcgc ca 42

<210> SEQ ID NO 171
<211> LENGTH: 42
<212> TYPE: DNA
<213> ORGANISM: Artificial
<220> FEATURE:
<223> OTHER INFORMATION: Synthetic construct

<400> SEQUENCE: 171
tgtttaccag tcccggaatt tgtgagagat agactttctc cg 42

<210> SEQ ID NO 172
<211> LENGTH: 42
<212> TYPE: DNA
<213> ORGANISM: Artificial
<220> FEATURE:
<223> OTHER INFORMATION: Synthetic construct

<400> SEQUENCE: 172
tggtgaaggg atagctctca cggaaaaaga gacgcagaaa ca 42

<210> SEQ ID NO 173
<211> LENGTH: 42
<212> TYPE: DNA
<213> ORGANISM: Artificial
<220> FEATURE:
<223> OTHER INFORMATION: Synthetic construct

<400> SEQUENCE: 173
gcggatcaaa cttaaatttc tgctcatttg ccgccagcag tt 42

<210> SEQ ID NO 174
<211> LENGTH: 42
<212> TYPE: DNA
<213> ORGANISM: Artificial
<220> FEATURE:
<223> OTHER INFORMATION: Synthetic construct

<400> SEQUENCE: 174
gggcggttgt gtacatcgac ataaaaaaat cccgtaaaaa aa 42

<210> SEQ ID NO 175

<211> LENGTH: 42
<212> TYPE: DNA
<213> ORGANISM: Artificial
<220> FEATURE:
<223> OTHER INFORMATION: Synthetic construct

<400> SEQUENCE: 175
gccgcacagg cggcctttag tgatgaaggg taaagttaaa cg 42

<210> SEQ ID NO 176
<211> LENGTH: 42
<212> TYPE: DNA
<213> ORGANISM: Artificial
<220> FEATURE:
<223> OTHER INFORMATION: Synthetic construct

<400> SEQUENCE: 176
atgctgattg ccgttccggc aaacgcggtc cgtttttttcg tc 42

<210> SEQ ID NO 177
<211> LENGTH: 42
<212> TYPE: DNA
<213> ORGANISM: Artificial
<220> FEATURE:
<223> OTHER INFORMATION: Synthetic construct

<400> SEQUENCE: 177
tcgtcgctgg cagcctccgg ccagagcaca tcctcataac gg 42

<210> SEQ ID NO 178
<211> LENGTH: 42
<212> TYPE: DNA
<213> ORGANISM: Artificial
<220> FEATURE:
<223> OTHER INFORMATION: Synthetic construct

<400> SEQUENCE: 178
aacgtgccgg acttgtagaa cgtcagcgtg gtgctggtct gg 42

<210> SEQ ID NO 179
<211> LENGTH: 42
<212> TYPE: DNA
<213> ORGANISM: Artificial
<220> FEATURE:
<223> OTHER INFORMATION: Synthetic construct

<400> SEQUENCE: 179
tcagcagcaa ccgcaagaat gccaacggca gcaccgtcgg tg 42

<210> SEQ ID NO 180
<211> LENGTH: 42
<212> TYPE: DNA
<213> ORGANISM: Artificial
<220> FEATURE:
<223> OTHER INFORMATION: Synthetic construct

<400> SEQUENCE: 180
gtgccatccc acgcaaccag cttacggctg gaggtgtcca gc 42

<210> SEQ ID NO 181
<211> LENGTH: 42
<212> TYPE: DNA
<213> ORGANISM: Artificial
<220> FEATURE:
<223> OTHER INFORMATION: Synthetic construct

<400> SEQUENCE: 181
atcagcgggg tcattgcagg cgctttcgca ctcaatccgc cg 42

<210> SEQ ID NO 182
<211> LENGTH: 42
<212> TYPE: DNA
<213> ORGANISM: Artificial
<220> FEATURE:
<223> OTHER INFORMATION: Synthetic construct

<400> SEQUENCE: 182
ggcgcggttg cggtatgagc cgggtcactg ttgccctgcg gc 42

<210> SEQ ID NO 183
<211> LENGTH: 42
<212> TYPE: DNA
<213> ORGANISM: Artificial
<220> FEATURE:
<223> OTHER INFORMATION: Synthetic construct

<400> SEQUENCE: 183
tggtaatggg taaaggtttc tttgctcgtc ataaacatcc ct 42

<210> SEQ ID NO 184
<211> LENGTH: 42
<212> TYPE: DNA
<213> ORGANISM: Artificial
<220> FEATURE:
<223> OTHER INFORMATION: Synthetic construct

<400> SEQUENCE: 184
tacactggtg tgttcagcaa atcgttaacg gcatcagatg cc 42

<210> SEQ ID NO 185
<211> LENGTH: 42
<212> TYPE: DNA
<213> ORGANISM: Artificial
<220> FEATURE:
<223> OTHER INFORMATION: Synthetic construct

<400> SEQUENCE: 185
gggttacctg cagccagcgg tgccggtgcc ccctgcatca ga 42

<210> SEQ ID NO 186
<211> LENGTH: 42
<212> TYPE: DNA
<213> ORGANISM: Artificial
<220> FEATURE:
<223> OTHER INFORMATION: Synthetic construct

<400> SEQUENCE: 186
cgatccagcg cagtgtcact gcgcgcctgt gcactctgtg gt 42

<210> SEQ ID NO 187
<211> LENGTH: 42
<212> TYPE: DNA
<213> ORGANISM: Artificial
<220> FEATURE:
<223> OTHER INFORMATION: Synthetic construct

<400> SEQUENCE: 187
gctgcggcca gaatgcggcg ggccgttttc acggtcatac cg 42

<210> SEQ ID NO 188

<211> LENGTH: 42
<212> TYPE: DNA
<213> ORGANISM: Artificial
<220> FEATURE:
<223> OTHER INFORMATION: Synthetic construct

<400> SEQUENCE: 188
ggggtttctg ccagcacgcg tgcctgttct tcgcgtccgt ga 42

<210> SEQ ID NO 189
<211> LENGTH: 42
<212> TYPE: DNA
<213> ORGANISM: Artificial
<220> FEATURE:
<223> OTHER INFORMATION: Synthetic construct

<400> SEQUENCE: 189
gcctcctcac agttgaggat ccccgggtac cgagctcgaa tt 42

<210> SEQ ID NO 190
<211> LENGTH: 42
<212> TYPE: DNA
<213> ORGANISM: Artificial
<220> FEATURE:
<223> OTHER INFORMATION: Synthetic construct

<400> SEQUENCE: 190
cgtaatcatg gtcatagctg tttcctgtgt gaaattgtta tc 42

<210> SEQ ID NO 191
<211> LENGTH: 42
<212> TYPE: DNA
<213> ORGANISM: Artificial
<220> FEATURE:
<223> OTHER INFORMATION: Synthetic construct

<400> SEQUENCE: 191
cgctcacaat tccacacaac atacgagccg gaagcataaa gt 42

<210> SEQ ID NO 192
<211> LENGTH: 42
<212> TYPE: DNA
<213> ORGANISM: Artificial
<220> FEATURE:
<223> OTHER INFORMATION: Synthetic construct

<400> SEQUENCE: 192
gtaaagcctg gggtgcctaa tgagtgagct aactcacatt aa 42

<210> SEQ ID NO 193
<211> LENGTH: 42
<212> TYPE: DNA
<213> ORGANISM: Artificial
<220> FEATURE:
<223> OTHER INFORMATION: Synthetic construct

<400> SEQUENCE: 193
ttgcgttgcg ctcactgccc gctttccagt cgggaaacct gt 42

<210> SEQ ID NO 194
<211> LENGTH: 42
<212> TYPE: DNA
<213> ORGANISM: Artificial
<220> FEATURE:
<223> OTHER INFORMATION: Synthetic construct

<400> SEQUENCE: 194
cgtgccagct gcattaatga atcggccaac gcgcggggag ag 42

<210> SEQ ID NO 195
<211> LENGTH: 42
<212> TYPE: DNA
<213> ORGANISM: Artificial
<220> FEATURE:
<223> OTHER INFORMATION: Synthetic construct

<400> SEQUENCE: 195
gcggtttgcg tattgggcgc cagggtggtt tttcttttca cc 42

<210> SEQ ID NO 196
<211> LENGTH: 42
<212> TYPE: DNA
<213> ORGANISM: Artificial
<220> FEATURE:
<223> OTHER INFORMATION: Synthetic construct

<400> SEQUENCE: 196
agtgagacgg gcaacagctg attgcccttc accgcctggc cc 42

<210> SEQ ID NO 197
<211> LENGTH: 42
<212> TYPE: DNA
<213> ORGANISM: Artificial
<220> FEATURE:
<223> OTHER INFORMATION: Synthetic construct

<400> SEQUENCE: 197
tgagagagtt gcagcaagcg gtccacgctg gtttgcccca gc 42

<210> SEQ ID NO 198
<211> LENGTH: 42
<212> TYPE: DNA
<213> ORGANISM: Artificial
<220> FEATURE:
<223> OTHER INFORMATION: Synthetic construct

<400> SEQUENCE: 198
aggcgaaaat cctgtttgat ggtggttccg aaatcggcaa aa 42

<210> SEQ ID NO 199
<211> LENGTH: 42
<212> TYPE: DNA
<213> ORGANISM: Artificial
<220> FEATURE:
<223> OTHER INFORMATION: Synthetic construct

<400> SEQUENCE: 199
tcccttataa atcaaaagaa tagcccgaga tagggttgag tg 42

<210> SEQ ID NO 200
<211> LENGTH: 42
<212> TYPE: DNA
<213> ORGANISM: Artificial
<220> FEATURE:
<223> OTHER INFORMATION: Synthetic construct

<400> SEQUENCE: 200
ttgttccagt ttggaacaag agtccactat taaagaacgt gg 42

<210> SEQ ID NO 201

<211> LENGTH: 42
<212> TYPE: DNA
<213> ORGANISM: Artificial
<220> FEATURE:
<223> OTHER INFORMATION: Synthetic construct

<400> SEQUENCE: 201
actccaacgt caaagggcga aaaaccgtct atcagggcga tg 42

<210> SEQ ID NO 202
<211> LENGTH: 42
<212> TYPE: DNA
<213> ORGANISM: Artificial
<220> FEATURE:
<223> OTHER INFORMATION: Synthetic construct

<400> SEQUENCE: 202
gcccactacg tgaaccatca cccaaatcaa gttttttggg gt 42

<210> SEQ ID NO 203
<211> LENGTH: 42
<212> TYPE: DNA
<213> ORGANISM: Artificial
<220> FEATURE:
<223> OTHER INFORMATION: Synthetic construct

<400> SEQUENCE: 203
cgaggtgccg taaagcacta aatcggaacc ctaaagggag cc 42

<210> SEQ ID NO 204
<211> LENGTH: 42
<212> TYPE: DNA
<213> ORGANISM: Artificial
<220> FEATURE:
<223> OTHER INFORMATION: Synthetic construct

<400> SEQUENCE: 204
cccgatttag agcttgacgg ggaaagccgg cgaacgtggc ga 42

<210> SEQ ID NO 205
<211> LENGTH: 42
<212> TYPE: DNA
<213> ORGANISM: Artificial
<220> FEATURE:
<223> OTHER INFORMATION: Synthetic construct

<400> SEQUENCE: 205
gaaaggaagg gaagaaagcg aaaggagcgg gcgctagggc gc 42

<210> SEQ ID NO 206
<211> LENGTH: 42
<212> TYPE: DNA
<213> ORGANISM: Artificial
<220> FEATURE:
<223> OTHER INFORMATION: Synthetic construct

<400> SEQUENCE: 206
tggcaagtgt agcggtcacg ctgcgcgtaa ccaccacacc cg 42

<210> SEQ ID NO 207
<211> LENGTH: 22
<212> TYPE: DNA
<213> ORGANISM: Artificial
<220> FEATURE:
<223> OTHER INFORMATION: Synthetic construct

<400> SEQUENCE: 207
ccgcgcttaa tgcgccgcta ca 22

<210> SEQ ID NO 208
<211> LENGTH: 77
<212> TYPE: DNA
<213> ORGANISM: Artificial
<220> FEATURE:
<223> OTHER INFORMATION: Synthetic construct

<400> SEQUENCE: 208
aatcctccat cccttcctta atcctccatc ccttccttaa tcctccatcc cttcctttag 60
tggagataat ggattgg 77

<210> SEQ ID NO 209
<211> LENGTH: 75
<212> TYPE: DNA
<213> ORGANISM: Artificial
<220> FEATURE:
<223> OTHER INFORMATION: Synthetic construct

<400> SEQUENCE: 209
ggaagggatg gaggattgat ctactatagc actgcttgat ctactatagc actgcttgat 60
ctactatagc actgc 75

<210> SEQ ID NO 210
<211> LENGTH: 78
<212> TYPE: DNA
<213> ORGANISM: Artificial
<220> FEATURE:
<223> OTHER INFORMATION: Synthetic construct

<400> SEQUENCE: 210
tacgtgcttt tacaggtgtt tacgtgcttt tacaggtgtt tacgtgcttt tacaggtgtt 60
gcagtgctat agtagatc 78

<210> SEQ ID NO 211
<211> LENGTH: 78
<212> TYPE: DNA
<213> ORGANISM: Artificial
<220> FEATURE:
<223> OTHER INFORMATION: Synthetic construct

<400> SEQUENCE: 211
cacctgtaaa agcacgtatt gagcctactt agttgtactt gagcctactt agttgtactt 60
gagcctactt agttgtac 78

<210> SEQ ID NO 212
<211> LENGTH: 78
<212> TYPE: DNA
<213> ORGANISM: Artificial
<220> FEATURE:
<223> OTHER INFORMATION: Synthetic construct

<400> SEQUENCE: 212
tctatgctac tgactaggtt tctatgctac tgactaggtt tctatgctac tgactaggtt 60
gtacaactaa gtaggctc 78

<210> SEQ ID NO 213
<211> LENGTH: 80
<212> TYPE: DNA

<213> ORGANISM: Artificial
<220> FEATURE:
<223> OTHER INFORMATION: Synthetic construct

<400> SEQUENCE: 213
cctagtcagt agcatagatt ccaatccatt atctccacta ccaatccatt atctccacta 60
ccaatccatt atctccacta 80

<210> SEQ ID NO 214
<211> LENGTH: 64
<212> TYPE: DNA
<213> ORGANISM: Artificial
<220> FEATURE:
<223> OTHER INFORMATION: Synthetic construct

<400> SEQUENCE: 214
cgggagctaa acaggaggcc gattaaaggg attttagaca ggttccaatc cattatctcc 60
acta 64

<210> SEQ ID NO 215
<211> LENGTH: 64
<212> TYPE: DNA
<213> ORGANISM: Artificial
<220> FEATURE:
<223> OTHER INFORMATION: Synthetic construct

<400> SEQUENCE: 215
aacggtacgc cagaatcctg agaagtgttt ttataatcag tgttccaatc cattatctcc 60
acta 64

<210> SEQ ID NO 216
<211> LENGTH: 64
<212> TYPE: DNA
<213> ORGANISM: Artificial
<220> FEATURE:
<223> OTHER INFORMATION: Synthetic construct

<400> SEQUENCE: 216
aggccaccga gtaaaagagt ctgtccatca cgcaaattaa ccttccaatc cattatctcc 60
acta 64

<210> SEQ ID NO 217
<211> LENGTH: 64
<212> TYPE: DNA
<213> ORGANISM: Artificial
<220> FEATURE:
<223> OTHER INFORMATION: Synthetic construct

<400> SEQUENCE: 217
gttgtagcaa tacttctttg attagtaata acatcacttg ccttccaatc cattatctcc 60
acta 64

<210> SEQ ID NO 218
<211> LENGTH: 64
<212> TYPE: DNA
<213> ORGANISM: Artificial
<220> FEATURE:
<223> OTHER INFORMATION: Synthetic construct

<400> SEQUENCE: 218
tgagtagaag aactcaaact atcggccttg ctggtaatat ccttccaatc cattatctcc 60
acta 64

<210> SEQ ID NO 219
<211> LENGTH: 64
<212> TYPE: DNA
<213> ORGANISM: Artificial
<220> FEATURE:
<223> OTHER INFORMATION: Synthetic construct

<400> SEQUENCE: 219
agaacaatat taccgccagc cattgcaaca ggaaaaacgc tcttccaatc cattatctcc 60
acta 64

<210> SEQ ID NO 220
<211> LENGTH: 64
<212> TYPE: DNA
<213> ORGANISM: Artificial
<220> FEATURE:
<223> OTHER INFORMATION: Synthetic construct

<400> SEQUENCE: 220
atggaaatac ctacattttg acgctcaatc gtctgaaatg gattccaatc cattatctcc 60
acta 64

<210> SEQ ID NO 221
<211> LENGTH: 64
<212> TYPE: DNA
<213> ORGANISM: Artificial
<220> FEATURE:
<223> OTHER INFORMATION: Synthetic construct

<400> SEQUENCE: 221
ttatttacat tggcagattc accagtcaca cgaccagtaa tattccaatc cattatctcc 60
acta 64

<210> SEQ ID NO 222
<211> LENGTH: 64
<212> TYPE: DNA
<213> ORGANISM: Artificial
<220> FEATURE:
<223> OTHER INFORMATION: Synthetic construct

<400> SEQUENCE: 222
aaagggacat tctggccaac agagatagaa cccttctgac ctttccaatc cattatctcc 60
acta 64

<210> SEQ ID NO 223
<211> LENGTH: 64
<212> TYPE: DNA
<213> ORGANISM: Artificial
<220> FEATURE:
<223> OTHER INFORMATION: Synthetic construct

<400> SEQUENCE: 223
gaaagcgtaa gaatacgtgg cacagacaat atttttgaat ggttccaatc cattatctcc 60
acta 64

<210> SEQ ID NO 224
<211> LENGTH: 64
<212> TYPE: DNA
<213> ORGANISM: Artificial
<220> FEATURE:
<223> OTHER INFORMATION: Synthetic construct

<400> SEQUENCE: 224
ctattagtct ttaatgcgcg aactgatagc cctaaaacat cgttccaatc cattatctcc 60
acta 64

<210> SEQ ID NO 225
<211> LENGTH: 64
<212> TYPE: DNA
<213> ORGANISM: Artificial
<220> FEATURE:
<223> OTHER INFORMATION: Synthetic construct

<400> SEQUENCE: 225
ccattaaaaa taccgaacga accaccagca gaagataaaa cattccaatc cattatctcc 60
acta 64

<210> SEQ ID NO 226
<211> LENGTH: 64
<212> TYPE: DNA
<213> ORGANISM: Artificial
<220> FEATURE:
<223> OTHER INFORMATION: Synthetic construct

<400> SEQUENCE: 226
gaggtgaggc ggtcagtatt aacaccgcct gcaacagtgc cattccaatc cattatctcc 60
acta 64

<210> SEQ ID NO 227
<211> LENGTH: 64
<212> TYPE: DNA
<213> ORGANISM: Artificial
<220> FEATURE:
<223> OTHER INFORMATION: Synthetic construct

<400> SEQUENCE: 227
cgctgagagc cagcagcaaa tgaaaaatct aaagcatcac ctttccaatc cattatctcc 60
acta 64

<210> SEQ ID NO 228
<211> LENGTH: 64
<212> TYPE: DNA
<213> ORGANISM: Artificial
<220> FEATURE:
<223> OTHER INFORMATION: Synthetic construct

<400> SEQUENCE: 228
tgctgaacct caaatatcaa accctcaatc aatatctggt cattccaatc cattatctcc 60
acta 64

<210> SEQ ID NO 229
<211> LENGTH: 64
<212> TYPE: DNA
<213> ORGANISM: Artificial
<220> FEATURE:
<223> OTHER INFORMATION: Synthetic construct

<400> SEQUENCE: 229
gttggcaaat caacagttga aaggaattga ggaaggttat ctttccaatc cattatctcc 60
acta 64

<210> SEQ ID NO 230
<211> LENGTH: 64

<212> TYPE: DNA
<213> ORGANISM: Artificial
<220> FEATURE:
<223> OTHER INFORMATION: Synthetic construct

<400> SEQUENCE: 230
aaaatatctt taggagcact aacaactaat agattagagc cgttccaatc cattatctcc 60
acta 64

<210> SEQ ID NO 231
<211> LENGTH: 64
<212> TYPE: DNA
<213> ORGANISM: Artificial
<220> FEATURE:
<223> OTHER INFORMATION: Synthetic construct

<400> SEQUENCE: 231
tcaatagata atacatttga ggatttagaa gtattagact ttttccaatc cattatctcc 60
acta 64

<210> SEQ ID NO 232
<211> LENGTH: 64
<212> TYPE: DNA
<213> ORGANISM: Artificial
<220> FEATURE:
<223> OTHER INFORMATION: Synthetic construct

<400> SEQUENCE: 232
acaaacaatt cgacaactcg tattaaatcc tttgcccgaa cgttccaatc cattatctcc 60
acta 64

<210> SEQ ID NO 233
<211> LENGTH: 64
<212> TYPE: DNA
<213> ORGANISM: Artificial
<220> FEATURE:
<223> OTHER INFORMATION: Synthetic construct

<400> SEQUENCE: 233
ttattaattt taaaagtttg agtaacatta tcattttgcg gattccaatc cattatctcc 60
acta 64

<210> SEQ ID NO 234
<211> LENGTH: 64
<212> TYPE: DNA
<213> ORGANISM: Artificial
<220> FEATURE:
<223> OTHER INFORMATION: Synthetic construct

<400> SEQUENCE: 234
acaaagaaac caccagaagg agcggaatta tcatcatatt ccttccaatc cattatctcc 60
acta 64

<210> SEQ ID NO 235
<211> LENGTH: 64
<212> TYPE: DNA
<213> ORGANISM: Artificial
<220> FEATURE:
<223> OTHER INFORMATION: Synthetic construct

<400> SEQUENCE: 235
tgattatcag atgatggcaa ttcatcaata taatcctgat tgttccaatc cattatctcc 60
acta 64

<210> SEQ ID NO 236
<211> LENGTH: 64
<212> TYPE: DNA
<213> ORGANISM: Artificial
<220> FEATURE:
<223> OTHER INFORMATION: Synthetic construct

<400> SEQUENCE: 236
tttggattat acttctgaat aatggaaggg ttagaaccta ccttccaatc cattatctcc 60
acta 64

<210> SEQ ID NO 237
<211> LENGTH: 64
<212> TYPE: DNA
<213> ORGANISM: Artificial
<220> FEATURE:
<223> OTHER INFORMATION: Synthetic construct

<400> SEQUENCE: 237
atatcaaaat tatttgcacg taaaacagaa ataaagaaat tgttccaatc cattatctcc 60
acta 64

<210> SEQ ID NO 238
<211> LENGTH: 64
<212> TYPE: DNA
<213> ORGANISM: Artificial
<220> FEATURE:
<223> OTHER INFORMATION: Synthetic construct

<400> SEQUENCE: 238
cgtagatttt caggtttaac gtcagatgaa tatacagtaa cattccaatc cattatctcc 60
acta 64

<210> SEQ ID NO 239
<211> LENGTH: 64
<212> TYPE: DNA
<213> ORGANISM: Artificial
<220> FEATURE:
<223> OTHER INFORMATION: Synthetic construct

<400> SEQUENCE: 239
gtacctttta catcgggaga aacaataacg gattcgcctg atttccaatc cattatctcc 60
acta 64

<210> SEQ ID NO 240
<211> LENGTH: 64
<212> TYPE: DNA
<213> ORGANISM: Artificial
<220> FEATURE:
<223> OTHER INFORMATION: Synthetic construct

<400> SEQUENCE: 240
tgctttgaat accaagttac aaaatcgcgc agaggcgaat tattccaatc cattatctcc 60
acta 64

<210> SEQ ID NO 241

<211> LENGTH: 64
<212> TYPE: DNA
<213> ORGANISM: Artificial
<220> FEATURE:
<223> OTHER INFORMATION: Synthetic construct

<400> SEQUENCE: 241
ttcatttcaa ttacctgagc aaaagaagat gatgaaacaa acttccaatc cattatctcc 60
acta 64

<210> SEQ ID NO 242
<211> LENGTH: 64
<212> TYPE: DNA
<213> ORGANISM: Artificial
<220> FEATURE:
<223> OTHER INFORMATION: Synthetic construct

<400> SEQUENCE: 242
atcaagaaaa caaaattaat tacatttaac aatttcattt gattccaatc cattatctcc 60
acta 64

<210> SEQ ID NO 243
<211> LENGTH: 64
<212> TYPE: DNA
<213> ORGANISM: Artificial
<220> FEATURE:
<223> OTHER INFORMATION: Synthetic construct

<400> SEQUENCE: 243
attacctttt ttaatggaaa cagtacataa atcaatatat gtttccaatc cattatctcc 60
acta 64

<210> SEQ ID NO 244
<211> LENGTH: 64
<212> TYPE: DNA
<213> ORGANISM: Artificial
<220> FEATURE:
<223> OTHER INFORMATION: Synthetic construct

<400> SEQUENCE: 244
gagtgaataa ccttgcttct gtaaatcgtc gctattaatt aattccaatc cattatctcc 60
acta 64

<210> SEQ ID NO 245
<211> LENGTH: 64
<212> TYPE: DNA
<213> ORGANISM: Artificial
<220> FEATURE:
<223> OTHER INFORMATION: Synthetic construct

<400> SEQUENCE: 245
ttttccctta gaatccttga aaacatagcg atagcttaga ttttccaatc cattatctcc 60
acta 64

<210> SEQ ID NO 246
<211> LENGTH: 64
<212> TYPE: DNA
<213> ORGANISM: Artificial
<220> FEATURE:
<223> OTHER INFORMATION: Synthetic construct

<400> SEQUENCE: 246
aagacgctga gaagagtcaa tagtgaattt atcaaaatca tattccaatc cattatctcc 60
acta 64

<210> SEQ ID NO 247
<211> LENGTH: 64
<212> TYPE: DNA
<213> ORGANISM: Artificial
<220> FEATURE:
<223> OTHER INFORMATION: Synthetic construct

<400> SEQUENCE: 247
ggtctgagag actacctttt taacctccgg cttaggttgg gtttccaatc cattatctcc 60
acta 64

<210> SEQ ID NO 248
<211> LENGTH: 64
<212> TYPE: DNA
<213> ORGANISM: Artificial
<220> FEATURE:
<223> OTHER INFORMATION: Synthetic construct

<400> SEQUENCE: 248
tatataacta tatgtaaatg ctgatgcaaa tccaatcgca agttccaatc cattatctcc 60
acta 64

<210> SEQ ID NO 249
<211> LENGTH: 64
<212> TYPE: DNA
<213> ORGANISM: Artificial
<220> FEATURE:
<223> OTHER INFORMATION: Synthetic construct

<400> SEQUENCE: 249
acaaagaacg cgagaaaact ttttcaaata tattttagtt aattccaatc cattatctcc 60
acta 64

<210> SEQ ID NO 250
<211> LENGTH: 64
<212> TYPE: DNA
<213> ORGANISM: Artificial
<220> FEATURE:
<223> OTHER INFORMATION: Synthetic construct

<400> SEQUENCE: 250
tttcatcttc tgacctaaat ttaatggttt gaaataccga ccttccaatc cattatctcc 60
acta 64

<210> SEQ ID NO 251
<211> LENGTH: 64
<212> TYPE: DNA
<213> ORGANISM: Artificial
<220> FEATURE:
<223> OTHER INFORMATION: Synthetic construct

<400> SEQUENCE: 251
gtgtgataaa taaggcgtta aataagaata aacaccggaa tcttccaatc cattatctcc 60
acta 64

<210> SEQ ID NO 252

<211> LENGTH: 64
<212> TYPE: DNA
<213> ORGANISM: Artificial
<220> FEATURE:
<223> OTHER INFORMATION: Synthetic construct

<400> SEQUENCE: 252
ataattacta gaaaaagcct gtttagtatc atatgcgtta tattccaatc cattatctcc 60
acta 64

<210> SEQ ID NO 253
<211> LENGTH: 64
<212> TYPE: DNA
<213> ORGANISM: Artificial
<220> FEATURE:
<223> OTHER INFORMATION: Synthetic construct

<400> SEQUENCE: 253
caaattctta ccagtataaa gccaacgctc aacagtaggg ctttccaatc cattatctcc 60
acta 64

<210> SEQ ID NO 254
<211> LENGTH: 64
<212> TYPE: DNA
<213> ORGANISM: Artificial
<220> FEATURE:
<223> OTHER INFORMATION: Synthetic construct

<400> SEQUENCE: 254
taattgagaa tcgccatatt taacaacgcc aacatgtaat ttttccaatc cattatctcc 60
acta 64

<210> SEQ ID NO 255
<211> LENGTH: 64
<212> TYPE: DNA
<213> ORGANISM: Artificial
<220> FEATURE:
<223> OTHER INFORMATION: Synthetic construct

<400> SEQUENCE: 255
aggcagaggc attttcgagc cagtaataag agaatataaa gtttccaatc cattatctcc 60
acta 64

<210> SEQ ID NO 256
<211> LENGTH: 64
<212> TYPE: DNA
<213> ORGANISM: Artificial
<220> FEATURE:
<223> OTHER INFORMATION: Synthetic construct

<400> SEQUENCE: 256
accgacaaaa ggtaaagtaa ttctgtccag acgacgacaa tattccaatc cattatctcc 60
acta 64

<210> SEQ ID NO 257
<211> LENGTH: 64
<212> TYPE: DNA
<213> ORGANISM: Artificial
<220> FEATURE:
<223> OTHER INFORMATION: Synthetic construct

<400> SEQUENCE: 257
aacaacatgt tcagctaatg cagaacgcgc ctgtttatca acttccaatc cattatctcc 60
acta 64

<210> SEQ ID NO 258
<211> LENGTH: 64
<212> TYPE: DNA
<213> ORGANISM: Artificial
<220> FEATURE:
<223> OTHER INFORMATION: Synthetic construct

<400> SEQUENCE: 258
aatagataag tcctgaacaa gaaaaataat atcccatcct aattccaatc cattatctcc 60
acta 64

<210> SEQ ID NO 259
<211> LENGTH: 64
<212> TYPE: DNA
<213> ORGANISM: Artificial
<220> FEATURE:
<223> OTHER INFORMATION: Synthetic construct

<400> SEQUENCE: 259
tttacgagca tgtagaaacc aatcaataat cggctgtctt tcttccaatc cattatctcc 60
acta 64

<210> SEQ ID NO 260
<211> LENGTH: 64
<212> TYPE: DNA
<213> ORGANISM: Artificial
<220> FEATURE:
<223> OTHER INFORMATION: Synthetic construct

<400> SEQUENCE: 260
cttatcattc caagaacggg tattaaacca agtaccgcac tcttccaatc cattatctcc 60
acta 64

<210> SEQ ID NO 261
<211> LENGTH: 64
<212> TYPE: DNA
<213> ORGANISM: Artificial
<220> FEATURE:
<223> OTHER INFORMATION: Synthetic construct

<400> SEQUENCE: 261
atcgagaaca agcaagccgt ttttattttc atcgtaggaa tcttccaatc cattatctcc 60
acta 64

<210> SEQ ID NO 262
<211> LENGTH: 64
<212> TYPE: DNA
<213> ORGANISM: Artificial
<220> FEATURE:
<223> OTHER INFORMATION: Synthetic construct

<400> SEQUENCE: 262
attaccgcgc ccaatagcaa gcaaatcaga tatagaaggc ttttccaatc cattatctcc 60
acta 64

<210> SEQ ID NO 263

<211> LENGTH: 64
<212> TYPE: DNA
<213> ORGANISM: Artificial
<220> FEATURE:
<223> OTHER INFORMATION: Synthetic construct

<400> SEQUENCE: 263
atccggtatt ctaagaacgc gaggcgtttt agcgaacctc ccttccaatc cattatctcc 60
acta 64

<210> SEQ ID NO 264
<211> LENGTH: 64
<212> TYPE: DNA
<213> ORGANISM: Artificial
<220> FEATURE:
<223> OTHER INFORMATION: Synthetic construct

<400> SEQUENCE: 264
gacttgcggg aggttttgaa gccttaaatc aagattagtt gcttccaatc cattatctcc 60
acta 64

<210> SEQ ID NO 265
<211> LENGTH: 64
<212> TYPE: DNA
<213> ORGANISM: Artificial
<220> FEATURE:
<223> OTHER INFORMATION: Synthetic construct

<400> SEQUENCE: 265
tattttgcac ccagctacaa ttttatcctg aatcttacca acttccaatc cattatctcc 60
acta 64

<210> SEQ ID NO 266
<211> LENGTH: 64
<212> TYPE: DNA
<213> ORGANISM: Artificial
<220> FEATURE:
<223> OTHER INFORMATION: Synthetic construct

<400> SEQUENCE: 266
gctaacgagc gtctttccag agcctaattt gccagttaca aattccaatc cattatctcc 60
acta 64

<210> SEQ ID NO 267
<211> LENGTH: 64
<212> TYPE: DNA
<213> ORGANISM: Artificial
<220> FEATURE:
<223> OTHER INFORMATION: Synthetic construct

<400> SEQUENCE: 267
ataaacagcc atattattta tcccaatcca aataagaaac gattccaatc cattatctcc 60
acta 64

<210> SEQ ID NO 268
<211> LENGTH: 64
<212> TYPE: DNA
<213> ORGANISM: Artificial
<220> FEATURE:
<223> OTHER INFORMATION: Synthetic construct

<400> SEQUENCE: 268 tttttgttt aacgtcaaaa atgaaaatag cagcctttac agttccaatc cattatctcc 60
acta 64

<210> SEQ ID NO 269
<211> LENGTH: 64
<212> TYPE: DNA
<213> ORGANISM: Artificial
<220> FEATURE:
<223> OTHER INFORMATION: Synthetic construct

<400> SEQUENCE: 269
agagaataac ataaaaacag ggaagcgcat tagacgggag aattccaatc cattatctcc 60
acta 64

<210> SEQ ID NO 270
<211> LENGTH: 64
<212> TYPE: DNA
<213> ORGANISM: Artificial
<220> FEATURE:
<223> OTHER INFORMATION: Synthetic construct

<400> SEQUENCE: 270
ttaactgaac accctgaaca aagtcagagg gtaattgagc gcttccaatc cattatctcc 60
acta 64

<210> SEQ ID NO 271
<211> LENGTH: 64
<212> TYPE: DNA
<213> ORGANISM: Artificial
<220> FEATURE:
<223> OTHER INFORMATION: Synthetic construct

<400> SEQUENCE: 271
taatatcaga gagataaccc acaagaattg agttaagccc aattccaatc cattatctcc 60
acta 64

<210> SEQ ID NO 272
<211> LENGTH: 64
<212> TYPE: DNA
<213> ORGANISM: Artificial
<220> FEATURE:
<223> OTHER INFORMATION: Synthetic construct

<400> SEQUENCE: 272
taataagagc aagaaacaat gaaatagcaa tagctatctt acttccaatc cattatctcc 60
acta 64

<210> SEQ ID NO 273
<211> LENGTH: 64
<212> TYPE: DNA
<213> ORGANISM: Artificial
<220> FEATURE:
<223> OTHER INFORMATION: Synthetic construct

<400> SEQUENCE: 273
cgaagccctt tttaagaaaa gtaagcagat agccgaacaa agttccaatc cattatctcc 60
acta 64

<210> SEQ ID NO 274

<211> LENGTH: 64
<212> TYPE: DNA
<213> ORGANISM: Artificial
<220> FEATURE:
<223> OTHER INFORMATION: Synthetic construct

<400> SEQUENCE: 274
ttaccagaag gaaaccgagg aaacgcaata ataacggaat acttccaatc cattatctcc 60
acta 64

<210> SEQ ID NO 275
<211> LENGTH: 64
<212> TYPE: DNA
<213> ORGANISM: Artificial
<220> FEATURE:
<223> OTHER INFORMATION: Synthetic construct

<400> SEQUENCE: 275
ccaaaagaac tggcatgatt aagactcctt attacgcagt atttccaatc cattatctcc 60
acta 64

<210> SEQ ID NO 276
<211> LENGTH: 64
<212> TYPE: DNA
<213> ORGANISM: Artificial
<220> FEATURE:
<223> OTHER INFORMATION: Synthetic construct

<400> SEQUENCE: 276
gttagcaaac gtagaaaata catacataaa ggtggcaaca tattccaatc cattatctcc 60
acta 64

<210> SEQ ID NO 277
<211> LENGTH: 64
<212> TYPE: DNA
<213> ORGANISM: Artificial
<220> FEATURE:
<223> OTHER INFORMATION: Synthetic construct

<400> SEQUENCE: 277
taaaagaaac gcaaagacac cacggaataa gtttattttg tcttccaatc cattatctcc 60
acta 64

<210> SEQ ID NO 278
<211> LENGTH: 64
<212> TYPE: DNA
<213> ORGANISM: Artificial
<220> FEATURE:
<223> OTHER INFORMATION: Synthetic construct

<400> SEQUENCE: 278
acaatcaata gaaaattcat atggtttacc agcgccaaag acttccaatc cattatctcc 60
acta 64

<210> SEQ ID NO 279
<211> LENGTH: 64
<212> TYPE: DNA
<213> ORGANISM: Artificial
<220> FEATURE:
<223> OTHER INFORMATION: Synthetic construct

<400> SEQUENCE: 279
aaaagggcga cattcaaccg attgagggag ggaaggtaaa tattccaatc cattatctcc 60
acta 64

<210> SEQ ID NO 280
<211> LENGTH: 64
<212> TYPE: DNA
<213> ORGANISM: Artificial
<220> FEATURE:
<223> OTHER INFORMATION: Synthetic construct

<400> SEQUENCE: 280
ttgacggaaa ttattcatta aaggtgaatt atcaccgtca ccttccaatc cattatctcc 60
acta 64

<210> SEQ ID NO 281
<211> LENGTH: 64
<212> TYPE: DNA
<213> ORGANISM: Artificial
<220> FEATURE:
<223> OTHER INFORMATION: Synthetic construct

<400> SEQUENCE: 281
gacttgagcc atttgggaat tagagccagc aaaatcacca gtttccaatc cattatctcc 60
acta 64

<210> SEQ ID NO 282
<211> LENGTH: 64
<212> TYPE: DNA
<213> ORGANISM: Artificial
<220> FEATURE:
<223> OTHER INFORMATION: Synthetic construct

<400> SEQUENCE: 282
agcaccatta ccattagcaa ggccggaaac gtcaccaatg aattccaatc cattatctcc 60
acta 64

<210> SEQ ID NO 283
<211> LENGTH: 64
<212> TYPE: DNA
<213> ORGANISM: Artificial
<220> FEATURE:
<223> OTHER INFORMATION: Synthetic construct

<400> SEQUENCE: 283
accatcgata gcagcaccgt aatcagtagc gacagaatca agttccaatc cattatctcc 60
acta 64

<210> SEQ ID NO 284
<211> LENGTH: 64
<212> TYPE: DNA
<213> ORGANISM: Artificial
<220> FEATURE:
<223> OTHER INFORMATION: Synthetic construct

<400> SEQUENCE: 284
tttgccttta gcgtcagact gtagcgcgtt ttcatcggca ttttccaatc cattatctcc 60
acta 64

<210> SEQ ID NO 285

<211> LENGTH: 64
<212> TYPE: DNA
<213> ORGANISM: Artificial
<220> FEATURE:
<223> OTHER INFORMATION: Synthetic construct

<400> SEQUENCE: 285
ttcggtcata gccccccttat tagcgtttgc catcttttca tattccaatc cattatctcc 60
acta 64

<210> SEQ ID NO 286
<211> LENGTH: 64
<212> TYPE: DNA
<213> ORGANISM: Artificial
<220> FEATURE:
<223> OTHER INFORMATION: Synthetic construct

<400> SEQUENCE: 286
atcaaaatca ccggaaccag agccaccacc ggaaccgcct ccttccaatc cattatctcc 60
acta 64

<210> SEQ ID NO 287
<211> LENGTH: 64
<212> TYPE: DNA
<213> ORGANISM: Artificial
<220> FEATURE:
<223> OTHER INFORMATION: Synthetic construct

<400> SEQUENCE: 287
ctcagagccg ccaccctcag aaccgccacc ctcagagcca ccttccaatc cattatctcc 60
acta 64

<210> SEQ ID NO 288
<211> LENGTH: 64
<212> TYPE: DNA
<213> ORGANISM: Artificial
<220> FEATURE:
<223> OTHER INFORMATION: Synthetic construct

<400> SEQUENCE: 288
accctcagag ccgccaccag aaccaccacc agagccgccg ccttccaatc cattatctcc 60
acta 64

<210> SEQ ID NO 289
<211> LENGTH: 64
<212> TYPE: DNA
<213> ORGANISM: Artificial
<220> FEATURE:
<223> OTHER INFORMATION: Synthetic construct

<400> SEQUENCE: 289
agcattgaca ggaggttgag gcaggtcaga cgattggcct tgttccaatc cattatctcc 60
acta 64

<210> SEQ ID NO 290
<211> LENGTH: 64
<212> TYPE: DNA
<213> ORGANISM: Artificial
<220> FEATURE:
<223> OTHER INFORMATION: Synthetic construct

<400> SEQUENCE: 290
atattcacaa acaaataaat cctcattaaa gccagaatgg aattccaatc cattatctcc 60
acta 64

<210> SEQ ID NO 291
<211> LENGTH: 64
<212> TYPE: DNA
<213> ORGANISM: Artificial
<220> FEATURE:
<223> OTHER INFORMATION: Synthetic construct

<400> SEQUENCE: 291
agcgcagtct ctgaatttac cgttccagta agcgtcatac atttccaatc cattatctcc 60
acta 64

<210> SEQ ID NO 292
<211> LENGTH: 64
<212> TYPE: DNA
<213> ORGANISM: Artificial
<220> FEATURE:
<223> OTHER INFORMATION: Synthetic construct

<400> SEQUENCE: 292
ggcttttgat gatacaggag tgtactggta ataagtttta acttccaatc cattatctcc 60
acta 64

<210> SEQ ID NO 293
<211> LENGTH: 64
<212> TYPE: DNA
<213> ORGANISM: Artificial
<220> FEATURE:
<223> OTHER INFORMATION: Synthetic construct

<400> SEQUENCE: 293
ggggtcagtg ccttgagtaa cagtgcccgt ataaacagtt aattccaatc cattatctcc 60
acta 64

<210> SEQ ID NO 294
<211> LENGTH: 64
<212> TYPE: DNA
<213> ORGANISM: Artificial
<220> FEATURE:
<223> OTHER INFORMATION: Synthetic construct

<400> SEQUENCE: 294
tgccccctgc ctatttcgga acctattatt ctgaaacatg aattccaatc cattatctcc 60
acta 64

<210> SEQ ID NO 295
<211> LENGTH: 64
<212> TYPE: DNA
<213> ORGANISM: Artificial
<220> FEATURE:
<223> OTHER INFORMATION: Synthetic construct

<400> SEQUENCE: 295
agtattaaga ggctgagact cctcaagaga aggattagga ttttccaatc cattatctcc 60
acta 64

<210> SEQ ID NO 296

<211> LENGTH: 64
<212> TYPE: DNA
<213> ORGANISM: Artificial
<220> FEATURE:
<223> OTHER INFORMATION: Synthetic construct

<400> SEQUENCE: 296
agcggggttt tgctcagtac caggcggata agtgccgtcg agttccaatc cattatctcc 60
acta 64

<210> SEQ ID NO 297
<211> LENGTH: 64
<212> TYPE: DNA
<213> ORGANISM: Artificial
<220> FEATURE:
<223> OTHER INFORMATION: Synthetic construct

<400> SEQUENCE: 297
agggttgata taagtatagc ccggaatagg tgtatcaccg tattccaatc cattatctcc 60
acta 64

<210> SEQ ID NO 298
<211> LENGTH: 64
<212> TYPE: DNA
<213> ORGANISM: Artificial
<220> FEATURE:
<223> OTHER INFORMATION: Synthetic construct

<400> SEQUENCE: 298
ctcaggaggt ttagtaccgc caccctcaga accgccaccc tcttccaatc cattatctcc 60
acta 64

<210> SEQ ID NO 299
<211> LENGTH: 64
<212> TYPE: DNA
<213> ORGANISM: Artificial
<220> FEATURE:
<223> OTHER INFORMATION: Synthetic construct

<400> SEQUENCE: 299
agaaccgcca ccctcagagc caccaccctc attttcaggg atttccaatc cattatctcc 60
acta 64

<210> SEQ ID NO 300
<211> LENGTH: 64
<212> TYPE: DNA
<213> ORGANISM: Artificial
<220> FEATURE:
<223> OTHER INFORMATION: Synthetic construct

<400> SEQUENCE: 300
agcaagccca ataggaaccc atgtaccgta acactgagtt tcttccaatc cattatctcc 60
acta 64

<210> SEQ ID NO 301
<211> LENGTH: 64
<212> TYPE: DNA
<213> ORGANISM: Artificial
<220> FEATURE:
<223> OTHER INFORMATION: Synthetic construct

<400> SEQUENCE: 301
gtcaccagta caaactacaa cgcctgtagc attccacaga cattccaatc cattatctcc 60
acta 64

<210> SEQ ID NO 302
<211> LENGTH: 64
<212> TYPE: DNA
<213> ORGANISM: Artificial
<220> FEATURE:
<223> OTHER INFORMATION: Synthetic construct

<400> SEQUENCE: 302
gccctcatag ttagcgtaac gatctaaagt tttgtcgtct ttttccaatc cattatctcc 60
acta 64

<210> SEQ ID NO 303
<211> LENGTH: 64
<212> TYPE: DNA
<213> ORGANISM: Artificial
<220> FEATURE:
<223> OTHER INFORMATION: Synthetic construct

<400> SEQUENCE: 303
ccagacgtta gtaaatgaat tttctgtatg ggattttgct aattccaatc cattatctcc 60
acta 64

<210> SEQ ID NO 304
<211> LENGTH: 64
<212> TYPE: DNA
<213> ORGANISM: Artificial
<220> FEATURE:
<223> OTHER INFORMATION: Synthetic construct

<400> SEQUENCE: 304
acaactttca acagtttcag cggagtgaga atagaaagga acttccaatc cattatctcc 60
acta 64

<210> SEQ ID NO 305
<211> LENGTH: 64
<212> TYPE: DNA
<213> ORGANISM: Artificial
<220> FEATURE:
<223> OTHER INFORMATION: Synthetic construct

<400> SEQUENCE: 305
aactaaagga attgcgaata ataatttttt cacgttgaaa atttccaatc cattatctcc 60
acta 64

<210> SEQ ID NO 306
<211> LENGTH: 64
<212> TYPE: DNA
<213> ORGANISM: Artificial
<220> FEATURE:
<223> OTHER INFORMATION: Synthetic construct

<400> SEQUENCE: 306
ctccaaaaaa aaggctccaa aaggagcctt taattgtatc ggttccaatc cattatctcc 60
acta 64

<210> SEQ ID NO 307

<211> LENGTH: 64
<212> TYPE: DNA
<213> ORGANISM: Artificial
<220> FEATURE:
<223> OTHER INFORMATION: Synthetic construct

<400> SEQUENCE: 307
tttatcagct tgctttcgag gtgaatttct taaacagctt gattccaatc cattatctcc 60
acta 64

<210> SEQ ID NO 308
<211> LENGTH: 64
<212> TYPE: DNA
<213> ORGANISM: Artificial
<220> FEATURE:
<223> OTHER INFORMATION: Synthetic construct

<400> SEQUENCE: 308
taccgatagt tgcgccgaca atgacaacaa ccatcgccca cgttccaatc cattatctcc 60
acta 64

<210> SEQ ID NO 309
<211> LENGTH: 64
<212> TYPE: DNA
<213> ORGANISM: Artificial
<220> FEATURE:
<223> OTHER INFORMATION: Synthetic construct

<400> SEQUENCE: 309
cataaccgat atattcggtc gctgaggctt gcagggagtt aattccaatc cattatctcc 60
acta 64

<210> SEQ ID NO 310
<211> LENGTH: 64
<212> TYPE: DNA
<213> ORGANISM: Artificial
<220> FEATURE:
<223> OTHER INFORMATION: Synthetic construct

<400> SEQUENCE: 310
aggccgcttt tgcgggatcg tcaccctcag cagcgaaaga cattccaatc cattatctcc 60
acta 64

<210> SEQ ID NO 311
<211> LENGTH: 64
<212> TYPE: DNA
<213> ORGANISM: Artificial
<220> FEATURE:
<223> OTHER INFORMATION: Synthetic construct

<400> SEQUENCE: 311
gcatcggaac gagggtagca acggctacag aggctttgag gattccaatc cattatctcc 60
acta 64

<210> SEQ ID NO 312
<211> LENGTH: 64
<212> TYPE: DNA
<213> ORGANISM: Artificial
<220> FEATURE:
<223> OTHER INFORMATION: Synthetic construct

<400> SEQUENCE: 312
ctaaagactt tttcatgagg aagtttccat taaacgggta aattccaatc cattatctcc 60
acta 64

<210> SEQ ID NO 313
<211> LENGTH: 64
<212> TYPE: DNA
<213> ORGANISM: Artificial
<220> FEATURE:
<223> OTHER INFORMATION: Synthetic construct

<400> SEQUENCE: 313
atacgtaatg ccactacgaa ggcaccaacc taaaacgaaa gattccaatc cattatctcc 60
acta 64

<210> SEQ ID NO 314
<211> LENGTH: 64
<212> TYPE: DNA
<213> ORGANISM: Artificial
<220> FEATURE:
<223> OTHER INFORMATION: Synthetic construct

<400> SEQUENCE: 314
ggcaaaagaa tacactaaaa cactcatctt tgaccccag cgttccaatc cattatctcc 60
acta 64

<210> SEQ ID NO 315
<211> LENGTH: 64
<212> TYPE: DNA
<213> ORGANISM: Artificial
<220> FEATURE:
<223> OTHER INFORMATION: Synthetic construct

<400> SEQUENCE: 315
attataccaa gcgcgaaaca aagtacaacg gagatttgta tcttccaatc cattatctcc 60
acta 64

<210> SEQ ID NO 316
<211> LENGTH: 64
<212> TYPE: DNA
<213> ORGANISM: Artificial
<220> FEATURE:
<223> OTHER INFORMATION: Synthetic construct

<400> SEQUENCE: 316
atcgcctgat aaattgtgtc gaaatccgcg acctgctcca tgttccaatc cattatctcc 60
acta 64

<210> SEQ ID NO 317
<211> LENGTH: 64
<212> TYPE: DNA
<213> ORGANISM: Artificial
<220> FEATURE:
<223> OTHER INFORMATION: Synthetic construct

<400> SEQUENCE: 317
ttacttagcc ggaacgaggc gcagacggtc aatcataagg gattccaatc cattatctcc 60
acta 64

<210> SEQ ID NO 318

<211> LENGTH: 64
<212> TYPE: DNA
<213> ORGANISM: Artificial
<220> FEATURE:
<223> OTHER INFORMATION: Synthetic construct

<400> SEQUENCE: 318
accgaactga ccaactttga aagaggacag atgaacggtg tattccaatc cattatctcc 60
acta 64

<210> SEQ ID NO 319
<211> LENGTH: 64
<212> TYPE: DNA
<213> ORGANISM: Artificial
<220> FEATURE:
<223> OTHER INFORMATION: Synthetic construct

<400> SEQUENCE: 319
cagaccaggc gcataggctg gctgaccttc atcaagagta atttccaatc cattatctcc 60
acta 64

<210> SEQ ID NO 320
<211> LENGTH: 64
<212> TYPE: DNA
<213> ORGANISM: Artificial
<220> FEATURE:
<223> OTHER INFORMATION: Synthetic construct

<400> SEQUENCE: 320
cttgacaaga accggatatt cattacccaa atcaacgtaa cattccaatc cattatctcc 60
acta 64

<210> SEQ ID NO 321
<211> LENGTH: 64
<212> TYPE: DNA
<213> ORGANISM: Artificial
<220> FEATURE:
<223> OTHER INFORMATION: Synthetic construct

<400> SEQUENCE: 321
aagctgctca ttcagtgaat aaggcttgcc ctgacgagaa acttccaatc cattatctcc 60
acta 64

<210> SEQ ID NO 322
<211> LENGTH: 64
<212> TYPE: DNA
<213> ORGANISM: Artificial
<220> FEATURE:
<223> OTHER INFORMATION: Synthetic construct

<400> SEQUENCE: 322
accagaacga gtagtaaatt gggcttgaga tggtttaatt tcttccaatc cattatctcc 60
acta 64

<210> SEQ ID NO 323
<211> LENGTH: 64
<212> TYPE: DNA
<213> ORGANISM: Artificial
<220> FEATURE:
<223> OTHER INFORMATION: Synthetic construct

<400> SEQUENCE: 323
aactttaatc attgtgaatt accttatgcg attttaagaa ctttccaatc cattatctcc 60
acta 64

<210> SEQ ID NO 324
<211> LENGTH: 64
<212> TYPE: DNA
<213> ORGANISM: Artificial
<220> FEATURE:
<223> OTHER INFORMATION: Synthetic construct

<400> SEQUENCE: 324
ggctcattat accagtcagg acgttgggaa gaaaaatcta cgttccaatc cattatctcc 60
acta 64

<210> SEQ ID NO 325
<211> LENGTH: 64
<212> TYPE: DNA
<213> ORGANISM: Artificial
<220> FEATURE:
<223> OTHER INFORMATION: Synthetic construct

<400> SEQUENCE: 325
ttaataaaac gaactaacgg aacaacatta ttacaggtag aattccaatc cattatctcc 60
acta 64

<210> SEQ ID NO 326
<211> LENGTH: 64
<212> TYPE: DNA
<213> ORGANISM: Artificial
<220> FEATURE:
<223> OTHER INFORMATION: Synthetic construct

<400> SEQUENCE: 326
agattcatca gttgagattt aggaatacca cattcaacta atttccaatc cattatctcc 60
acta 64

<210> SEQ ID NO 327
<211> LENGTH: 64
<212> TYPE: DNA
<213> ORGANISM: Artificial
<220> FEATURE:
<223> OTHER INFORMATION: Synthetic construct

<400> SEQUENCE: 327
gcagatacat aacgccaaaa ggaattacga ggcatagtaa gattccaatc cattatctcc 60
acta 64

<210> SEQ ID NO 328
<211> LENGTH: 64
<212> TYPE: DNA
<213> ORGANISM: Artificial
<220> FEATURE:
<223> OTHER INFORMATION: Synthetic construct

<400> SEQUENCE: 328
gcaacactat cataaccctc gtttaccaga cgacgataaa aattccaatc cattatctcc 60
acta 64

<210> SEQ ID NO 329

<211> LENGTH: 64
<212> TYPE: DNA
<213> ORGANISM: Artificial
<220> FEATURE:
<223> OTHER INFORMATION: Synthetic construct

<400> SEQUENCE: 329
ccaaaatagc gagaggcttt tgcaaaagaa gttttgccag agttccaatc cattatctcc 60
acta 64

<210> SEQ ID NO 330
<211> LENGTH: 64
<212> TYPE: DNA
<213> ORGANISM: Artificial
<220> FEATURE:
<223> OTHER INFORMATION: Synthetic construct

<400> SEQUENCE: 330
ggggtaatag taaaatgttt agactggata gcgtccaata ctttccaatc cattatctcc 60
acta 64

<210> SEQ ID NO 331
<211> LENGTH: 64
<212> TYPE: DNA
<213> ORGANISM: Artificial
<220> FEATURE:
<223> OTHER INFORMATION: Synthetic construct

<400> SEQUENCE: 331
gcggaatcgt cataaatatt cattgaatcc ccctcaaatg ctttccaatc cattatctcc 60
acta 64

<210> SEQ ID NO 332
<211> LENGTH: 64
<212> TYPE: DNA
<213> ORGANISM: Artificial
<220> FEATURE:
<223> OTHER INFORMATION: Synthetic construct

<400> SEQUENCE: 332
ttaaacagtt cagaaaacga gaatgaccat aaatcaaaaa tcttccaatc cattatctcc 60
acta 64

<210> SEQ ID NO 333
<211> LENGTH: 64
<212> TYPE: DNA
<213> ORGANISM: Artificial
<220> FEATURE:
<223> OTHER INFORMATION: Synthetic construct

<400> SEQUENCE: 333
aggtctttac cctgactatt atagtcagaa gcaaagcgga ttttccaatc cattatctcc 60
acta 64

<210> SEQ ID NO 334
<211> LENGTH: 64
<212> TYPE: DNA
<213> ORGANISM: Artificial
<220> FEATURE:
<223> OTHER INFORMATION: Synthetic construct

<400> SEQUENCE: 334
gcatcaaaaa gattaagagg aagcccgaaa gacttcaaat atttccaatc cattatctcc 60
acta 64

<210> SEQ ID NO 335
<211> LENGTH: 64
<212> TYPE: DNA
<213> ORGANISM: Artificial
<220> FEATURE:
<223> OTHER INFORMATION: Synthetic construct

<400> SEQUENCE: 335
cgcgttttaa ttcgagcttc aaagcgaacc agaccggaag cattccaatc cattatctcc 60
acta 64

<210> SEQ ID NO 336
<211> LENGTH: 64
<212> TYPE: DNA
<213> ORGANISM: Artificial
<220> FEATURE:
<223> OTHER INFORMATION: Synthetic construct

<400> SEQUENCE: 336
aactccaaca ggtcaggatt agagagtacc tttaattgct ccttccaatc cattatctcc 60
acta 64

<210> SEQ ID NO 337
<211> LENGTH: 64
<212> TYPE: DNA
<213> ORGANISM: Artificial
<220> FEATURE:
<223> OTHER INFORMATION: Synthetic construct

<400> SEQUENCE: 337
ttttgataag aggtcatttt tgcggatggc ttagagctta atttccaatc cattatctcc 60
acta 64

<210> SEQ ID NO 338
<211> LENGTH: 64
<212> TYPE: DNA
<213> ORGANISM: Artificial
<220> FEATURE:
<223> OTHER INFORMATION: Synthetic construct

<400> SEQUENCE: 338
tgctgaatat aatgctgtag ctcaacatgt tttaaatatg cattccaatc cattatctcc 60
acta 64

<210> SEQ ID NO 339
<211> LENGTH: 64
<212> TYPE: DNA
<213> ORGANISM: Artificial
<220> FEATURE:
<223> OTHER INFORMATION: Synthetic construct

<400> SEQUENCE: 339
actaaagtac ggtgtctgga agtttcattc catataacag ttttccaatc cattatctcc 60
acta 64

<210> SEQ ID NO 340

<211> LENGTH: 64
<212> TYPE: DNA
<213> ORGANISM: Artificial
<220> FEATURE:
<223> OTHER INFORMATION: Synthetic construct

<400> SEQUENCE: 340
gattcccaat tctgcgaacg agtagattta gtttgaccat tattccaatc cattatctcc 60
acta 64

<210> SEQ ID NO 341
<211> LENGTH: 64
<212> TYPE: DNA
<213> ORGANISM: Artificial
<220> FEATURE:
<223> OTHER INFORMATION: Synthetic construct

<400> SEQUENCE: 341
gatacatttc gcaaatggtc aataacctgt ttagctatat ttttccaatc cattatctcc 60
acta 64

<210> SEQ ID NO 342
<211> LENGTH: 64
<212> TYPE: DNA
<213> ORGANISM: Artificial
<220> FEATURE:
<223> OTHER INFORMATION: Synthetic construct

<400> SEQUENCE: 342
tcatttgggg cgcgagctga aaaggtggca tcaattctac tattccaatc cattatctcc 60
acta 64

<210> SEQ ID NO 343
<211> LENGTH: 64
<212> TYPE: DNA
<213> ORGANISM: Artificial
<220> FEATURE:
<223> OTHER INFORMATION: Synthetic construct

<400> SEQUENCE: 343
atagtagtag cattaacatc caataaatca tacaggcaag gcttccaatc cattatctcc 60
acta 64

<210> SEQ ID NO 344
<211> LENGTH: 64
<212> TYPE: DNA
<213> ORGANISM: Artificial
<220> FEATURE:
<223> OTHER INFORMATION: Synthetic construct

<400> SEQUENCE: 344
aaagaattag caaaattaag caataaagcc tcagagcata aattccaatc cattatctcc 60
acta 64

<210> SEQ ID NO 345
<211> LENGTH: 64
<212> TYPE: DNA
<213> ORGANISM: Artificial
<220> FEATURE:
<223> OTHER INFORMATION: Synthetic construct

<400> SEQUENCE: 345
gctaaatcgg ttgtaccaaa aacattatga ccctgtaata ctttccaatc cattatctcc 60
acta 64

<210> SEQ ID NO 346
<211> LENGTH: 64
<212> TYPE: DNA
<213> ORGANISM: Artificial
<220> FEATURE:
<223> OTHER INFORMATION: Synthetic construct

<400> SEQUENCE: 346
tttgcgggag aagcctttat ttcaacgcaa ggataaaaat ttttccaatc cattatctcc 60
acta 64

<210> SEQ ID NO 347
<211> LENGTH: 64
<212> TYPE: DNA
<213> ORGANISM: Artificial
<220> FEATURE:
<223> OTHER INFORMATION: Synthetic construct

<400> SEQUENCE: 347
ttagaaccct catatatttt aaatgcaatg cctgagtaat gtttccaatc cattatctcc 60
acta 64

<210> SEQ ID NO 348
<211> LENGTH: 64
<212> TYPE: DNA
<213> ORGANISM: Artificial
<220> FEATURE:
<223> OTHER INFORMATION: Synthetic construct

<400> SEQUENCE: 348
gtaggtaaag attcaaaagg gtgagaaagg ccggagacag tcttccaatc cattatctcc 60
acta 64

<210> SEQ ID NO 349
<211> LENGTH: 64
<212> TYPE: DNA
<213> ORGANISM: Artificial
<220> FEATURE:
<223> OTHER INFORMATION: Synthetic construct

<400> SEQUENCE: 349
aaatcaccat caatatgata ttcaaccgtt ctagctgata aattccaatc cattatctcc 60
acta 64

<210> SEQ ID NO 350
<211> LENGTH: 64
<212> TYPE: DNA
<213> ORGANISM: Artificial
<220> FEATURE:
<223> OTHER INFORMATION: Synthetic construct

<400> SEQUENCE: 350
ttaatgccgg agagggtagc tatttttgag agatctacaa agttccaatc cattatctcc 60
acta 64

<210> SEQ ID NO 351

<211> LENGTH: 64
<212> TYPE: DNA
<213> ORGANISM: Artificial
<220> FEATURE:
<223> OTHER INFORMATION: Synthetic construct

<400> SEQUENCE: 351
gctatcaggt cattgcctga gagtctggag caaacaagag aattccaatc cattatctcc 60
acta 64

<210> SEQ ID NO 352
<211> LENGTH: 64
<212> TYPE: DNA
<213> ORGANISM: Artificial
<220> FEATURE:
<223> OTHER INFORMATION: Synthetic construct

<400> SEQUENCE: 352
tcgatgaacg gtaatcgtaa aactagcatg tcaatcatat gtttccaatc cattatctcc 60
acta 64

<210> SEQ ID NO 353
<211> LENGTH: 64
<212> TYPE: DNA
<213> ORGANISM: Artificial
<220> FEATURE:
<223> OTHER INFORMATION: Synthetic construct

<400> SEQUENCE: 353
accccggttg ataatcagaa aagccccaaa aacaggaaga ttttccaatc cattatctcc 60
acta 64

<210> SEQ ID NO 354
<211> LENGTH: 64
<212> TYPE: DNA
<213> ORGANISM: Artificial
<220> FEATURE:
<223> OTHER INFORMATION: Synthetic construct

<400> SEQUENCE: 354
gtataagcaa atatttaaat tgtaaacgtt aatattttgt tattccaatc cattatctcc 60
acta 64

<210> SEQ ID NO 355
<211> LENGTH: 64
<212> TYPE: DNA
<213> ORGANISM: Artificial
<220> FEATURE:
<223> OTHER INFORMATION: Synthetic construct

<400> SEQUENCE: 355
aaattcgcat taaatttttg ttaaatcagc tcattttta acttccaatc cattatctcc 60
acta 64

<210> SEQ ID NO 356
<211> LENGTH: 64
<212> TYPE: DNA
<213> ORGANISM: Artificial
<220> FEATURE:
<223> OTHER INFORMATION: Synthetic construct

<400> SEQUENCE: 356
caataggaac gccatcaaaa ataattcgcg tctggccttc ctttccaatc cattatctcc 60
acta 64

<210> SEQ ID NO 357
<211> LENGTH: 64
<212> TYPE: DNA
<213> ORGANISM: Artificial
<220> FEATURE:
<223> OTHER INFORMATION: Synthetic construct

<400> SEQUENCE: 357
gtagccagct ttcatcaaca ttaaatgtga gcgagtaaca acttccaatc cattatctcc 60
acta 64

<210> SEQ ID NO 358
<211> LENGTH: 64
<212> TYPE: DNA
<213> ORGANISM: Artificial
<220> FEATURE:
<223> OTHER INFORMATION: Synthetic construct

<400> SEQUENCE: 358
ccgtcggatt ctccgtggga acaaacggcg gattgaccgt aattccaatc cattatctcc 60
acta 64

<210> SEQ ID NO 359
<211> LENGTH: 64
<212> TYPE: DNA
<213> ORGANISM: Artificial
<220> FEATURE:
<223> OTHER INFORMATION: Synthetic construct

<400> SEQUENCE: 359
tgggataggt cacgttggtg tagatgggcg catcgtaacc gtttccaatc cattatctcc 60
acta 64

<210> SEQ ID NO 360
<211> LENGTH: 64
<212> TYPE: DNA
<213> ORGANISM: Artificial
<220> FEATURE:
<223> OTHER INFORMATION: Synthetic construct

<400> SEQUENCE: 360
gcatctgcca gtttgagggg acgacgacag tatcggcctc agttccaatc cattatctcc 60
acta 64

<210> SEQ ID NO 361
<211> LENGTH: 64
<212> TYPE: DNA
<213> ORGANISM: Artificial
<220> FEATURE:
<223> OTHER INFORMATION: Synthetic construct

<400> SEQUENCE: 361
gaagatcgca ctccagccag ctttccggca ccgcttctgg tgttccaatc cattatctcc 60
acta 64

<210> SEQ ID NO 362

<211> LENGTH: 64
<212> TYPE: DNA
<213> ORGANISM: Artificial
<220> FEATURE:
<223> OTHER INFORMATION: Synthetic construct

<400> SEQUENCE: 362
ccggaaacca ggcaaagcgc cattcgccat tcaggctgcg cattccaatc cattatctcc 60
acta 64

<210> SEQ ID NO 363
<211> LENGTH: 64
<212> TYPE: DNA
<213> ORGANISM: Artificial
<220> FEATURE:
<223> OTHER INFORMATION: Synthetic construct

<400> SEQUENCE: 363
actgttggga agggcgatcg gtgcgggcct cttcgctatt acttccaatc cattatctcc 60
acta 64

<210> SEQ ID NO 364
<211> LENGTH: 64
<212> TYPE: DNA
<213> ORGANISM: Artificial
<220> FEATURE:
<223> OTHER INFORMATION: Synthetic construct

<400> SEQUENCE: 364
gccagctggc gaaaggggga tgtgctgcaa ggcgattaag ttttccaatc cattatctcc 60
acta 64

<210> SEQ ID NO 365
<211> LENGTH: 64
<212> TYPE: DNA
<213> ORGANISM: Artificial
<220> FEATURE:
<223> OTHER INFORMATION: Synthetic construct

<400> SEQUENCE: 365
gggtaacgcc agggttttcc cagtcacgac gttgtaaaac gattccaatc cattatctcc 60
acta 64

<210> SEQ ID NO 366
<211> LENGTH: 64
<212> TYPE: DNA
<213> ORGANISM: Artificial
<220> FEATURE:
<223> OTHER INFORMATION: Synthetic construct

<400> SEQUENCE: 366
cggccagtgc caagctttca gaggtggagc cgccacggga acttccaatc cattatctcc 60
acta 64

<210> SEQ ID NO 367
<211> LENGTH: 64
<212> TYPE: DNA
<213> ORGANISM: Artificial
<220> FEATURE:
<223> OTHER INFORMATION: Synthetic construct

<400> SEQUENCE: 367
ggataacctc accggaaaca atcggcgaaa cgtacagcgc cattccaatc cattatctcc 60
acta 64

<210> SEQ ID NO 368
<211> LENGTH: 64
<212> TYPE: DNA
<213> ORGANISM: Artificial
<220> FEATURE:
<223> OTHER INFORMATION: Synthetic construct

<400> SEQUENCE: 368
tgtttaccag tcccggaatt tgtgagagat agactttctc cgttccaatc cattatctcc 60
acta 64

<210> SEQ ID NO 369
<211> LENGTH: 64
<212> TYPE: DNA
<213> ORGANISM: Artificial
<220> FEATURE:
<223> OTHER INFORMATION: Synthetic construct

<400> SEQUENCE: 369
tggtgaaggg atagctctca cggaaaaaga gacgcagaaa cattccaatc cattatctcc 60
acta 64

<210> SEQ ID NO 370
<211> LENGTH: 64
<212> TYPE: DNA
<213> ORGANISM: Artificial
<220> FEATURE:
<223> OTHER INFORMATION: Synthetic construct

<400> SEQUENCE: 370
gcggatcaaa cttaaatttc tgctcatttg ccgccagcag ttttccaatc cattatctcc 60
acta 64

<210> SEQ ID NO 371
<211> LENGTH: 64
<212> TYPE: DNA
<213> ORGANISM: Artificial
<220> FEATURE:
<223> OTHER INFORMATION: Synthetic construct

<400> SEQUENCE: 371
gggcggttgt gtacatcgac ataaaaaaat cccgtaaaaa aattccaatc cattatctcc 60
acta 64

<210> SEQ ID NO 372
<211> LENGTH: 64
<212> TYPE: DNA
<213> ORGANISM: Artificial
<220> FEATURE:
<223> OTHER INFORMATION: Synthetic construct

<400> SEQUENCE: 372
gccgcacagg cggcctttag tgatgaaggg taaagttaaa cgttccaatc cattatctcc 60
acta 64

<210> SEQ ID NO 373

<211> LENGTH: 64
<212> TYPE: DNA
<213> ORGANISM: Artificial
<220> FEATURE:
<223> OTHER INFORMATION: Synthetic construct

<400> SEQUENCE: 373
atgctgattg ccgttccggc aaacgcggtc cgttttttcg tcttccaatc cattatctcc 60
acta 64

<210> SEQ ID NO 374
<211> LENGTH: 64
<212> TYPE: DNA
<213> ORGANISM: Artificial
<220> FEATURE:
<223> OTHER INFORMATION: Synthetic construct

<400> SEQUENCE: 374
tcgtcgctgg cagcctccgg ccagagcaca tcctcataac ggttccaatc cattatctcc 60
acta 64

<210> SEQ ID NO 375
<211> LENGTH: 64
<212> TYPE: DNA
<213> ORGANISM: Artificial
<220> FEATURE:
<223> OTHER INFORMATION: Synthetic construct

<400> SEQUENCE: 375
aacgtgccgg acttgtagaa cgtcagcgtg gtgctggtct ggttccaatc cattatctcc 60
acta 64

<210> SEQ ID NO 376
<211> LENGTH: 64
<212> TYPE: DNA
<213> ORGANISM: Artificial
<220> FEATURE:
<223> OTHER INFORMATION: Synthetic construct

<400> SEQUENCE: 376
tcagcagcaa ccgcaagaat gccaacggca gcaccgtcgg tgttccaatc cattatctcc 60
acta 64

<210> SEQ ID NO 377
<211> LENGTH: 64
<212> TYPE: DNA
<213> ORGANISM: Artificial
<220> FEATURE:
<223> OTHER INFORMATION: Synthetic construct

<400> SEQUENCE: 377
gtgccatccc acgcaaccag cttacggctg gaggtgtcca gcttccaatc cattatctcc 60
acta 64

<210> SEQ ID NO 378
<211> LENGTH: 64
<212> TYPE: DNA
<213> ORGANISM: Artificial
<220> FEATURE:
<223> OTHER INFORMATION: Synthetic construct

<400> SEQUENCE: 378
atcagcgggg tcattgcagg cgctttcgca ctcaatccgc cgttccaatc cattatctcc 60
acta 64

<210> SEQ ID NO 379
<211> LENGTH: 64
<212> TYPE: DNA
<213> ORGANISM: Artificial
<220> FEATURE:
<223> OTHER INFORMATION: Synthetic construct

<400> SEQUENCE: 379
ggcgcggttg cggtatgagc cgggtcactg ttgccctgcg gcttccaatc cattatctcc 60
acta 64

<210> SEQ ID NO 380
<211> LENGTH: 64
<212> TYPE: DNA
<213> ORGANISM: Artificial
<220> FEATURE:
<223> OTHER INFORMATION: Synthetic construct

<400> SEQUENCE: 380
tggtaatggg taaaggtttc tttgctcgtc ataaacatcc ctttccaatc cattatctcc 60
acta 64

<210> SEQ ID NO 381
<211> LENGTH: 64
<212> TYPE: DNA
<213> ORGANISM: Artificial
<220> FEATURE:
<223> OTHER INFORMATION: Synthetic construct

<400> SEQUENCE: 381
tacactggtg tgttcagcaa atcgttaacg gcatcagatg ccttccaatc cattatctcc 60
acta 64

<210> SEQ ID NO 382
<211> LENGTH: 64
<212> TYPE: DNA
<213> ORGANISM: Artificial
<220> FEATURE:
<223> OTHER INFORMATION: Synthetic construct

<400> SEQUENCE: 382
gggttacctg cagccagcgg tgccggtgcc ccctgcatca gattccaatc cattatctcc 60
acta 64

<210> SEQ ID NO 383
<211> LENGTH: 64
<212> TYPE: DNA
<213> ORGANISM: Artificial
<220> FEATURE:
<223> OTHER INFORMATION: Synthetic construct

<400> SEQUENCE: 383
cgatccagcg cagtgtcact gcgcgcctgt gcactctgtg gtttccaatc cattatctcc 60
acta 64

<210> SEQ ID NO 384

<211> LENGTH: 64
<212> TYPE: DNA
<213> ORGANISM: Artificial
<220> FEATURE:
<223> OTHER INFORMATION: Synthetic construct

<400> SEQUENCE: 384
gctgcggcca gaatgcggcg ggccgttttc acggtcatac cgttccaatc cattatctcc 60
acta 64

<210> SEQ ID NO 385
<211> LENGTH: 64
<212> TYPE: DNA
<213> ORGANISM: Artificial
<220> FEATURE:
<223> OTHER INFORMATION: Synthetic construct

<400> SEQUENCE: 385
ggggtttctg ccagcacgcg tgcctgttct tcgcgtccgt gattccaatc cattatctcc 60
acta 64

<210> SEQ ID NO 386
<211> LENGTH: 64
<212> TYPE: DNA
<213> ORGANISM: Artificial
<220> FEATURE:
<223> OTHER INFORMATION: Synthetic construct

<400> SEQUENCE: 386
gcctcctcac agttgaggat ccccgggtac cgagctcgaa ttttccaatc cattatctcc 60
acta 64

<210> SEQ ID NO 387
<211> LENGTH: 64
<212> TYPE: DNA
<213> ORGANISM: Artificial
<220> FEATURE:
<223> OTHER INFORMATION: Synthetic construct

<400> SEQUENCE: 387
cgtaatcatg gtcatagctg tttcctgtgt gaaattgtta tcttccaatc cattatctcc 60
acta 64

<210> SEQ ID NO 388
<211> LENGTH: 64
<212> TYPE: DNA
<213> ORGANISM: Artificial
<220> FEATURE:
<223> OTHER INFORMATION: Synthetic construct

<400> SEQUENCE: 388
cgctcacaat tccacacaac atacgagccg gaagcataaa gtttccaatc cattatctcc 60
acta 64

<210> SEQ ID NO 389
<211> LENGTH: 64
<212> TYPE: DNA
<213> ORGANISM: Artificial
<220> FEATURE:
<223> OTHER INFORMATION: Synthetic construct

<400> SEQUENCE: 389
gtaaagcctg gggtgcctaa tgagtgagct aactcacatt aattccaatc cattatctcc 60
acta 64

<210> SEQ ID NO 390
<211> LENGTH: 64
<212> TYPE: DNA
<213> ORGANISM: Artificial
<220> FEATURE:
<223> OTHER INFORMATION: Synthetic construct

<400> SEQUENCE: 390
ttgcgttgcg ctcactgccc gctttccagt cgggaaacct gtttccaatc cattatctcc 60
acta 64

<210> SEQ ID NO 391
<211> LENGTH: 64
<212> TYPE: DNA
<213> ORGANISM: Artificial
<220> FEATURE:
<223> OTHER INFORMATION: Synthetic construct

<400> SEQUENCE: 391
cgtgccagct gcattaatga atcggccaac gcgcggggag agttccaatc cattatctcc 60
acta 64

<210> SEQ ID NO 392
<211> LENGTH: 64
<212> TYPE: DNA
<213> ORGANISM: Artificial
<220> FEATURE:
<223> OTHER INFORMATION: Synthetic construct

<400> SEQUENCE: 392
gcggtttgcg tattgggcgc cagggtggtt tttcttttca ccttccaatc cattatctcc 60
acta 64

<210> SEQ ID NO 393
<211> LENGTH: 64
<212> TYPE: DNA
<213> ORGANISM: Artificial
<220> FEATURE:
<223> OTHER INFORMATION: Synthetic construct

<400> SEQUENCE: 393
agtgagacgg gcaacagctg attgcccttc accgcctggc ccttccaatc cattatctcc 60
acta 64

<210> SEQ ID NO 394
<211> LENGTH: 64
<212> TYPE: DNA
<213> ORGANISM: Artificial
<220> FEATURE:
<223> OTHER INFORMATION: Synthetic construct

<400> SEQUENCE: 394
tgagagagtt gcagcaagcg gtccacgctg gtttgcccca gcttccaatc cattatctcc 60
acta 64

<210> SEQ ID NO 395

<211> LENGTH: 64
<212> TYPE: DNA
<213> ORGANISM: Artificial
<220> FEATURE:
<223> OTHER INFORMATION: Synthetic construct

<400> SEQUENCE: 395
aggcgaaaat cctgtttgat ggtggttccg aaatcggcaa aattccaatc cattatctcc 60
acta 64

<210> SEQ ID NO 396
<211> LENGTH: 64
<212> TYPE: DNA
<213> ORGANISM: Artificial
<220> FEATURE:
<223> OTHER INFORMATION: Synthetic construct

<400> SEQUENCE: 396
tcccttataa atcaaaagaa tagcccgaga tagggttgag tgttccaatc cattatctcc 60
acta 64

<210> SEQ ID NO 397
<211> LENGTH: 64
<212> TYPE: DNA
<213> ORGANISM: Artificial
<220> FEATURE:
<223> OTHER INFORMATION: Synthetic construct

<400> SEQUENCE: 397
ttgttccagt ttggaacaag agtccactat taaagaacgt ggttccaatc cattatctcc 60
acta 64

<210> SEQ ID NO 398
<211> LENGTH: 64
<212> TYPE: DNA
<213> ORGANISM: Artificial
<220> FEATURE:
<223> OTHER INFORMATION: Synthetic construct

<400> SEQUENCE: 398
actccaacgt caaagggcga aaaaccgtct atcagggcga tgttccaatc cattatctcc 60
acta 64

<210> SEQ ID NO 399
<211> LENGTH: 64
<212> TYPE: DNA
<213> ORGANISM: Artificial
<220> FEATURE:
<223> OTHER INFORMATION: Synthetic construct

<400> SEQUENCE: 399
gcccactacg tgaaccatca cccaaatcaa gttttttggg gtttccaatc cattatctcc 60
acta 64

<210> SEQ ID NO 400
<211> LENGTH: 64
<212> TYPE: DNA
<213> ORGANISM: Artificial
<220> FEATURE:
<223> OTHER INFORMATION: Synthetic construct

<400> SEQUENCE: 400
cgaggtgccg taaagcacta aatcggaacc ctaaagggag ccttccaatc cattatctcc 60
acta 64

<210> SEQ ID NO 401
<211> LENGTH: 64
<212> TYPE: DNA
<213> ORGANISM: Artificial
<220> FEATURE:
<223> OTHER INFORMATION: Synthetic construct

<400> SEQUENCE: 401
cccgatttag agcttgacgg ggaaagccgg cgaacgtggc gattccaatc cattatctcc 60
acta 64

<210> SEQ ID NO 402
<211> LENGTH: 64
<212> TYPE: DNA
<213> ORGANISM: Artificial
<220> FEATURE:
<223> OTHER INFORMATION: Synthetic construct

<400> SEQUENCE: 402
gaaaggaagg gaagaaagcg aaaggagcgg gcgctagggc gcttccaatc cattatctcc 60
acta 64

<210> SEQ ID NO 403
<211> LENGTH: 64
<212> TYPE: DNA
<213> ORGANISM: Artificial
<220> FEATURE:
<223> OTHER INFORMATION: Synthetic construct

<400> SEQUENCE: 403
tggcaagtgt agcggtcacg ctgcgcgtaa ccaccacacc cgttccaatc cattatctcc 60
acta 64

<210> SEQ ID NO 404
<211> LENGTH: 44
<212> TYPE: DNA
<213> ORGANISM: Artificial
<220> FEATURE:
<223> OTHER INFORMATION: Synthetic construct

<400> SEQUENCE: 404
ccgcgcttaa tgcgccgcta cattccaatc cattatctcc acta 44

<210> SEQ ID NO 405
<211> LENGTH: 31
<212> TYPE: DNA
<213> ORGANISM: Artificial
<220> FEATURE:
<223> OTHER INFORMATION: Synthetic construct

<400> SEQUENCE: 405
gggcgcgtac tatggttgct ttgacgagca c 31

<210> SEQ ID NO 406
<211> LENGTH: 8064
<212> TYPE: DNA
<213> ORGANISM: Artificial
<220> FEATURE:

<223> OTHER INFORMATION: Synthetic construct

<400> SEQUENCE: 406

```
cacgttatac gtgctcgtca aagcaaccat agtacgcgcc ctgtagcggc gcattaagcg     60
cggcgggtgt ggtggttacg cgcagcgtga ccgctacact tgccagcgcc ctagcgcccg    120
ctcctttcgc tttcttccct tcctttctcg ccacgttcgc cggctttccc cgtcaagctc    180
taaatcgggg gctcccttta gggttccgat ttagtgcttt acggcacctc gaccccaaaa    240
aacttgattt gggtgatggt tcacgtagtg ggccatcgcc ctgatagacg gtttttcgcc    300
ctttgacgtt ggagtccacg ttctttaata gtggactctt gttccaaact ggaacaacac    360
tcaaccctat ctcgggctat tcttttgatt tataagggat tttgccgatt tcggaaccac    420
catcaaacag gattttcgcc tgctggggca aaccagcgtg gaccgcttgc tgcaactctc    480
tcagggccag gcggtgaagg gcaatcagct gttgcccgtc tcactggtga aaagaaaaac    540
caccctggcg cccaatacgc aaaccgcctc tccccgcgcg ttggccgatt cattaatgca    600
gctggcacga caggtttccc gactggaaag cgggcagtga gcgcaacgca attaatgtga    660
gttagctcac tcattaggca ccccaggctt tacactttat gcttccggct cgtatgttgt    720
gtggaattgt gagcggataa caatttcaca caggaaacag ctatgaccat gattacgaat    780
tcgagctcgg tacccgggga tcctcaactg tgaggaggct cacggacgcg aagaacaggc    840
acgcgtgctg gcagaaaccc ccggtatgac cgtgaaaacg gcccgccgca ttctggccgc    900
agcaccacag agtgcacagg cgcgcagtga cactgcgctg gatcgtctga tgcagggggc    960
accggcaccg ctggctgcag gtaacccggc atctgatgcc gttaacgatt tgctgaacac   1020
accagtgtaa gggatgttta tgacgagcaa agaaaccttt acccattacc agccgcaggg   1080
caacagtgac ccggctcata ccgcaaccgc gcccggcgga ttgagtgcga aagcgcctgc   1140
aatgaccccg ctgatgctgg acacctccag ccgtaagctg gttgcgtggg atggcaccac   1200
cgacggtgct gccgttggca ttcttgcggt tgctgctgac cagaccagca ccacgctgac   1260
gttctacaag tccggcacgt tccgttatga ggatgtgctc tggccggagg ctgccagcga   1320
cgagacgaaa aaacggaccg cgtttgccgg aacggcaatc agcatcgttt aactttaccc   1380
ttcatcacta aaggccgcct gtgcggcttt ttttacggga tttttttatg tcgatgtaca   1440
caaccgccca actgctggcg gcaaatgagc agaaatttaa gtttgatccg ctgtttctgc   1500
gtctcttttt ccgtgagagc tatcccttca ccacggagaa agtctatctc tcacaaattc   1560
cgggactggt aaacatggcg ctgtacgttt cgccgattgt ttccggtgag gttatccgtt   1620
cccgtggcgg ctccacctct gaaagcttgg cactggccgt cgttttacaa cgtcgtgact   1680
gggaaaaccc tggcgttacc caacttaatc gccttgcagc acatcccccc ttcgccagct   1740
ggcgtaatag cgaagaggcc cgcaccgatc gcccttccca acagttgcgc agcctgaatg   1800
gcgaatggcg ctttgcctgg tttccggcac cagaagcggt gccggaaagc tggctggagt   1860
gcgatcttcc tgaggccgat actgtcgtcg tcccctcaaa ctggcagatg cacggttacg   1920
atgcgcccat ctacaccaac gtgacctatc ccattacggt caatccgccg tttgttccca   1980
cggagaatcc gacgggttgt tactcgctca catttaatgt tgatgaaagc tggctacagg   2040
aaggccagac gcgaattatt tttgatggcg ttcctattgg ttaaaaaatg agctgattta   2100
acaaaaattt aatgcgaatt ttaacaaaat attaacgttt acaatttaaa tatttgctta   2160
tacaatcttc ctgtttttgg ggcttttctg attatcaacc ggggtacata tgattgacat   2220
gctagtttta cgattaccgt tcatcgattc tcttgtttgc tccagactct caggcaatga   2280
```

cctgatagcc tttgtagatc tctcaaaaat agctaccctc tccggcatta atttatcagc 2340
tagaacggtt gaatatcata ttgatggtga tttgactgtc tccggccttt ctcacccttt 2400
tgaatcttta cctacacatt actcaggcat tgcatttaaa atatatgagg gttctaaaaa 2460
tttttatcct tgcgttgaaa taaaggcttc tcccgcaaaa gtattacagg gtcataatgt 2520
ttttggtaca accgatttag ctttatgctc tgaggcttta ttgcttaatt ttgctaattc 2580
tttgccttgc ctgtatgatt tattggatgt taatgctact actattagta gaattgatgc 2640
caccttttca gctcgcgccc caaatgaaaa tatagctaaa caggttattg accatttgcg 2700
aaatgtatct aatggtcaaa ctaaatctac tcgttcgcag aattgggaat caactgttat 2760
atggaatgaa acttccagac accgtacttt agttgcatat ttaaaacatg ttgagctaca 2820
gcattatatt cagcaattaa gctctaagcc atccgcaaaa atgacctctt atcaaaagga 2880
gcaattaaag gtactctcta atcctgacct gttggagttt gcttccggtc tggttcgctt 2940
tgaagctcga attaaaacgc gatatttgaa gtctttcggg cttcctctta atctttttga 3000
tgcaatccgc tttgcttctg actataatag tcagggtaaa gacctgattt ttgatttatg 3060
gtcattctcg ttttctgaac tgtttaaagc atttgagggg gattcaatga atatttatga 3120
cgattccgca gtattggacg ctatccagtc taaacatttt actattaccc cctctggcaa 3180
aacttctttt gcaaaagcct ctcgctattt tggtttttat cgtcgtctgg taaacgaggg 3240
ttatgatagt gttgctctta ctatgcctcg taattccttt tggcgttatg tatctgcatt 3300
agttgaatgt ggtattccta aatctcaact gatgaatctt tctacctgta ataatgttgt 3360
tccgttagtt cgttttatta acgtagattt ttcttcccaa cgtcctgact ggtataatga 3420
gccagttctt aaaatcgcat aaggtaattc acaatgatta aagttgaaat taaaccatct 3480
caagcccaat ttactactcg ttctggtgtt tctcgtcagg gcaagcctta ttcactgaat 3540
gagcagcttt gttacgttga tttgggtaat gaatatccgg ttcttgtcaa gattactctt 3600
gatgaaggtc agccagccta tgcgcctggt ctgtacaccg ttcatctgtc ctctttcaaa 3660
gttggtcagt tcggttccct tatgattgac cgtctgcgcc tcgttccggc taagtaacat 3720
ggagcaggtc gcggatttcg acacaattta tcaggcgatg atacaaatct ccgttgtact 3780
ttgtttcgcg cttggtataa tcgctggggg tcaaagatga gtgttttagt gtattctttt 3840
gcctctttcg ttttaggttg gtgccttcgt agtggcatta cgtattttac ccgtttaatg 3900
gaaacttcct catgaaaaag tctttagtcc tcaaagcctc tgtagccgtt gctaccctcg 3960
ttccgatgct gtctttcgct gctgagggtg acgatcccgc aaaagcggcc tttaactccc 4020
tgcaagcctc agcgaccgaa tatatcggtt atgcgtgggc gatggttgtt gtcattgtcg 4080
gcgcaactat cggtatcaag ctgtttaaga aattcacctc gaaagcaagc tgataaaccg 4140
atacaattaa aggctccttt tggagccttt tttttggaga ttttcaacgt gaaaaaatta 4200
ttattcgcaa ttcctttagt tgttcctttc tattctcact ccgctgaaac tgttgaaagt 4260
tgtttagcaa aatcccatac agaaaattca tttactaacg tctggaaaga cgacaaaact 4320
ttagatcgtt acgctaacta tgagggctgt ctgtggaatg ctacaggcgt tgtagtttgt 4380
actggtgacg aaactcagtg ttacggtaca tgggttccta ttgggcttgc tatccctgaa 4440
aatgagggtg gtggctctga gggtggcggt tctgagggtg gcggttctga gggtggcggt 4500
actaaacctc ctgagtacgg tgatacacct attccgggct atacttatat caaccctctc 4560
gacggcactt atccgcctgg tactgagcaa aaccccgcta atcctaatcc ttctcttgag 4620
gagtctcagc ctcttaatac tttcatgttt cagaataata ggttccgaaa taggcagggg 4680
gcattaactg tttatacggg cactgttact caaggcactg accccgttaa aacttattac 4740
cagtacactc ctgtatcatc aaaagccatg tatgacgctt actggaacgg taaattcaga 4800
gactgcgctt tccattctgg ctttaatgag gatttatttg tttgtgaata tcaaggccaa 4860
tcgtctgacc tgcctcaacc tcctgtcaat gctggcggcg gctctggtgg tggttctggt 4920
ggcggctctg agggtggtgg ctctgagggt ggcggttctg agggtggcgg ctctgaggga 4980
ggcggttccg gtggtggctc tggttccggt gattttgatt atgaaaagat ggcaaacgct 5040
aataaggggg ctatgaccga aaatgccgat gaaaacgcgc tacagtctga cgctaaaggc 5100
aaacttgatt ctgtcgctac tgattacggt gctgctatcg atggtttcat tggtgacgtt 5160
tccggccttg ctaatggtaa tggtgctact ggtgattttg ctggctctaa ttcccaaatg 5220
gctcaagtcg gtgacggtga taattcacct ttaatgaata atttccgtca atatttacct 5280
tccctccctc aatcggttga atgtcgccct tttgtctttg gcgctggtaa accatatgaa 5340
ttttctattg attgtgacaa aataaactta ttccgtggtg tctttgcgtt tcttttatat 5400
gttgccacct ttatgtatgt attttctacg tttgctaaca tactgcgtaa taaggagtct 5460
taatcatgcc agttcttttg ggtattccgt tattattgcg tttcctcggt ttccttctgg 5520
taactttgtt cggctatctg cttacttttc ttaaaaaggg cttcggtaag atagctattg 5580
ctatttcatt gtttcttgct cttattattg ggcttaactc aattcttgtg ggttatctct 5640
ctgatattag cgctcaatta ccctctgact ttgttcaggg tgttcagtta attctcccgt 5700
ctaatgcgct tccctgtttt tatgttattc tctctgtaaa ggctgctatt ttcatttttg 5760
acgttaaaca aaaaatcgtt tcttatttgg attgggataa ataatatggc tgtttatttt 5820
gtaactggca aattaggctc tggaaagacg ctcgttagcg ttggtaagat tcaggataaa 5880
attgtagctg ggtgcaaaat agcaactaat cttgatttaa ggcttcaaaa cctcccgcaa 5940
gtcgggaggt tcgctaaaac gcctcgcgtt cttagaatac cggataagcc ttctatatct 6000
gatttgcttg ctattgggcg cggtaatgat tcctacgatg aaaataaaaa cggcttgctt 6060
gttctcgatg agtgcggtac ttggtttaat acccgttctt ggaatgataa ggaaagacag 6120
ccgattattg attggtttct acatgctcgt aaattaggat gggatattat ttttcttgtt 6180
caggacttat ctattgttga taaacaggcg cgttctgcat tagctgaaca tgttgtttat 6240
tgtcgtcgtc tggacagaat tactttacct tttgtcggta ctttatattc tcttattact 6300
ggctcgaaaa tgcctctgcc taaattacat gttggcgttg ttaaatatgg cgattctcaa 6360
ttaagcccta ctgttgagcg ttggctttat actggtaaga atttgtataa cgcatatgat 6420
actaaacagg ctttttctag taattatgat tccggtgttt attcttattt aacgccttat 6480
ttatcacacg gtcggtattt caaaccatta aatttaggtc agaagatgaa attaactaaa 6540
atatatttga aaaagttttc tcgcgttctt tgtcttgcga ttggatttgc atcagcattt 6600
acatatagtt atataaccca acctaagccg gaggttaaaa aggtagtctc tcagacctat 6660
gattttgata aattcactat tgactcttct cagcgtctta atctaagcta tcgctatgtt 6720
ttcaaggatt ctaagggaaa attaattaat agcgacgatt tacagaagca aggttattca 6780
ctcacatata ttgatttatg tactgtttcc attaaaaaag gtaattcaaa tgaaattgtt 6840
aaatgtaatt aattttgttt tcttgatgtt tgtttcatca tcttcttttg ctcaggtaat 6900
tgaaatgaat aattcgcctc tgcgcgattt tgtaacttgg tattcaaagc aatcaggcga 6960
atccgttatt gtttctcccg atgtaaaagg tactgttact gtatattcat ctgacgttaa 7020

-continued

```
acctgaaaat ctacgcaatt tctttatttc tgttttacgt gcaaataatt ttgatatggt   7080

aggttctaac ccttccatta ttcagaagta taatccaaac aatcaggatt atattgatga   7140

attgccatca tctgataatc aggaatatga tgataattcc gctccttctg gtggtttctt   7200

tgttccgcaa aatgataatg ttactcaaac ttttaaaatt aataacgttc gggcaaagga   7260

tttaatacga gttgtcgaat tgtttgtaaa gtctaatact tctaaatcct caaatgtatt   7320

atctattgac ggctctaatc tattagttgt tagtgctcct aaagatattt tagataacct   7380

tcctcaattc ctttcaactg ttgatttgcc aactgaccag atattgattg agggtttgat   7440

atttgaggtt cagcaaggtg atgctttaga tttttcattt gctgctggct ctcagcgtgg   7500

cactgttgca ggcggtgtta atactgaccg cctcacctct gttttatctt ctgctggtgg   7560

ttcgttcggt atttttaatg gcgatgtttt agggctatca gttcgcgcat taaagactaa   7620

tagccattca aaaatattgt ctgtgccacg tattcttacg ctttcaggtc agaagggttc   7680

tatctctgtt ggccagaatg tcccttttat tactggtcgt gtgactggtg aatctgccaa   7740

tgtaaataat ccatttcaga cgattgagcg tcaaaatgta ggtatttcca tgagcgtttt   7800

tcctgttgca atggctggcg gtaatattgt tctggatatt accagcaagg ccgatagttt   7860

gagttcttct actcaggcaa gtgatgttat tactaatcaa agaagtattg ctacaacggt   7920

taatttgcgt gatggacaga ctcttttact cggtggcctc actgattata aaaacacttc   7980

tcaggattct ggcgtaccgt tcctgtctaa aatcccttta atcggcctcc tgtttagctc   8040

ccgctctgat tctaacgagg aaag                                          8064
```